(12) United States Patent
Kuroda et al.

(10) Patent No.: US 7,067,537 B2
(45) Date of Patent: Jun. 27, 2006

(54) SUBSTITUTED THIAZOLE DERIVATIVES BEARING 3-PYRIDYL GROUPS, PROCESS FOR PREPARING THE SAME AND USE THEREOF

(75) Inventors: Noritaka Kuroda, Osaka (JP); Yoshi Nara, Suita (JP); Shohei Hashiguchi, Toyonaka (JP); Akihiro Tasaka, Suita (JP); Masami Kusaka, Kobe (JP); Masuo Yamaoka, Kobe (JP); Tomohiro Kaku, Nishinomiya (JP)

(73) Assignee: Takeda Pharmaceutical Company Limited, Osaka (JP)

(*) Notice: Subject to any disclaimer, the term of this patent is extended or adjusted under 35 U.S.C. 154(b) by 112 days.

(21) Appl. No.: 10/433,910

(22) PCT Filed: Dec. 7, 2001

(86) PCT No.: PCT/JP01/10723

§ 371 (c)(1),
(2), (4) Date: Jun. 4, 2003

(87) PCT Pub. No.: WO02/46186

PCT Pub. Date: Jun. 13, 2002

(65) Prior Publication Data

US 2004/0072876 A1    Apr. 15, 2004

(30) Foreign Application Priority Data

Dec. 8, 2000    (JP) .............................. 2000-373868

(51) Int. Cl.
*A01N 43/40* (2006.01)
*A61K 31/44* (2006.01)

(52) U.S. Cl. .................................. 514/342; 546/270.4
(58) Field of Classification Search ............. 546/270.4; 514/342
See application file for complete search history.

(56) References Cited

U.S. PATENT DOCUMENTS

| | | | |
|---|---|---|---|
| 3,821,384 A | 6/1974 | Ariyan et al. | |
| 4,153,703 A | 5/1979 | Harrison et al. ............ | 424/270 |
| 6,455,502 B1 | 9/2002 | Bryant et al. | |
| 6,476,026 B1 | 11/2002 | Bryant et al. | |
| 6,593,327 B1 | 7/2003 | Bryant et al. | |
| 2003/0096796 A1 | 5/2003 | Bryant et al. | |
| 2003/0119788 A1 | 6/2003 | Bryant et al. | |
| 2004/0147745 A1 | 7/2004 | Bryant et al. | |

FOREIGN PATENT DOCUMENTS

| | | |
|---|---|---|
| EP | 0149884 | 7/1986 |
| EP | 0721943 | 7/1996 |
| EP | 0820989 | 1/1998 |
| EP | 0974584 | 1/2000 |
| EP | 1227086 | 7/2002 |
| JP | 10195056 | 7/1998 |
| JP | 11 079993 | 3/1999 |
| JP | 2000-302680 | 10/2000 |
| WO | WO 94/27989 | 12/1994 |
| WO | WO 97/00257 | 1/1997 |
| WO | WO 97/30069 | 8/1997 |
| WO | WO 97/40846 | 11/1997 |
| WO | WO 98/08830 | 3/1998 |
| WO | WO 98/08844 | 3/1998 |
| WO | WO 98/32753 | 7/1998 |
| WO | WO 99/21555 | 5/1999 |
| WO | WO 99/54309 | 10/1999 |
| WO | WO 00/55126 | 9/2000 |
| WO | WO 00/64894 | 11/2000 |
| WO | WO 01/10865 | 2/2001 |
| WO | WO 01/68645 | 9/2001 |
| WO | WO 01/83461 | 11/2001 |
| WO | 03/027085 * | 3/2003 |

OTHER PUBLICATIONS

P. Sanfilippo, et al., "Synthesis of (Aryloxy)alkylamines 1. Novel Antisecretory Agents with H+K+-ATPase Inhibitory Activity", *Journal of Medicinal Chemistry*, (1988), vol. 31, No.9, pp. 1778-1785.

K. Brown. et al., "Nonsteroidal Antiinflammaroty Agents 1.2, 4-Diphenylthiazole-5-acetic Acid and Related Compounds", *Journal of Medical Chemistry*, (1974), vol. 17, No. 11, pp. 1177-1181.

* cited by examiner

Primary Examiner—Patricia L. Morris
(74) Attorney, Agent, or Firm—Elaine M. Ramesh; Mark Chao

(57) ABSTRACT

The present invention provides a pharmaceutical composition having a steroid $C_{17,20}$-lyase inhibitory activity, which is useful as a prophylactic or therapeutic agent of prostatism, tumor such as breast cancer and the like, more particularly, a steroid $C_{17,20}$-lyase inhibitor containing a compound represented by the formula:

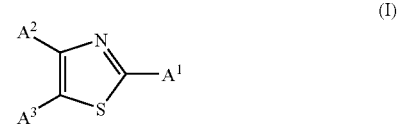

(I)

wherein $A^1$ is an aromatic hydrocarbon group optionally having substituents or a heterocyclic group optionally having substituents, one of $A^2$ and $A^3$ is a hydrogen atom, a halogen atom, a $C_{1-4}$ aliphatic hydrocarbon group optionally having substituents or an optionally esterified carboxyl group, the other of $A^2$ and $A^3$ is an aromatic hydrocarbon group optionally having substituents or a heterocyclic group optionally having substituents, and at least one of $A^1$, $A^2$ and $A^3$ is a 3-pyridyl group optionally having substituents, or a salt thereof or a prodrug thereof.

21 Claims, No Drawings

SUBSTITUTED THIAZOLE DERIVATIVES BEARING 3-PYRIDYL GROUPS, PROCESS FOR PREPARING THE SAME AND USE THEREOF

This application is the National Phase filing of International Patent Application No. PCT/JP01/10723, filed 07 Dec. 2001.

TECHNICAL FIELD

The present invention relates to a novel thiazole derivative having an inhibitory activity on steroid $C_{17-20}$-lyase, a salt thereof and to a pharmaceutical composition containing the same.

BACKGROUND ART

Androgen and estrogen, which are sex hormones, show a great diversity of physiological activities inclusive of differentiation and proliferation of cells. On the other hand, it has been clarified that androgen and estrogen act as an exacerbation factor in certain diseases. It is known that steroid $C_{17,\ 20}$-lyase is responsible for the final stage of the biosynthesis of androgen in the body. That is, steroid $C_{17,20}$-lyase produces dehydroepiandrosterone and androstenedione using, as a substrate, 17-hydroxypregnenolone and 17-hydroxyprogesterone, which are generated by cholesterol. Therefore, a pharmaceutical agent inhibiting steroid $C_{17,20}$-lyase suppresses production of androgen, as well as production of estrogen synthesized using androgen as a substrate. Such pharmaceutical agent is useful as an agent for the prevention and therapy of diseases wherein androgen and estrogen are exacerbation factors. Examples of the diseases, in which androgen or estrogen is an exacerbation factor, include prostate cancer, prostatic hypertrophy, masculinism, hypertrichosis, male-type baldness, male infant-type prematurity, breast cancer, uterine cancer, ovarian cancer, mastopathy, hysteromyoma, endometriosis, adenomyosis of uterus, polycystic ovary syndrome and the like.

Steroid-type compounds and non-steroid type compounds are already known as steroid $C_{17,20}$-lyase inhibitors. Steroid-type compounds are disclosed in, for example, WO92/15404, WO93/20097, EP-A-288053, EP-A-413270 and the like. As non-steroid type compounds, for example, JP-A-64-85975 discloses (1H-imidazol-1-yl)methyl-substituted benzimidazole derivatives, WO94/27989 and WO96/14090 disclose carbazole derivatives, WO95/09157 discloses azole derivatives, U.S. Pat. No. 5,491,161 discloses 1H-benzimidazole derivatives and WO99/18075 discloses dihydronaphthalene derivatives.

Heretofore, there has not been obtained a steroid $C_{17,20}$-lyase inhibitor applicable to clinical situations, and early development of a steroid $C_{17,20}$-lyase inhibitor highly useful as a pharmaceutical is desired.

DISCLOSURE OF THE INVENTION

The present inventors have conducted intensive studies in an attempt to find a superior steroid $C_{17,20}$-lyase inhibitor and found that a compound of the formula (I) unexpectedly has a superior pharmaceutical use, particularly a superior steroid $C_{17,20}$-lyase-inhibitory activity, and shows less toxicity and superior properties as a pharmaceutical product, based on its unique chemical structure.

Accordingly, the present invention relates to the following:

[1] A steroid $C_{17,20}$-lyase inhibitor comprising a compound represented by the formula:

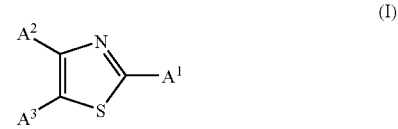

(I)

wherein
  $A^1$ is an aromatic hydrocarbon group optionally having substituents or a heterocyclic group optionally having substituents,
  one of $A^2$ and $A^3$ is a hydrogen atom, a halogen atom, a $C_{1-4}$ aliphatic hydrocarbon group optionally having substituents or an optionally esterified carboxyl group,
  the other of $A^2$ and $A^3$
    is an aromatic hydrocarbon group optionally having substituents or a heterocyclic group optionally having substituents, and
  at least one of $A^1$, $A^2$ and $A^3$
    is a 3-pyridyl group optionally having substituents,
  or a salt thereof or a prodrug thereof,

[2] the steroid $C_{17,20}$-lyase inhibitor of the above-mentioned [1], wherein one of $A^1$, $A^2$ and $A^3$ is a 3-pyridyl group optionally having substituents,

[3] the steroid $C_{17,20}$-lyase inhibitor of the above-mentioned [2], wherein (1) $A^1$ is a 3-pyridyl group optionally having substituents and $A^2$ is a $C_{6-14}$ aryl group optionally having substituents, or (2) $A^1$ is a 3-pyridyl group optionally having substituents and $A^2$ is a 3-pyridyl group optionally having substituents or (3) $A^1$ is a $C_{6-14}$ aryl group optionally having substituents and $A^2$ is a 3-pyridyl group optionally having substituents,

[4] the steroid $C_{17,20}$-lyase inhibitor of the above-mentioned [2], wherein one of $A^2$ and $A^3$ is 1) a hydrogen atom, 2) a $C_{1-4}$ aliphatic hydrocarbon group optionally having substituents, 3) an optionally esterified carboxyl group or 4) a halogen atom, the substituent of the "3-pyridyl group optionally having substituents", which is one of $A^1$, $A^2$ and $A^3$, is 1 to 4 groups selected from 1) a $C_{1-6}$ aliphatic hydrocarbon group optionally having substituents, 2) an optionally esterified carboxyl group, 3) a carbamoyl optionally having 1 or 2 substituents, 4) a cyclic aminocarbonyl optionally having substituents, 5) an amino optionally having substituents, 6) a cyclic amino optionally having substituents, 7) an alkylthio optionally having substituents, 8) an alkoxy optionally having substituents and 9) a halogen, or one saturated or unsaturated divalent $C_{3-5}$ carbon chain, and the other of $A^2$ and $A^3$ and the aromatic hydrocarbon group optionally having substituents or heterocyclic group optionally having substituents for $A^1$ are (a) a $C_{6-14}$ aryl optionally having, as a substituent, 1 to 5 groups selected from 1) a $C_{1-4}$ alkyl optionally having substituents, 2) a phenyl optionally having substituents, 3) a $C_{1-4}$ alkoxycarbonyl, 4) a carbamoyl optionally having substituents, 5) a $C_{1-2}$ alkylenedioxy, 6) an amino optionally having substituents, 7) a nitro, 8) a hydroxy optionally having substituents, 9) an optionally esterified carboxyl, 10) an alkylsulfonyl, 11) a sulfamoyl optionally having substituents and 12) a halogen, or (b) a pyridyl,

[5] the steroid $C_{17,20}$-lyase inhibitor of the above-mentioned [2], wherein one of $A^2$ and $A^3$ is 1) a hydrogen atom, 2) a $C_{1-4}$ alkyl optionally substituted by hydroxy, 3) a carboxyl, 4) a $C_{1-4}$ alkoxycarbonyl or 5) a halogen, and the other of $A^2$ and $A^3$ and the aromatic hydrocarbon group optionally having substituents or heterocyclic group optionally having substituents for $A^1$ are (a) a $C_{6-14}$ aryl optionally having, as a substituent, 1 to 5 groups selected from 1) a $C_{1-4}$ alkyl optionally having halogen, 2) a phenyl optionally having $C_{1-4}$ alkoxy, 3) a $C_{1-4}$ alkoxycarbonyl, 4) a carbamoyl optionally having 1 or 2 $C_{1-4}$ alkyl, 5) a $C_{1-2}$ alkylenedioxy, 6) an amino optionally having 1 or 2 substituents selected from $C_{1-4}$ alkyl, $C_{1-6}$ alkanoyl and $C_{1-4}$ alkylsulfonyl, 7) a nitro, 8) a hydroxy, 9) a $C_{1-4}$ alkoxy, 10) a $C_{1-4}$ alkanoyloxy, 11) a $C_{1-4}$ alkylsulfonyl, 12) a sulfamoyl optionally having 1 or 2 substituents selected from $C_{1-4}$ alkyl and benzyl and 13) a halogen or (b) a pyridyl, and the substituent of the "3-pyridyl group optionally having substituents", which is one of $A^1$, $A^2$ and $A^3$, is 1 to 4 groups selected from 1) a $C_{1-6}$ alkyl group optionally having, as a substituent, halogen or hydroxy, 2) a carboxyl group, 3) a $C_{1-4}$ alkoxycarbonyl group, 4) a carbamoyl optionally having, as a substituent, 1 or 2 $C_{1-4}$ alkyl, 5) a 4-benzylpiperidinocarbonyl, 6) an amino optionally having, as a substituent, 1 or 2 groups selected from carbamoylmethyl, $C_{1-4}$ alkyl and benzyl, 7) a morpholino, 8) a 4-(4-chlorophenyl)-4-hydroxypiperidino, 9) a $C_{1-4}$ alkylthio, 10) a $C_{1-4}$ alkoxy, 11) a halogen and 12) a butadienylene,

[6] the steroid $C_{17,20}$-lyase inhibitor of the above-mentioned [2], wherein one of $A^2$ and $A^3$ is a hydrogen atom, a methyl group, a chlorine atom or a fluorine atom, the other of $A^2$ and $A^3$ and the aromatic hydrocarbon group optionally having substituents or heterocyclic group optionally having substituents for $A^1$ are 1) a phenyl group optionally having, as a substituent, 1 or 2 groups selected from methyl, methoxycarbonyl, carbamoyl, trifluoromethyl, diethylamino, acetylamino, methylsulfonylamino, hydroxy, methoxy, sulfamoyl, methylsulfamoyl, fluorine and chlorine, 2) a naphthyl group or 3) a 3-pyridyl group, and the substituent of the "3-pyridyl group optionally having substituents", which is one of $A^1$, $A^2$ and $A^3$, is methyl, ethyl, trifluoromethyl, 1-hydroxy-1-methylethyl, carbamoylmethylamino, dimethylamino, morpholino, methylbenzylamino, methylthio, methoxy, isopropoxy or butadienylene,

[7] the steroid $C_{17,20}$-lyase inhibitor of the above-mentioned [3], wherein the 3-pyridyl group optionally having substituents is a 4-methyl-3-pyridyl group or a 4-trifluoromethyl-3-pyridyl group,

[8] the steroid $C_{17,20}$-lyase inhibitor of the above-mentioned [2], wherein $A^3$ is a hydrogen atom, a halogen atom, a $C_{1-4}$ alkyl group or a $C_{1-4}$ alkoxycarbonyl group,

[9] the steroid $C_{17,20}$-lyase inhibitor of the above-mentioned [3], wherein 3-pyridyl group optionally having substituents is a 3-pyridyl group, a 4-methyl-3-pyridyl group, a 4-trifluoromethyl-3-pyridyl group, a 4-methoxy-3-pyridyl group, a 4,5-butadienylene-3-pyridyl group, a 4-dimethylamino-3-pyridyl group, a 4-methylthio-3-pyridyl group, a 4-benzylmethylamino-3-pyridyl group, a 4-isopropoxy-3-pyridyl group, a 5-ethoxycarbonyl-3-pyridyl group, a 4-morpholino-3-pyridyl group, a 1-hydroxyisopropyl-3-pyridyl group, a 6-dimethylcarbamoyl-3-pyridyl group, a 4-hydroxy-4-(4-chlorophenyl)piperidino-3-pyridyl group, a 4-(N-methylcarbamoyl) 3-pyridyl group, a 4-ethyl-3-pyridyl group, a 4-carbamoylmethylamino-3-pyridyl group, a 4-carbamoyl-3-pyridyl group or a 4-(4-benzylpiperidinocarbonyl)-3-pyridyl group, and the $C_{6-14}$ aryl group optionally having substituents is a phenyl group, a 4-phenylphenyl group, a 3-nitrophenyl group, a 4-nitrophenyl group, a 4-hydroxyphenyl group, a 2-chlorophenyl group, a 3-chlorophenyl group, a 4-chlorophenyl group, a 3,4-dichlorophenyl group, a 2-fluorophenyl group, a 3-fluorophenyl group, a 4-fluorophenyl group, a 4-bromophenyl group, a 4-methylphenyl group, a 2,4-dimethylphenyl group, a 3,4-dimethylphenyl group, a 4-trifluoromethylphenyl group, a 2,4-bistrifluoromethylphenyl group, a 2-methoxyphenyl group, a 3-methoxyphenyl group, a 4-methoxyphenyl group, a 2,4-dimethoxyphenyl group, a 4-aminophenyl group, a 4-diethylaminophenyl group, a 4-methoxycarbonylphenyl group, a 4-ethoxycarbonylphenyl group, a 3-methylcarbamoylphenyl group, a 4-sulfamoylphenyl group, a 4-methylsulfamoylphenyl group, a 3,4-ethylenedioxyphenyl group, a 4-acetoxyphenyl group, a 4-methylsulfonylphenyl group, a 4-dibenzylsulfamoylphenyl group, 3-acetylaminophenyl group, a 4-acetylaminophenyl group, a 4-methylsulfonylaminophenyl group, a 3-methylsulfonylaminophenyl group, a 4-carbamoylphenyl group or a 2-naphthyl group,

[10] the steroid $C_{17,20}$-lyase inhibitor of the above-mentioned [2], which is a prophylactic or therapeutic agent of a sex hormone dependent disease,

[11] the steroid $C_{17,20}$-lyase inhibitor of the above-mentioned [2], which is a prophylactic or therapeutic agent of prostatic hypertrophy, masculinism, hypertrichosis, male-type baldness, male infant-type prematurity, endometriosis, hysteromyoma, adenomyosis of uterus, mastopathy or polycystic ovary syndrome,

[12] an androgen or estrogen reducing agent, which comprises a steroid $C_{17,20}$-lyase inhibitor and an LHRH receptor modulator in combination,

[13] an androgen or estrogen reducing agent comprising a compound represented by the formula:

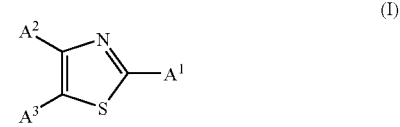

wherein
$A^1$ is an aromatic hydrocarbon group optionally having substituents or a heterocyclic group optionally having substituents,
one of $A^2$ and $A^3$
is a hydrogen atom, a halogen atom, a $C_{1-4}$ aliphatic hydrocarbon group optionally having substituents or an optionally esterified carboxyl group,
the other of $A^2$ and $A^3$
is an aromatic hydrocarbon group optionally having substituents or a heterocyclic group optionally having substituents, and
at least one of $A^1$, $A^2$ and $A^3$
is a 3-pyridyl group optionally having substituents, or a salt thereof or a prodrug thereof, and an LHRH receptor modulator in combination,

[14] a method for inhibiting steroid $C_{17,20}$-lyase, which comprises administering an effective amount of a compound represented by the formula:

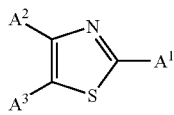

wherein
A¹ is an aromatic hydrocarbon group optionally having substituents or a heterocyclic group optionally having substituents,
one of A² and A³
is a hydrogen atom, a halogen atom, a $C_{1-4}$ aliphatic hydrocarbon group optionally having substituents or an optionally esterified carboxyl group,
the other of A² and A³
is an aromatic hydrocarbon group optionally having substituents or a heterocyclic group optionally having substituents, and
at least one of A¹, A² and A³
is a 3-pyridyl group optionally having substituents,
or a salt thereof or a prodrug thereof,

[15] use of a compound represented by the formula:

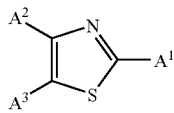

wherein
A¹ is an aromatic hydrocarbon group optionally having substituents or a heterocyclic group optionally having substituents,
one of A² and A³
is a hydrogen atom, a halogen atom, a $C_{1-4}$ aliphatic hydrocarbon group optionally having substituents or an optionally esterified carboxyl group,
the other of A² and A³
is an aromatic hydrocarbon group optionally having substituents or a heterocyclic group optionally having substituents, and
at least one of A¹, A² and A³
is a 3-pyridyl group optionally having substituents,
or a salt thereof or a prodrug thereof for the production of a steroid $C_{17,20}$-lyase inhibitor,

[16] a compound represented by the formula:

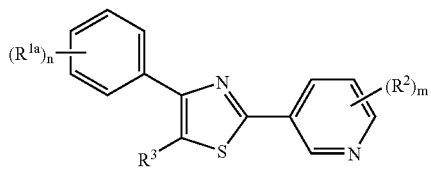

wherein
n is an integer of 1 to 5,
$R^{1a}$ is a sulfamoyl group optionally having substituents or an alkylsulfonyl group optionally having substituents, or two $R^{1a}$ substituting adjacent carbon atoms are bonded to designate a $C_{1-2}$ alkylenedioxy group, and when n is not less than 2, $R^{1a}$ in the number of n may be the same or different,
m is an integer of 1 to 5,
$R^2$ is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or two $R^2$ substituting adjacent carbon atoms may be bonded to form 9) a saturated or unsaturated divalent $C_{3-5}$ carbon chain, and when m is not less than 2, $R^2$ in the number of m may be the same or different, and
$R^3$ is 1) a hydrogen atom, 2) a halogen atom, 3) a $C_{1-4}$ aliphatic hydrocarbon group optionally having substituents or 4) an optionally esterified carboxyl group,
or a salt thereof,

[17] the compound of the above-mentioned [16], wherein $R^{1a}$ is 1) a sulfamoyl group optionally having $C_{1-4}$ alkyl or $C_{7-9}$ aralkyl as a substituent or 2) a $C_{1-4}$ alkylsulfonyl group, or two $R^{1a}$ substituting adjacent carbon atoms are bonded to designate a $C_{1-2}$ alkylenedioxy group, $R^2$ is 1) a hydrogen atom, 2) a $C_{1-4}$ alkyl optionally having halogen or hydroxy as a substituent, 3) a carboxyl group, 4) a $C_{1-4}$ alkoxycarbonyl group, 5) a carbamoyl group optionally having $C_{1-4}$ alkyl or $C_{7-9}$ aralkyl as a substituent, 6) an amino group optionally having $C_{1-4}$ alkyl, carbamoyl-$C_{1-4}$ alkyl or $C_{7-10}$ aralkyl as a substituent, 7) a piperidino group, 8) a morpholino group, 9) a $C_{1-4}$ alkylthio group or 10) a $C_{1-4}$ alkoxy group, or two adjacent $R^2$ are bonded to form 11) a butadienylene group, and $R^3$ is 1) a hydrogen atom, 2) a halogen atom, 3) a $C_{1-4}$ alkyl group, 4) a carboxyl group or 5) a $C_{1-4}$ alkoxycarbonyl group,

[18] the compound of the above-mentioned [16], wherein $R^{1a}$ is a sulfamoyl group, a methylsulfamoyl group, a dibenzylsulfamoyl group or a methylsulfonyl group, or two $R^{1a}$ substituting adjacent carbon atoms are bonded to designate an ethylenedioxy group, $R^2$ is a hydrogen atom, a methyl group, a trifluoromethyl group or a methoxy group, or two adjacent $R^2$ are bonded to form a butadienylene group, and $R^3$ is a hydrogen atom or a chlorine atom,

[19] a prodrug of a compound represented by the formula:

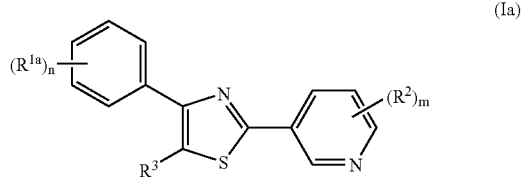

wherein
n is an integer of 1 to 5,
$R^{1a}$ is a sulfamoyl group optionally having substituents or an alkylsulfonyl group optionally having substituents, or two $R^{1a}$ substituting adjacent carbon atoms are bonded to designate a $C_{1-2}$ alkylenedioxy group, and when n is not less than 2, $R^{1a}$ in the number of n may be the same or different,
m is an integer of 1 to 5,
$R^2$ is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or two $R^2$ substituting adjacent carbon atoms may be bonded to form 9) a saturated or unsaturated divalent $C_{3-5}$ carbon chain, and when m is not less than 2, $R^2$ in the number of m may be the same or different, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[20] a compound represented by the formula:

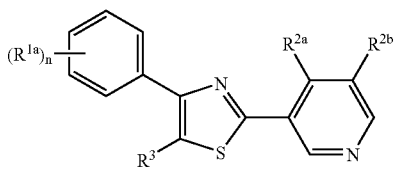

(Ia1)

wherein
n is an integer of 1 to 5,
$R^{1a}$ is a sulfamoyl group optionally having substituents or an alkylsulfonyl group optionally having substituents, or two $R^{1a}$ substituting adjacent carbon atoms are bonded to designate a $C_{1-2}$ alkylenedioxy group, and when n is not less than 2, $R^{1a}$ in the number of n may be the same or different, $R^{2a}$ and $R^{2b}$
are the same or different and each is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or $R^{2a}$ and $R^{2b}$ may be bonded to form 9) a saturated or unsaturated divalent $C_{3-5}$ carbon chain, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[21] the compound of the above-mentioned [20], wherein $R^{1a}$ is 1) a sulfamoyl group optionally having $C_{1-4}$ alkyl or a $C_{7-9}$ aralkyl as a substituent or 2) a $C_{1-4}$ alkylsulfonyl group, or two $R^{1a}$ substituting adjacent carbon atoms are bonded to designate a $C_{1-2}$ alkylenedioxy group, $R^{2a}$ and $R^{2b}$ are the same or different and each is 1) a hydrogen atom, 2) a $C_{1-4}$ alkyl optionally having halogen or hydroxy as a substituent, 3) a carboxyl group or a $C_{1-4}$ alkoxycarbonyl group, 4) a carbamoyl group optionally having $C_{1-4}$ alkyl or $C_{7-9}$ aralkyl as a substituent, 5) an amino group optionally having $C_{1-4}$ alkyl, carbamoyl-$C_{1-4}$ alkyl or $C_{7-10}$ aralkyl as a substituent, 6) a piperidino group or morpholino group, 7) a $C_{1-4}$ alkylthio group or 8) a $C_{1-4}$ alkoxy group, or $R^{2a}$ and $R^{2b}$ are bonded to form a butadienylene group, and $R^3$ is 1) a hydrogen atom, 2) a halogen atom, 3) a $C_{1-4}$ alkyl group, 4) a carboxyl group or 5) a $C_{1-4}$ alkoxycarbonyl group,

[22] the compound of the above-mentioned [20], wherein $R^{1a}$ is a sulfamoyl group, a methylsulfamoyl group, a dibenzylsulfamoyl group or a methylsulfonyl group, or two $R^{1a}$ substituting adjacent carbon atoms are bonded to designate an ethylenedioxy group, $R^{2a}$ is a hydrogen atom, a methyl group, a trifluoromethyl group or a methoxy group, $R^{2b}$ is a hydrogen atom, or $R^{2a}$ and $R^{2b}$ are bonded to form a butadienylene group, and $R^3$ is a hydrogen atom or a chlorine atom,

[23] a prodrug of a compound represented by the formula:

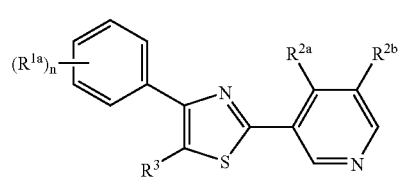

(Ia1)

wherein
n is an integer of 1 to 5,
$R^{1a}$ is a sulfamoyl group optionally having substituents or an alkylsulfonyl group optionally having substituents, or two $R^{1a}$ substituting adjacent carbon atoms are bonded to designate a $C_{1-2}$ alkylenedioxy group, and when n is not less than 2, $R^{1a}$ in the number of n may be the same or different, $R^{2a}$ and $R^{2b}$
are the same or different and each is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or $R^{2a}$ and $R^{2b}$ may be bonded to form 9) a saturated or unsaturated divalent $C_{3-5}$ carbon chain, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[24] a compound represented by the formula:

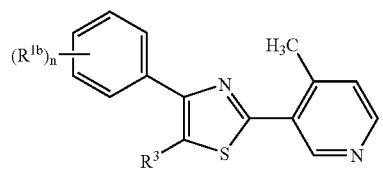

(Ia2)

wherein
n is an integer of 1 to 5,
$R^{1b}$ is 1) a sulfamoyl group optionally having substituents, 2) a carbamoyl group optionally having substituents, 3) an alkyl group optionally having substituents, 4) an optionally esterified carboxyl group, 5) a halogen atom, 6) an amino group optionally having substituents, 7) a nitro group, 8) a hydroxy group optionally having substituents or 9) an alkylsulfonyl group optionally having substituents, or two $R^{1b}$ substituting adjacent carbon atoms are bonded to designate a $C_{1-2}$ alkylenedioxy group, and when n is not less than 2, $R^{1b}$ in the number of n may be the same or different, and R³ is 1) a hydrogen atom, 2) a halogen atom, 3) a C₁₋₄ aliphatic hydrocarbon group optionally having substituents or 4) an optionally esterified carboxyl group, or a salt thereof,

[25] the compound of the above-mentioned [24], wherein R¹ᵇ is 1) a sulfamoyl group optionally having C₁₋₄ alkyl or C₇₋₉ aralkyl as a substituent, 2) a carbamoyl group optionally having C₁₋₄ alkyl or C₇₋₉ aralkyl as a substituent, 3) a C₁₋₄ alkyl group optionally having halogen as a substituent, 4) a carboxyl group, 5) a C₁₋₄ alkoxycarbonyl group, 6) a halogen atom, 7) an amino group optionally having C₁₋₆ alkanoyl, C₁₋₄ alkyl or C₁₋₄ alkylsulfonyl as a substituent, 8) a nitro group, 9) a hydroxy group optionally having C₁₋₄ alkyl or C₁₋₆ alkanoyl as a substituent or 10) a C₁₋₄ alkylsulfonyl group, or two R¹ᵇ substituting adjacent carbon atoms are bonded to designate a C₁₋₂ alkylenedioxy group, and R³ is 1) a hydrogen atom, 2) a halogen atom, 3) a C₁₋₄ alkyl group, 4) a carboxyl group or 5) a C₁₋₄ alkoxycarbonyl group,

[26] the compound of the above-mentioned [24], wherein R¹ᵇ is a sulfamoyl group, a methylsulfamoyl group, a dibenzylsulfamoyl group, a carbamoyl group, a methylcarbamoyl group, an ethylcarbamoyl group, a dimethylcarbamoyl group, an azetidine-1-ylcarbonyl group, a methyl group, a trifluoromethyl group, a carboxyl group, an ethoxycarbonyl group, a chlorine atom, a fluorine atom, a nitro group, a hydroxy group, a methoxy group or a methylsulfonyl group, or two R¹ᵇ substituting adjacent carbon atoms are bonded to designate an ethylenedioxy group, and R³ is a hydrogen atom, a chlorine atom, a fluorine atom or a methyl group,

[27] a prodrug a compound represented by the formula:

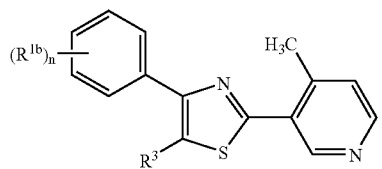

(Ia2)

wherein
n is an integer of 1 to 5,
R¹ᵇ is 1) a sulfamoyl group optionally having substituents, 2) a carbamoyl group optionally having substituents, 3) an alkyl group optionally having substituents, 4) an optionally esterified carboxyl group, 5) a halogen atom, 6) an amino group optionally having substituents, 7) a nitro group, 8) a hydroxy group optionally having substituents or 9) an alkylsulfonyl group optionally having substituents, or two R¹ᵇ substituting adjacent carbon atoms are bonded to designate a C₁₋₂ alkylenedioxy group, and when n is not less than 2, R¹ᵇ in the number of n may be the same or different, and
R³ is 1) a hydrogen atom, 2) a halogen atom, 3) a C₁₋₄ aliphatic hydrocarbon group optionally having substituents or 4) an optionally esterified carboxyl group, or a salt thereof,

[28] a compound represented by the formula:

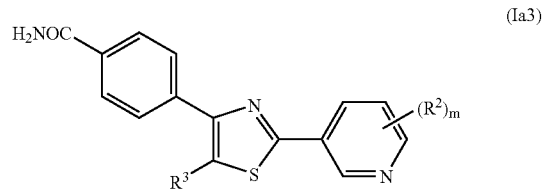

(Ia3)

wherein
m is an integer of 1 to 5,
R² is 1) a hydrogen atom, 2) a C₁₋₄ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or two R² substituting adjacent carbon atoms may be bonded to form 9) a saturated or unsaturated divalent C₃₋₅ carbon chain, and when m is not less than 2, R² in the number of m may be the same or different, and
R³ is 1) a hydrogen atom, 2) a halogen atom, 3) a C₁₋₄ aliphatic hydrocarbon group optionally having substituents or 4) an optionally esterified carboxyl group, or a salt thereof,

[29] the compound of the above-mentioned [28], wherein R² is 1) a hydrogen atom, 2) a C₁₋₄ alkyl optionally having halogen or hydroxy as a substituent, 3) a carboxyl group, 4) a C₁₋₄ alkoxycarbonyl group, 5) a carbamoyl group optionally having C₁₋₄ alkyl or C₇₋₉ aralkyl as a substituent, 6) an amino group optionally having C₁₋₄ alkyl, carbamoyl-C₁₋₄ alkyl or C₇₋₁₀ aralkyl as a substituent, 7) a piperidino group, 8) a morpholino group, 9) a C₁₋₄ alkylthio group or 10) a C₁₋₄ alkoxy group, or two adjacent R² are bonded to form 11) a butadienylene group, and R³ is 1) a hydrogen atom, 2) a halogen atom, 3) a C₁₋₄ alkyl group, 4) a carboxyl group or 5) a C₁₋₄ alkoxycarbonyl group,

[30] the compound of the above-mentioned [28], wherein R² is a hydrogen atom, a methyl group or a trifluoromethyl group, and R³ is a hydrogen atom,

[31] a prodrug of a compound represented by the formula:

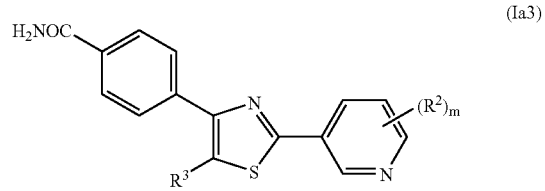

(Ia3)

wherein
m is an integer of 1 to 5,
R² is 1) a hydrogen atom, 2) a C₁₋₄ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or two R² substituting adjacent carbon atoms may be bonded to form 9) a saturated or unsaturated divalent $C_{3-5}$ carbon chain, and when m is not less than 2, $R^2$ in the number of m may be the same or different, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[32] a compound represented by the formula:

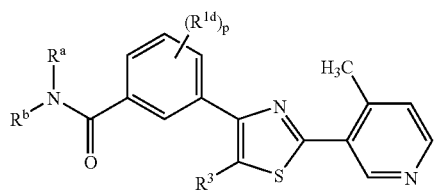

(Ia4)

wherein
p is 0 or an integer of 1 to 5,
$R^a$ and $R^b$
are the same or different and each is a hydrogen atom, a $C_{1-6}$ lower alkyl group, or $R^a$ and $R^b$ may be bonded together with a nitrogen atom to form a ring,
$R^{1d}$ is 1) a hydrogen atom, 2) a $C_{1-4}$ aliphatic hydrocarbon group optionally having substituents, 3) a sulfamoyl group optionally having substituents, 4) a carbamoyl group optionally having substituents, 5) an optionally esterified carboxyl group, 6) a halogen atom, 7) an amino group optionally having substituents, 8) a cyclic amino group, 9) a hydroxy group optionally having substituents, 10) an alkylthio group optionally having substituents, 11) a nitro group, 12) an alkylsulfonyl group optionally having substituents, or 13) two $R^{1d}$ substituting adjacent carbon atoms may be bonded to form 13a) a $C_{1-2}$ alkylenedioxy group or 13b) a saturated or unsaturated divalent $C_{3-5}$ carbon chain, and when p is not less than 2, $R^{1d}$ in the number of p may be the same or different, and
$R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[33] the compound of the above-mentioned [32], wherein $R^a$ and $R^b$ are the same or different and each is hydrogen atom, a methyl group or an ethyl group, or $R^a$ and $R^b$ are bonded together with a nitrogen atom to designate an azetidin-1-yl group, $R^{1d}$ is a hydrogen atom, and $R^3$ is a hydrogen atom,

[34] a prodrug of a compound represented by the formula:

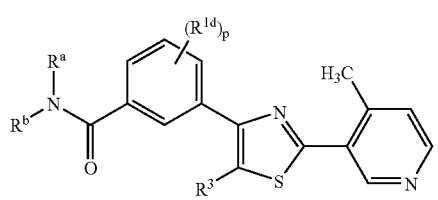

(Ia4)

wherein
p is 0 or an integer of 1 to 5,
$R^a$ and $R^b$
are the same or different and each is a hydrogen atom, a $C_{1-6}$ lower alkyl group, or $R^a$ and $R^b$ may be bonded together with a nitrogen atom to form a ring,
$R^{1d}$ is 1) a hydrogen atom, 2) a $C_{1-4}$ aliphatic hydrocarbon group optionally having substituents, 3) a sulfamoyl group optionally having substituents, 4) a carbamoyl group optionally having substituents, 5) an optionally esterified carboxyl group, 6) a halogen atom, 7) an amino group optionally having substituents, 8) a cyclic amino group, 9) a hydroxy group optionally having substituents, 10) an alkylthio group optionally having substituents, 11) a nitro group, 12) an alkylsulfonyl group optionally having substituents, or 13) two $R^{1d}$ substituting adjacent carbon atoms may be bonded to form 13a) a $C_{1-2}$ alkylenedioxy group or 13b) a saturated or unsaturated divalent $C_{3-5}$ carbon chain, and when p is not less than 2, $R^{1d}$ in the number of p may be the same or different, and
$R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[35] a compound represented by the formula:

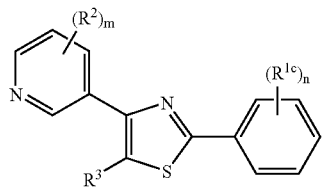

(Ib)

wherein
n is an integer of 1 to 5,
$R^{1c}$ is a carbamoyl group optionally having substituents or an alkylsulfonyl group optionally having substituents, or two $R^{1c}$ substituting adjacent carbon atoms are bonded to designate a $C_{1-2}$ alkylenedioxy group, and when n is not less than 2, $R^{1c}$ in the number of n are the same or different, m is an integer of 1 to 5,
$R^2$ is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or two $R^2$ substituting adjacent carbon atoms may be bonded to form 9) a saturated or unsaturated divalent $C_{3-5}$ carbon chain, and when m is not less than 2, $R^2$ in the number of m may be the same or different, and
$R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[36] the compound of the above-mentioned [35], wherein $R^{1c}$ is 1) a carbamoyl group optionally having $C_{1-4}$ alkyl or $C_{7-9}$ aralkyl as a substituent or 2) a $C_{1-4}$ alkylsulfonyl group, or two $R^{1b}$ substituting adjacent carbon atoms are bonded to designate a $C_{1-2}$ alkylenedioxy group, $R^2$ is 1) a hydrogen atom, 2) a $C_{1-4}$ alkyl optionally having halogen or hydroxy as a substituent, 3) a carboxyl group, 4) a $C_{1-4}$ alkoxycarbonyl group, 5) a carbamoyl group optionally having $C_{1-4}$ alkyl or $C_{7-9}$ aralkyl as a substituent, 6)

an amino group optionally having $C_{1-4}$ alkyl, carbamoyl-$C_{1-4}$ alkyl or $C_{7-10}$ aralkyl as a substituent, 7) a piperidino group, 8) a morpholino group, 9) a $C_{1-4}$ alkylthio group or 10) a $C_{1-4}$ alkoxy group, or two $R^2$ substituting adjacent carbon atoms are bonded to form 11) a butadienylene group, and $R^3$ is 1) a hydrogen atom, 2) a halogen atom, 3) a. $C_{1-4}$ alkyl group, 4) a carboxyl group or 5) a $C_{1-4}$ alkoxycarbonyl group,

[37] the compound of the above-mentioned [35], wherein $R^{1c}$ is a carbamoyl group, a methylcarbamoyl group, or a dimethylcarbamoyl group, $R^2$ is a hydrogen atom, a methyl group, an ethyl group or an isopropyl group, and $R^3$ is a hydrogen atom, a chlorine atom, a methyl group or an isopropyl group,

[38] a prodrug of a compound represented by the formula:

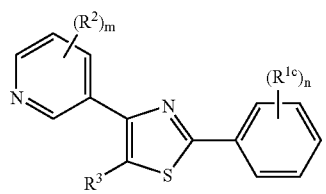

(Ib)

wherein n is an integer of 1 to 5, $R^{1c}$ is a carbamoyl group optionally having substituents or an alkylsulfonyl group optionally having substituents, or two $R^{1c}$ substituting adjacent carbon atoms are bonded to designate a $C_{1-2}$ alkylenedioxy group, and when n is not less than 2, $R^{1c}$ in the number of n are the same or different, m is an integer of 1 to 5, $R^2$ is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or two $R^2$ substituting adjacent carbon atoms may be bonded to form 9) a saturated or unsaturated divalent $C_{3-5}$ carbon chain, and when m is not less than 2, $R^2$ in the number of m may be the same or different, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[39] a compound represented by the formula:

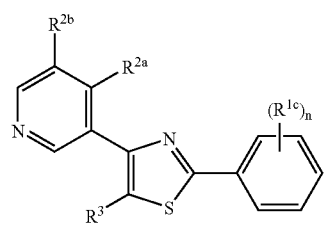

(Ib1)

wherein n is an integer of 1 to 5, $R^{1c}$ is a carbamoyl group optionally having substituents or an alkylsulfonyl group optionally having substituents, or two $R^{1c}$ substituting adjacent carbon atoms are bonded to designate a $C_{1-2}$ alkylenedioxy group, and when n is not less than 2, $R^{1c}$ in the number of n are the same or different, $R^{2a}$ and $R^{2b}$ are the same or different and each is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or $R^{2a}$ and $R^{2b}$ may be bonded to form 9) a saturated or unsaturated divalent $C_{3-5}$ carbon chain, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof, 40 the compound of the above-mentioned 39, wherein $R^{1c}$ C is 1) a carbamoyl group optionally having $C_{1-4}$ alkyl or $C_{7-9}$ aralkyl as a substituent or 2) a $C_{1-4}$ alkylsulfonyl group, or two $R^{1b}$ substituting adjacent carbon atoms are bonded to designate a $C_{1-2}$ alkylenedioxy group, $R^{2a}$ and $R_{2b}$ are the same or different and each is 1) a hydrogen atom, 2) a $C_{1-4}$ alkyl optionally having halogen or hydroxy as a substituent, 3) a carboxyl group or $C_{1-4}$ alkoxycarbonyl group, 4) a carbamoyl group optionally having CM alkyl or $C_{7-9}$ aralkyl as a substituent, 5) an amino group optionally having $C^{1-4}$ alkyl, carbamoyl-$C_{1-4}$ alkyl or $C_{7-10}$ aralkyl as a substituent, 6) a piperidino group or morpholino group, 7) a $C_{1-4}$ alkylthio group or 8) a $C_{1-4}$ alkoxy group, or $R^{2a}$ and $R^{2b}$ are bonded to form a butadienylene group, and $R^3$ is 1) a hydrogen atom, 2) a halogen atom, 3) a $C_{1-4}$ alkyl group, 4) a carboxyl group or 5) a $C_{1-4}$ alkoxycarbonyl group,

[41] the compound of the above-mentioned [39], wherein $R^{1c}$ is a carbamoyl group, a methylcarbamoyl group, or a dimethylcarbamoyl group, $R^{2a}$ is a methyl group, an ethyl group or an isopropyl group, $R^{2b}$ is a hydrogen atom, and $R^3$ is a hydrogen atom, a chlorine atom, a methyl group or an isopropyl group,

[42] a prodrug of a compound represented by the formula:

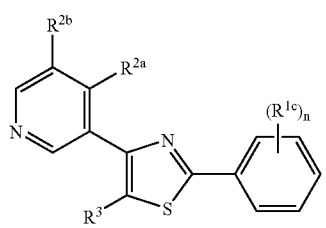

(Ib1)

wherein n is an integer of 1 to 5, $R^{1c}$ is a carbamoyl group optionally having substituents or an alkylsulfonyl group optionally having substituents, or two $R^{1c}$ substituting adjacent carbon atoms are bonded to designate a $C_{1-2}$ alkylenedioxy group, and when n is not less than 2, $R^{1c}$ in the number of n are the same or different, $R^{2a}$ and $R^{2b}$ are the same or different and each is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or $R^{2a}$ and $R^{2b}$ may be bonded to form 9) a saturated or unsaturated divalent $C_{3-5}$ carbon chain, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[43] a compound represented by the formula:

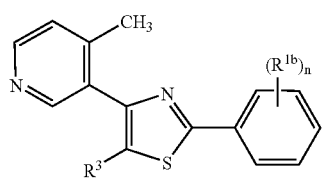

(Ib2)

wherein n is an integer of 1 to 5, $R^{1b}$ is 1) a sulfamoyl group optionally having substituents, 2) a carbamoyl group optionally having substituents, 3) an alkyl group optionally having substituents, 4) an optionally esterified carboxyl group, 5) a halogen atom, 6) an amino group optionally having substituents, 7) a nitro group, 8) a hydroxy group optionally having substituents or 9) an alkylsulfonyl group optionally having substituents, or two $R^{1b}$ substituting adjacent carbon atoms are bonded to designate a $C_{1-2}$ alkylenedioxy group, and when n is not less than 2, $R^{1b}$ in the number of n may be the same or different, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[44] the compound of the above-mentioned [43], wherein $R^{1b}$ is 1) a sulfamoyl group optionally having $C_{1-4}$ alkyl or $C_{7-9}$ aralkyl as a substituent, 2) a carbamoyl group optionally having $C_{1-4}$ alkyl or $C_{7-9}$ aralkyl as a substituent, 3) a $C_{1-4}$ alkyl group optionally having halogen as a substituent, 4) a carboxyl group, 5) a $C_{1-4}$ alkoxycarbonyl group, 6) a halogen atom, 7) an amino group optionally having $C_{1-6}$ alkanoyl, $C_{1-4}$ alkyl or $C_{1-4}$ alkylsulfonyl as a substituent, 8) a nitro group, 9) a hydroxy group optionally having $C_{1-4}$ alkyl or $C_{1-6}$ alkanoyl as a substituent or 10) a $C_{1-4}$ alkylsulfonyl group, or two $R^{1b}$ substituting adjacent carbon atoms are bonded to designate a $C_{1-2}$ alkylenedioxy group, and $R^3$ is 1) a hydrogen atom, 2) a halogen atom, 3) a $C_{1-4}$ alkyl group, 4) a carboxyl group or 5) a $C_{1-4}$ alkoxycarbonyl group,

[45] the compound of the above-mentioned [43], wherein $R^{1b}$ is a sulfamoyl group, a carbamoyl group, a methylcarbamoyl group, a dimethylcarbamoyl group, a pyrrolidin-1-ylcarbonyl group, a methyl group, a chlorine atom, a fluorine atom, an acetylamino group, a formylamino group or nitro group, and $R^3$ is a hydrogen atom, a chlorine atom, a methyl group or an isopropyl group,

[46] a prodrug of a compound represented by the formula:

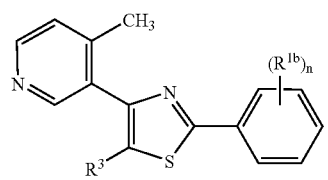

(Ib2)

wherein n is an integer of 1 to 5, $R^{1b}$ is 1) a sulfamoyl group optionally having substituents, 2) a carbamoyl group optionally having substituents, 3) an alkyl group optionally having substituents, 4) an optionally esterified carboxyl group, 5) a halogen atom, 6) an amino group optionally having substituents, 7) a nitro group, 8) a hydroxy group optionally having substituents or 9) an alkylsulfonyl group optionally having substituents, or two $R^{1b}$ substituting adjacent carbon atoms are bonded to designate a $C_{1-2}$ alkylenedioxy group, and when n is not less than 2, $R^{1b}$ in the number of n may be the same or different, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[47] a compound represented by the formula:

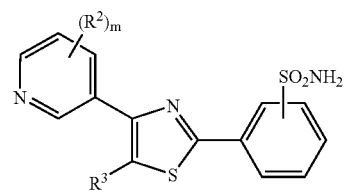

(Ib3)

wherein m is an integer of 1 to 5, $R^2$ is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or two $R^2$ substituting adjacent carbon atoms are bonded to form 9) a saturated or unsaturated divalent $C_{3-5}$ carbon chain, and when m is not less than 2, $R^2$ in the number of m may be the same or different, and $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[48] the compound of the above-mentioned [47], wherein $R^2$ is 1) a hydrogen atom, 2) a $C_{1-4}$ alkyl optionally having halogen or hydroxy as a substituent, 3) a carboxyl group, 4) a $C_{1-4}$ alkoxycarbonyl group, 5) a carbamoyl group optionally having $C_{1-4}$ alkyl or $C_{7-9}$ aralkyl as a substituent, 6) an amino group optionally having $C_{1-4}$ alkyl, carbamoyl-$C_{1-4}$ alkyl or $C_{7-10}$ aralkyl as a substituent, 7) a piperidino group, 8) a morpholino group, 9) a $C_{1-4}$ alkylthio group or 10) a $C_{1-4}$ alkoxy group, or two adjacent $R^2$ are bonded to form 11) a butadienylene group, and $R^3$ is 1) a hydrogen atom, 2) a halogen atom, 3) a $C_{1-4}$ alkyl group, 4) a carboxyl group or 5) a $C_{1-4}$ alkoxycarbonyl group,

[49] the compound of the above-mentioned [47], wherein $R^2$ is a hydrogen atom, a methyl group or an ethyl group and $R^3$ is a hydrogen atom or a methyl group,

[50] a prodrug of a compound represented by the formula:

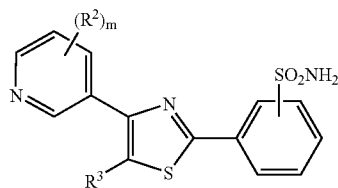

(Ib3)

wherein
  m is an integer of 1 to 5,
  $R^2$ is 1) a hydrogen atom, 2) a $C_{1-4}$ aliphatic hydrocarbon group optionally having substituents, 3) an optionally esterified carboxyl group, 4) a carbamoyl group optionally having substituents, 5) an amino group optionally having substituents, 6) a cyclic amino group, 7) an alkylthio group optionally having substituents or 8) an alkoxy group optionally having substituents, or two $R^2$ substituting adjacent carbon atoms are bonded to form 9) a saturated or unsaturated divalent $C_{3-5}$ carbon chain, and when m is not less than 2, $R^2$ in the number of m may be the same or different, and
  $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[51] a compound represented by the formula:

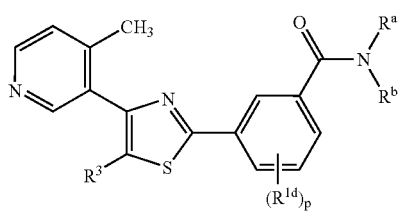

(Ib4)

wherein
  p is 0 or an integer of 1 to 5,
  $R^a$ and $R^b$
    are the same or different and each is a hydrogen atom or a $C_{1-6}$ lower alkyl group, or $R^a$ and $R^b$ may be bonded together with a nitrogen atom to form a ring,
  $R^{1d}$ is 1) a hydrogen atom, 2) a $C_{1-4}$ aliphatic hydrocarbon group optionally having substituents, 3) a sulfamoyl group optionally having substituents, 4) a carbamoyl group optionally having substituents, 5) an optionally esterified carboxyl group, 6) a halogen atom, 7) an amino group optionally having substituents, 8) a cyclic amino group, 9) a hydroxy group optionally having substituents, 10) an alkylthio group optionally having substituents, 11) a nitro group, 12) an alkylsulfonyl group optionally having substituents, or 13) two $R^{1d}$ substituting adjacent carbon atoms may be bonded to form 13a) a $C_{1-2}$ alkylenedioxy group or 13b) a saturated or unsaturated divalent $C_{3-5}$ carbon chain, and when p is not less than 2, $R^{1d}$ in the number of p may be the same or different, and
  $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[52] the compound of the above-mentioned [51], wherein $R^a$ and $R^b$ are the same or different and each is a hydrogen atom or a methyl group, or $R^a$ and $R^b$ are bonded together with a nitrogen atom to form a pyrrolidin-1-yl group, Rid is a hydrogen atom, a methyl group, a chlorine atom or a fluorine atom, and $R^3$ is a hydrogen atom, a chlorine atom, a methyl group or an isopropyl group,

[53] a prodrug of a compound represented by the formula:

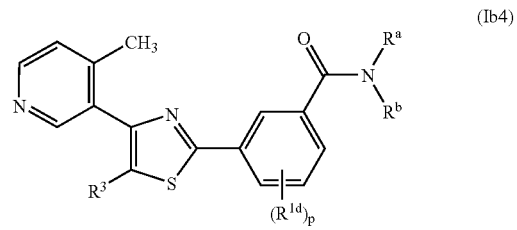

(Ib4)

wherein
  p is 0 or an integer of 1 to 5,
  $R^a$ and $R^b$
    are the same or different and each is a hydrogen atom or a $C_{1-6}$ lower alkyl group, or $R^a$ and $R^b$ may be bonded together with a nitrogen atom to form a ring,
  $R^{1d}$ is 1) a hydrogen atom, 2) a $C_{1-4}$ aliphatic hydrocarbon group optionally having substituents, 3) a sulfamoyl group optionally having substituents, 4) a carbamoyl group optionally having substituents, 5) an optionally esterified carboxyl group, 6) a halogen atom, 7) an amino group optionally having substituents, 8) a cyclic amino group, 9) a hydroxy group optionally having substituents, 10) an alkylthio group optionally having substituents, 11) a nitro group, 12) an alkylsulfonyl group optionally having substituents, or 13) two $R^{1d}$ substituting adjacent carbon atoms may be bonded to form 13a) a $C_{1-2}$ alkylenedioxy group or 13b) a saturated or unsaturated divalent $C_{3-5}$ carbon chain, and when p is not less than 2, $R^{1d}$ in the number of p may be the same or different, and
  $R^3$ is 1) a hydrogen atom, 2) a halogen atom, 3) a $C_{1-4}$ aliphatic hydrocarbon group optionally having substituents or 4) an optionally esterified carboxyl group, or a salt thereof,

[54] a compound represented by the formula:

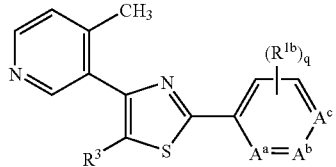

(Ic1)

wherein
q is 0 or an integer of 1 to 5,
$R^{1b}$ is 1) a sulfamoyl group optionally having substituents, 2) a carbamoyl group optionally having substituents, 3) an alkyl group optionally having substituents, 4) an optionally esterified carboxyl group, 5) a halogen atom, 6) an amino group optionally having substituents, 7) a nitro group, 8) a hydroxy group optionally having substituents or 9) an alkylsulfonyl group optionally having substituents, or 10) two $R^{1b}$ substituting adjacent carbon atoms are bonded to designate a $C_{1-2}$ alkylenedioxy group, and when q is not less than 2, $R^{1b}$ in the number of q may be the same or different,
$R^3$ is 1) a hydrogen atom, 2) a halogen atom, 3) a $C_{1-4}$ aliphatic hydrocarbon group optionally having substituents or 4) an optionally esterified carboxyl group, and
$A^a$, $A^b$ and $A^c$
are the same or different and each is a nitrogen atom or a methine group,
or a salt thereof,

[55] the compound of the above-mentioned [54], wherein $R^{1b}$ is a sulfamoyl group, a carbamoyl group, a methylcarbamoyl group, a dimethylcarbamoyl group, an ethylcarbamoyl group, a pyrrolidin-1-ylcarbonyl group, a methyl group, a chlorine atom, a fluorine atom, an acetylamino group, a formylamino group or a nitro group, $R^3$ is a hydrogen atom, a chlorine atom, a methyl group or an isopropyl group, and $A^a$, $A^b$ and $A^c$ are the same or different and each is a nitrogen atom or a methine group,

[56] a prodrug of a compound represented by the formula:

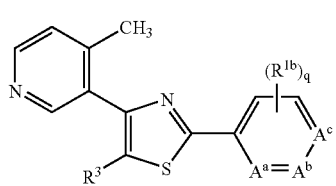

(Ic1)

wherein
q is 0 or an integer of 1 to 5,
$R^{1b}$ is 1) a sulfamoyl group optionally having substituents, 2) a carbamoyl group optionally having substituents, 3) an alkyl group optionally having substituents, 4) an optionally esterified carboxyl group, 5) a halogen atom, 6) an amino group optionally having substituents, 7) a nitro group, 8) a hydroxy group optionally having substituents or 9) an alkylsulfonyl group optionally having substituents, or 10) two $R^{1b}$ substituting adjacent carbon atoms are bonded to designate a $C_{1-2}$ alkylenedioxy group, and when q is not less than 2, $R^{1b}$ in the number of q may be the same or different,
$R^3$ is 1) a hydrogen atom, 2) a halogen atom, 3) a $C_{1-4}$ aliphatic hydrocarbon group optionally having substituents or 4) an optionally esterified carboxyl group, and
$A^a$, $A^b$ and $A^c$
are the same or different and each is a nitrogen atom or a methine group,
or a salt thereof,

[57] a compound represented by the formula:

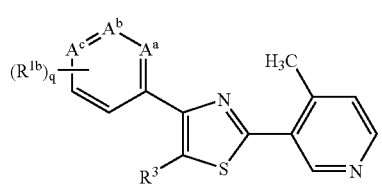

(Ic2)

wherein
q is 0 or an integer of 1 to 5,
$R^{1b}$ is 1) a sulfamoyl group optionally having substituents, 2) a carbamoyl group optionally having substituents, 3) an alkyl group optionally having substituents, 4) an optionally esterified carboxyl group, 5) a halogen atom, 6) an amino group optionally having substituents, 7) a nitro group, 8) a hydroxy group optionally having substituents or 9) an alkylsulfonyl group optionally having substituents, or 10) two $R^{1b}$ substituting adjacent carbon atoms are bonded to designate a $C_{1-2}$ alkylenedioxy group, and when q is not less than 2, $R^{1b}$ in the number of q are the same or different,
$R^3$ is 1) a hydrogen atom, 2) a halogen atom, 3) a $C_{1-4}$ aliphatic hydrocarbon group optionally having substituents or 4) an optionally esterified carboxyl group, and
$A^a$ $A^b$ and $A^c$
are the same or different and each is a nitrogen atom or a methine group,
or a salt thereof,

[58] the compound of the above-mentioned [57], wherein $R^{1b}$ is a sulfamoyl group, a methylsulfamoyl group, a dibenzylsulfamoyl group, a carbamoyl group, a methylcarbamoyl group, an ethylcarbamoyl group, a dimethylcarbamoyl group, an azetidin-1-ylcarbonyl group, a methyl group, a trifluoromethyl group, a carboxyl group, an ethoxycarbonyl group, a chlorine atom, a fluorine atom, a nitro group, a hydroxy group, a methoxy group or a methylsulfonyl group, or two $R^{1b}$ substituting adjacent carbon atoms are bonded to designate an ethylenedioxy group, $R^3$ is a hydrogen atom, a chlorine atom, a fluorine atom or a methyl group, $A^a$ is a methine, $A^b$ is a nitrogen atom or a methine, and $A^c$ is a nitrogen atom or a methine,

[59] a prodrug of a compound represented by the formula:

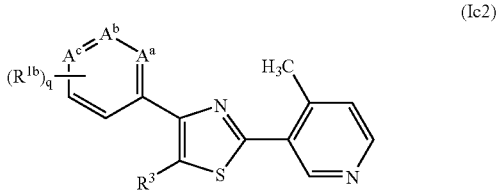

(Ic2)

wherein
q is 0 or an integer of 1 to 5,
$R^{1b}$ is 1) a sulfamoyl group optionally having substituents, 2) a carbamoyl group optionally having substituents, 3) an alkyl group optionally having substituents, 4) an optionally esterified carboxyl group, 5) a halogen atom, 6) an amino group optionally having substituents, 7) a nitro group, 8) a hydroxy group optionally having substituents or 9) an alkylsulfonyl group optionally having substituents, or 10) two $R^{1b}$ substituting adjacent carbon atoms are bonded to designate a $C_{1-2}$ alkylenedioxy group, and when q is not less than 2, $R^{1b}$ in the number of q are the same or different,
$R^3$ is 1) a hydrogen atom, 2) a halogen atom, 3) a $C_{1-4}$ aliphatic hydrocarbon group optionally having substituents or 4) an optionally esterified carboxyl group, and
$A^a$, $A^b$ and $A^c$
are the same or different and each is a nitrogen atom or a methine group,
or a salt thereof,
[60] 3-[4-(4-chlorophenyl)-1,3-thiazol-2-yl]-4-methylpyridine, 3-[4-(4-fluorophenyl)-1,3-thiazol-2-yl]-4-methylpyridine, 4-[2-(4-methyl-pyridin-3-yl)-1,3-thiazol-4-yl]benzenesulfonamide, 3-[2-(4-fluorophenyl)-1,3-thiazol-4-yl]-4-methylpyridine, 4-[4-(4-methyl-pyridin-3-yl)-1,3-thiazol-2-yl]benzenesulfonamide or a salt thereof, and the like.

DETAILED DESCRIPTION OF THE INVENTION

The compound represented by the aforementioned formula (I) or a salt thereof [hereinafter to be referred to as compound (I)] is a compound wherein 1) $A^1$ is a 3-pyridyl group optionally having substituents, $A^2$ is an aromatic hydrocarbon group optionally having substituents or a heterocyclic group optionally having substituents, $A^3$ is a hydrogen atom, a halogen atom, a $C_{1-4}$ aliphatic hydrocarbon group optionally having substituents or an optionally esterified carboxyl group, or a salt thereof [hereinafter to be referred to as compound (I-1)], 2) a compound wherein $A^1$ is an aromatic hydrocarbon group optionally having substituents or a heterocyclic group optionally having substituents, $A^2$ is a 3-pyridyl group optionally having substituents, $A^3$ is a hydrogen atom, a halogen atom, a $C_{1-4}$ aliphatic hydrocarbon group optionally having substituents or an optionally esterified carboxyl group, or a salt thereof [hereinafter to be referred to as compound (I-2)], 3) a compound wherein $A^1$ is a 3-pyridyl group optionally having substituents, $A^3$ is an aromatic hydrocarbon group optionally having substituents or a heterocyclic group optionally having substituents, $A^2$ is a hydrogen atom, a halogen atom, a $C_{1-4}$ aliphatic hydrocarbon group optionally having substituents or an optionally esterified carboxyl group, or a salt thereof [hereinafter to be referred to as compound (I-3)] or 4) a compound wherein $A^1$ is an aromatic hydrocarbon group optionally having substituents or a heterocyclic group optionally having substituents, $A^3$ is a 3-pyridyl group optionally having substituents, $A^2$ is a hydrogen atom, a halogen atom, a $C_{1-4}$ aliphatic hydrocarbon group optionally having substituents or an optionally esterified carboxyl group, or a salt thereof [hereinafter to be referred to as compound (I-4)]. Of these, compound (I-1) and compound (I-2) are preferable, and particularly a compound (I-1) wherein $A^2$ is a $C_{6-14}$ aryl group optionally having substituents or a 3-pyridyl group optionally having substituents and a compound (I-2), wherein $A^1$ is a $C_{6-14}$ aryl group optionally having substituents, is preferable.

As the "substituent" of the "3-pyridyl group optionally having substituents", which is one of the aforementioned $A^1$, $A^2$ and $A^3$, for example, 1) an oxo, 2) a halogen atom (e.g., fluorine atom, chlorine atom, bromine atom, iodine atom), 3) a nitro, 4) a cyano, 5) a $C_{1-6}$ aliphatic hydrocarbon group optionally having substituents, 6) a $C_{6-14}$ aryl (e.g., phenyl, 1-naphthyl, 2-naphthyl, 2-biphenylyl, 3-biphenylyl, 4-biphenylyl, 2-anthryl etc.), 7) a 5 to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), 8) an acyl group, 9) a carbamoyl optionally having substituents, 10) a cyclic aminocarbonyl optionally having substituents, 11) a thiocarbamoyl, 12) a sulfamoyl optionally having substituents [e.g., sulfamoyl, $C_{1-6}$ alkylsulfamoyl group (e.g., methylsulfamoyl etc.), $C_{7-15}$ aralkylsulfamoyl group (e.g., benzylsulfamoyl etc.)], 13) an amino optionally having substituents, 14) a cyclic amino optionally having substituents, 15) a mercapto group optionally having substituents, 16) a $C_{1-6}$ alkylsulfonyl (e.g., methylsulfonyl, ethylsulfonyl etc.), 17) a $C_{6-14}$ arylsulfonyl (e.g., phenylsulfonyl, 1-naphthylsulfonyl, 2-naphthylsulfonyl etc.), 18) a $C_{1-6}$ alkylsulfinyl (e.g., methylsulfinyl, ethylsulfinyl etc.), 19) a $C_{6-14}$ arylsulfinyl (e.g., phenylsulfinyl, 1-naphthylsulfinyl, 2-naphthylsulfinyl etc.), 20) a sulfo, 21) a sulfinamoyl, 22) a sulfenamoyl and 23) a hydroxy group optionally having substituents, and divalent groups such as 24) a saturated or unsaturated divalent $C_{3-5}$ carbon chain (e.g., trimethylene, tetramethylene, butadienylene etc.), 25) a $C_{1-3}$ alkylenedioxy (e.g., methylenedioxy, ethylenedioxy etc.) and the like can be mentioned.

As the above-mentioned $C_{1-6}$ aliphatic hydrocarbon group optionally having substituents, an optionally halogenated $C_{1-6}$ alkyl [e.g., $C_{1-6}$ alkyl (e.g., methyl, ethyl, propyl, isopropyl, butyl, isobutyl, sec-butyl, tert-butyl, pentyl, hexyl etc.) optionally having 1 to 5, preferably 1 to 3, halogen atoms (e.g., fluorine, chlorine, bromine, iodine etc.), such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl etc.], a hydroxy-$C_{1-6}$ alkyl (e.g., hydroxymethyl, hydroxyethyl, hydroxypropyl, hydroxy-isopropyl etc.), an optionally halogenated $C_{2-6}$ alkenyl [e.g., $C_{2-6}$ alkenyl (e.g., vinyl, propenyl, isopropenyl, 2-buten-1-yl, 4-penten-1-yl, 5-hexen-1-yl etc.) optionally having 1 to 5, preferably 1 to 3, halogen atoms (e.g., fluorine, chlorine, bromine, iodine etc.)], a carboxy $C_{2-6}$ alkenyl (e.g., 2-carboxyethenyl, 2-carboxy-2-methylethenyl etc.), an optionally halogenated $C_{2-6}$ alkynyl [e.g., $C_{2-6}$ alkynyl (e.g., 2-butyn-1-yl, 4-pentyn-1-yl, 5-hexyn-1-yl etc.) optionally having 1 to 5, preferably 1 to 3, halogen atoms (e.g., fluorine, chlorine, bromine, iodine etc.)], an optionally halogenated $C_{3-6}$ cycloalkyl [e.g., $C_{3-6}$ cycloalkyl (e.g., cyclopropyl, cyclobutyl, cyclopentyl, cyclohexyl etc.) optionally having 1 to 5, preferably 1 to 3, halogen atoms (e.g., fluorine, chlorine, bromine, iodine etc.) such as cyclopropyl, cyclobutyl, cyclopentyl, cyclohexyl, 4,4-dichlorocyclohexyl, 2,2,3,3-tetrafluorocyclopentyl, 4-chlorocyclohexyl etc.] and the like can be mentioned.

As the above-mentioned acyl group, an optionally esterified carboxyl group [e.g., unsubstituted carboxyl group etc., a $C_{1-6}$ alkoxy-carbonyl (e.g., methoxycarbonyl, ethoxycarbonyl, propoxycarbonyl, tert-butoxycarbonyl etc.)], a $C_{6-14}$ aryloxy-carbonyl (e.g., phenoxycarbonyl etc.), a $C_{7-16}$ aralkyloxy-carbonyl (e.g., benzyloxycarbonyl, phenethyloxycarbonyl etc.), a formyl, a $C_{1-6}$ alkyl-carbonyl (e.g., acetyl, propionyl etc.), a $C_{3-6}$ cycloalkyl-carbonyl (e.g., cyclopropylcarbonyl, cyclopentylcarbonyl, cyclohexylcarbonyl etc.), a $C_{6-14}$ aryl-carbonyl (e.g., benzoyl, 1-naphthoyl, 2-naphthoyl etc.), a $C_{7-16}$ aralkyl-carbonyl (e.g., phenylacetyl, 3-phenylpropionyl etc.), a 5 or 6-membered heterocyclic ring carbonyl (e.g., nicotinoyl, isonicotinoyl, thenoyl, furoyl etc.) and the like can be mentioned.

As the above-mentioned carbamoyl optionally having substituents, for example, an unsubstituted carbamoyl, and a mono-$C_{1-6}$ alkyl-carbamoyl (e.g., methylcarbamoyl, ethylcarbamoyl etc.), a di-$C_{1-6}$ alkyl-carbamoyl (e.g., dimethylcarbamoyl, diethylcarbamoyl, ethylmethylcarbamoyl etc.), a $C_{6-14}$ aryl-carbamoyl (e.g., phenylcarbamoyl, 1-naphthylcarbamoyl, 2-naphthylcarbamoyl etc.), a 5 or 6-membered heterocyclic carbamoyl (e.g., 2-pyridylcarbamoyl, 3-pyridylcarbamoyl, 4-pyridylcarbamoyl, 2-thienylcarbamoylo, 3-thienylcarbamoyl etc.) and the like can be mentioned.

As the above-mentioned cyclic aminocarbonyl optionally having substituents, for example, morpholinocarbonyl, thiomorpholinocarbonyl, piperazin-1-ylcarbonyl, 4-methylpiperazin-1-ylcarbonyl, pyrrolidin-1-ylcarbonyl, 3-methylpyrrolidin-1-ylcarbonyl and the like can be mentioned.

As the above-mentioned amino optionally having substituents, an unsubstituted amino, and a mono-$C_{1-6}$ alkylamino (e.g., methylamino, ethylamino etc.), a mono-$C_{6-14}$ arylamino (e.g., phenylamino, 1-naphthylamino, 2-naphthylamino etc.), a di-$C_{1-6}$ alkylamino (e.g., dimethylamino, diethylamino, ethylmethylamino etc.), a di-$C_{6-14}$ arylamino (e.g., diphenylamino etc.), a formylamino, a $C_{1-6}$ alkyl-carbonylamino (e.g., acetylamino etc.), a $C_{6-14}$ aryl-carbonylamino (e.g., benzoylamino, naphthoylamino etc.), a $C_{1-6}$ alkoxy-carbonylamino (e.g., methoxycarbonylamino, ethoxycarbonylamino, propoxycarbonylamino, butoxycarbonylamino etc.), a $C_{1-6}$ alkylsulfonylamino (e.g., methylsulfonylamino, ethylsulfonylamino etc.), a $C_{6-14}$ arylsulfonylamino (e.g., phenylsulfonylamino, 2-naphthylsulfonylamino, 1-naphthylsulfonylamino etc.) and the like can be mentioned.

As the-"cyclic amino" of the above-mentioned "cyclic amino optionally having substituents", a 5 to 7-membered saturated cyclic amino optionally having, besides one nitrogen atom and carbon atoms, 1 to 4 of 1 or 2 kinds of hetero atoms selected from nitrogen atom, sulfur atom and oxygen atom can be mentioned. Specific examples thereof include pyrrolidin-1-yl, piperidino, piperazin-1-yl, morpholino, thiomorpholino, hexahydroazepin-1-yl and the like.

As the "substituent" of the "cyclic amino optionally having substituents", for example, 1 to 3 substituents selected from a $C_{1-6}$ alkyl (e.g., methyl, ethyl, propyl, isopropyl, butyl, isobutyl, sec-butyl, tert-butyl, pentyl, hexyl etc.), a $C_{6-14}$ aryl (e.g., phenyl, 1-naphthyl, 2-naphthyl, 2-biphenylyl, 3-biphenylyl, 4-biphenylyl, 2-anthryl etc.), a $C_{1-6}$ alkyl-carbonyl (e.g., acetyl, propionyl etc.), a 5 to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), oxo and the like is/are used.

As the above-mentioned mercapto group optionally having substituents, an unsubstituted mercapto group, and an alkylthio optionally having substituents [e.g., unsubstituted $C_{1-6}$ alkylthio (e.g., methylthio, ethylthio, propylthio, butylthio, pentylthio etc.), optionally halogenated $C_{1-6}$ alkylthio], $C_{6-14}$ arylthio (e.g., phenylthio, 1-naphthylthio, 2-naphthylthio etc.), $C_{7-16}$ aralkylthio (e.g., benzylthio, phenethylthio etc.)] and the like can be mentioned.

As the above-mentioned hydroxy group optionally having substituents, an unsubstituted hydroxy, and an alkoxy optionally having substituents [e.g., optionally halogenated $C_{1-8}$ alkoxy (e.g., a $C_{1-8}$ alkoxy (e.g., methoxy, ethoxy, propoxy, isopropoxy, butoxy, isobutoxy, sec-butoxy, pentyloxy, hexyloxy etc.) optionally having 1 to 5, preferably 1 to 3, halogen atoms (e.g., fluorine, chlorine, bromine, iodine etc.) such as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.), a $C_{1-6}$ alkoxy-carbonyl-$C_{1-6}$ alkoxy (e.g., ethoxycarbonylmethyloxy etc.)], a $C_{6-14}$ aryloxy (e.g., phenyloxy, 1-naphthyloxy, 2-naphthyloxy etc.), a $C_{7-16}$ aralkyloxy (e.g., benzyloxy, phenethyloxy etc.), a $C_{1-6}$ alkyl-carbonyloxy (e.g., acetoxy, propionyloxy etc.), a $C_{6-14}$ aryl-carbonyloxy (e.g., benzoyloxy, naphthylcarbonyloxy etc.), a $C_{1-6}$ alkoxy-carbonyloxy (e.g., methoxycarbonyloxy, ethoxycarbonyloxy, propoxycarbonyloxy, butoxycarbonyloxy etc.), a mono-$C_{1-6}$ alkyl-carbamoyloxy (e.g., methylcarbamoyloxy, ethylcarbamoyloxy etc.), a di-$C_{1-6}$ alkyl-carbamoyloxy (e.g., dimethylcarbamoyloxy, diethylcarbamoyloxy etc.), a $C_{6-14}$ aryl-carbamoyloxy (e.g., phenylcarbamoyloxy, naphthylcarbamoyloxy etc.), a nicotinoyloxy and the like can be mentioned.

The "3-pyridyl group" may have, for example, 1 to 5, preferably 1 to 3, of the above-mentioned substituents at substitutable positions. When the number of substituent is not less than 2, respective substituents may be the same or different.

One of $A^2$ and $A^3$ is a hydrogen atom, a halogen atom, a $C_{1-4}$ hydrocarbon group optionally having substituents or an optionally esterified carboxyl group.

As the halogen atom, a fluorine atom, a chlorine atom, a bromine atom or an iodine atom is used, with preference given to fluorine atom, chlorine atom and bromine atom.

As the "$C_{1-4}$ hydrocarbon group" of the "$C_{1-4}$ hydrocarbon group optionally having substituents", a $C_{1-4}$ alkyl group (e.g., methyl, ethyl, propyl, isopropyl, butyl, isobutyl, sec-butyl, tert-butyl), a $C_{2-4}$ alkenyl group (e.g., vinyl, allyl, isopropenyl, 1-butenyl, 2-butenyl, 3-butenyl, 2-methyl-2-propenyl, 1-methyl-2-propenyl, 2-methyl-1-propenyl etc.), a $C_{2-4}$ alkynyl group (e.g., ethynyl, propargyl, 1-butynyl, 2-butynyl, 3-butynyl), a $C_{3-4}$ cycloalkyl group (e.g., cyclopropyl, cyclobutyl) and the like are used. Preferred is a $C_{1-4}$ alkyl group such as methyl, ethyl, propyl and the like, and particularly preferred is a methyl group.

As the "substituent" of the "$C_{1-4}$ hydrocarbon group optionally having substituents", a halogen atom (e.g., fluorine atom, chlorine atom, bromine atom, iodine atom), nitro, cyano, optionally halogenated $C_{3-6}$ cycloalkyl (e.g., cyclopropyl, cyclohexyl etc.), a $C_{6-14}$ aryl (e.g., phenyl, 1-naphthyl, 2-naphthyl, 2-biphenylyl, 3-biphenylyl, 4-biphenylyl, 2-anthryl etc.), an optionally halogenated $C_{1-4}$ alkoxy, a $C_{1-6}$ alkoxy-carbonyl-$C_{1-6}$ alkoxy (e.g., ethoxycarbonylmethyloxy etc.), hydroxy, a $C_{6-14}$ aryloxy (e.g., phenyloxy, 1-naphthyloxy, 2-naphthyloxy etc.), a $C_{7-16}$ aralkyloxy (e.g., benzyloxy, phenethyloxy etc.), a mercapto, an optionally halogenated $C_{1-6}$ alkylthio [e.g., $C_{1-6}$ alkylthio (e.g., methylthio, ethylthio, propylthio, isopropylthio, butylthio, sec-butylthio, tert-butylthio etc.) optionally having 1 to 5, preferably 1 to 3, halogen atoms (e.g., fluorine, chlorine, bromine, iodine etc.) such as methylthio, difluoromethylthio, trifluoromethylthio, ethylthio, propylthio, isopropylthio, butylthio, 4,4,4-trifluorobutylthio, pentylthio, hexylthio etc., and the like], a $C_{6-14}$ arylthio (e.g., phenylthio, 1-naphthylthio, 2-naphthylthio etc.), a $C_{7-16}$ aralkylthio (e.g., benzylthio, phenethylthio etc.), an amino, a mono-$C_{1-6}$ alkylamino (e.g., methylamino, ethylamino etc.), a mono-$C_{6-14}$ arylamino (e.g., phenylamino, 1-naphthylamino, 2-naphthylamino etc.), a di-$C_{1-6}$ alkylamino (e.g., dimethylamino, diethylamino, ethylmethylamino etc.), a di-$C_{6-14}$ arylamino (e.g., diphenylamino etc.), a formyl, a carboxy, a $C_{1-6}$ alkyl-carbonyl (e.g., acetyl, propionyl etc.), a $C_{3-6}$ cycloalkyl-carbonyl (e.g., cyclopropylcarbonyl, cyclopentylcarbonyl, cyclohexylcarbonyl etc.), a $C_{1-6}$ alkoxy-carbonyl (e.g., methoxycarbonyl, ethoxycarbonyl, propoxycarbonyl, tert-butoxycarbonyl etc.), a $C_{6-14}$ aryl-carbonyl (e.g., benzoyl, 1-naphthoyl, 2-naphthoyl etc.), a $C_{7-16}$ aralkyl-carbonyl (e.g., phenylacetyl, 3-phenylpropionyl etc.), a $C_{6-14}$ aryloxy-carbonyl (e.g., phenoxycarbonyl etc.), a $C_{7-16}$ aralkyloxy-carbonyl (e.g., benzyloxycarbonyl, phenethyloxycarbonyl etc.), a 5 or 6-membered heterocyclic carbonyl (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl etc.), a carbamoyl, a thiocarbamoyl, a mono-$C_{1-6}$ alkyl-carbamoyl (e.g., methylcarbamoyl, ethylcarbamoyl etc.), a di-$C_{1-6}$ alkyl-carbamoyl (e.g., dimethylcarbamoyl, diethylcarbamoyl, ethylmethylcarbamoyl etc.), a $C_{6-14}$ aryl-carbamoyl (e.g., phenylcarbamoyl, 1-naphthylcarbamoyl, 2-naphthylcarbamoyl etc.), a 5 or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.), a $C_{1-6}$ alkylsulfonyl (e.g., methylsulfonyl, ethylsulfonyl etc.), a $C_{6-14}$ arylsulfonyl (e.g., phenylsulfonyl, 1-naphthylsulfonyl, 2-naphthylsulfonyl etc.), a $C_{1-6}$ alkylsulfinyl (e.g., methylsulfinyl, ethylsulfinyl etc.), a $C_{6-14}$ arylsulfinyl (e.g., phenylsulfinyl, 1-naphthylsulfinyl, a 2-naphthylsulfinyl etc.), a formylamino, a $C_{1-6}$ alkyl-carbonylamino (e.g., acetylamino etc.), a $C_{6-14}$ aryl-carbonylamino (e.g., benzoylamino, naphthoylamino etc.), a $C_{1-6}$ alkoxy-carbonylamino (e.g., methoxycarbonylamino, ethoxycarbonylamino, propoxycarbonylamino, butoxycarbonylamino etc.), a $C_{1-6}$ alkylsulfonylamino (e.g., methylsulfonylamino, ethylsulfonylamino etc.), a $C_{6-14}$ arylsulfonylamino (e.g., phenylsulfonylamino, 2-naphthylsulfonylamino, 1-naphthylsulfonylamino etc.), a $C_{1-6}$ alkyl-carbonyloxy (e.g., acetoxy, propionyloxy etc.), a $C_{6-14}$ aryl-carbonyloxy (e.g., benzoyloxy, naphthylcarbonyloxy etc.), a $C_{1-6}$ alkoxy-carbonyloxy (e.g., methoxycarbonyloxy, ethoxycarbonyloxy, propoxycarbonyloxy, butoxycarbonyloxy etc.), a mono-$C_{1-6}$ alkyl-carbamoyloxy (e.g., methylcarbamoyloxy, ethylcarbamoyloxy etc.), a di-$C_{1-6}$ alkyl-carbamoyloxy (e.g., dimethylcarbamoyloxy, diethylcarbamoyloxy etc.), a $C_{6-14}$ aryl-carbamoyloxy (e.g., phenylcarbamoyloxy, naphthylcarbamoyloxy etc.), a nicotinoyloxy, a 5 to 7-membered saturated cyclic amino, a 5 to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), a sulfo, a sulfamoyl, a sulfinamoyl, a sulfenamoyl and the like are used.

As the optionally esterified carboxyl group, carboxyl group optionally esterified by $C_{1-4}$ alkyl group and the like, and the like are used, with preference given to a $C_{1-4}$ alkoxycarbonyl group such as methoxycarbonyl, ethoxycarbonyl and the like.

As the "aromatic hydrocarbon group" of the "aromatic hydrocarbon group optionally having substituents" represented by one of $A^1$, $A^2$ and $A^3$, for example, a monocycle having 6 to 14 carbon atoms or a condensed polycyclic (bicyclic or tricyclic) aromatic hydrocarbon group and the like can be mentioned. Specifically, for example, a $C_{6-14}$ aryl group such as phenyl, 1-naphthyl, 2-naphthyl, 2-biphenylyl, 3-biphenylyl, 4-biphenylyl, 2-anthryl and the like, from which a $C_{6-10}$ aryl group such as phenyl, 1-naphthyl, 2-naphthyl and the like is preferable, particularly a phenyl group is preferable.

As the "substituent" of the "aromatic hydrocarbon group optionally having substituents", those similar to the substituent of the aforementioned "3-pyridyl group" are used.

The "aromatic hydrocarbon group" may have, for example, 1 to 5, preferably 1 to 3, of the above-mentioned substituents at substitutable position(s). When the number of substituents is not less than 2, each substituent may be the same or different.

As the aromatic hydrocarbon group optionally having substituents, the aforementioned $C_{6-14}$ aryl group optionally having substituents is preferable.

As the "heterocyclic group" of the "heterocyclic group optionally having substituents", for example, 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like are mentioned, with preference given to pyridyl, particularly 3-pyridyl group.

As the "substituent" of the "heterocyclic group optionally having substituents", for example, those similar to the "substituent" of the aforementioned "3-pyridyl group optionally having substituents" are used.

The "heterocyclic group" may have, for example, 1 to 5, preferably 1 to 3, the above-mentioned substituents at substitutable position(s). When the number of substituents is not less than 2, each substituent may be the same or different. When a nitrogen atom is contained in the ring of the "heterocyclic group", the nitrogen atom may be N-oxidized.

As the substituent of the "3-pyridyl group optionally having substituents" and "heterocyclic group optionally having substituents", which is represented by one of the aforementioned $A^1$, $A^2$ and $A^3$, for example, an optionally halogenated $C_{1-6}$ alkyl group (e.g., methyl, ethyl, propyl, trifluoromethyl etc.), a hydroxy-$C_{1-6}$ alkyl group (e.g., hydroxymethyl, hydroxyethyl, hydroxypropyl, hydroxy-isopropyl etc.), a $C_{1-6}$ alkoxy group (e.g., methoxy, ethoxy, propoxy, isopropoxy etc.), a mono- or di-$C_{1-6}$ alkylamino group (e.g., methylamino, dimethylamino etc.), a $C_{1-6}$ alkylthio group (e.g., methylthio, ethylthio group), a ($C_{7-15}$ aralkyl)($C_{1-6}$ alkyl)amino group (e.g., (benzylmethyl)amino etc.), a $C_{1-6}$ alkoxy-carbonyl group (e.g., methoxy, ethoxy etc.), a mono- or di-$C_{1-6}$ alkylcarbamoyl group (e.g., methylcarbamoyl, dimethylcarbamoyl etc.), a carbamoyl group, a heterocyclic group containing, besides carbon atoms, 1 to 3 hetero atoms selected from nitrogen atom, sulfur atom and oxygen atom etc. (e.g., piperidino, piperazino, morpholino, thienyl, furyl, pyridyl, pyrimidinyl, quinolyl, isoquinolyl, imidazolyl etc., hereinafter sometimes to be abbreviated as a heterocyclic group), ($C_{7-15}$ aralkyl)(heterocyclic group) amino group (e.g., (4-benzylpiperidyl)amino etc.) and the like are preferable, and methyl, trifluoromethyl and the like are particularly preferable.

As the substituent of the aforementioned "aromatic hydrocarbon group" and "$C_{6-14}$ aryl group", a $C_{6-10}$ aryl group (e.g., phenyl etc.), a nitro group, a hydroxy group, a halogen atom (e.g., fluorine atom, chlorine atom, bromine atom), an optionally halogenated $C_{1-6}$ alkyl group (e.g., methyl, ethyl, propyl, isopropyl, trifluoromethyl, bistrifluoromethyl etc.), a $C_{1-6}$ alkoxy group (e.g., methoxy, ethoxy etc.), an amino group, a mono- or di-$C_{1-6}$ alkylamino group (e.g., methylamino, ethylamino, dimethylamino, diethylamino etc.), a $C_{1-6}$ alkoxy-carbonyl group (e.g., methoxycarbonyl, ethoxycarbonyl etc.), a $C_{1-6}$ alkylcarbamoyl group (e.g., methylcarbamoyl etc.), a sulfamoyl, a $C_{1-6}$ alkylsulfamoyl group (e.g., methylsulfamoyl etc.), a $C_{7-15}$ aralkylsulfamoyl group (e.g., benzylsulfamoyl etc.), a $C_{1-3}$ alkylenedioxy group (e.g., methylenedioxy, ethylenedioxy etc.), a $C_{1-6}$ alkylcarbonyloxy group (e.g., acetoxy etc.), a $C_{1-6}$ alkylsulfonyl group (e.g., methylsulfonyl etc.), a $C_{1-6}$ alkyl-carbonylamino group (e.g., acetylamino etc.), a $C_{1-6}$ alkylsulfonylamino group (e.g., methylsulfonylamino etc.), a carboxy group, a carbamoyl group and the like are preferable, and a halogen atom (e.g., fluorine atom, chlorine atom), aminosulfonyl group and the like are particularly preferable.

More specifically, as the "3-pyridyl group optionally having substituents" and "pyridyl group optionally having substituents", a 3-pyridyl group, a 4-methyl-3-pyridyl group, a 4-trifluoromethyl-3-pyridyl group, a 4-methoxy-3-pyridyl group, a 4-isoquinolyl-3-pyridyl group, a 4-methylamino-3-pyridyl group, a 4-dimethylamino-3-pyridyl group, a 4-methylthio-3-pyridyl group, a 4-(benzylmethyl)amino-3-pyridyl group, a 4-isopropoxy-3-pyridyl group, a 5-methoxycarbonyl-3-pyridyl group, a 5-ethoxycarbonyl-3-pyridyl group, a 4-morpholino-3-pyridyl group, a 1-hydroxyisopropyl-3-pyridyl group, a 6-dimethylcarbamoyl-3-pyridyl group, a 4-carbamoyl-3-pyridyl group, a 4-(4-benzylpiperidino)carbonyl-3-pyridyl group and the like are respectively preferable, and a 4-methyl-3-pyridyl group, a 4-trifluoromethyl-3-pyridyl group and the like are particularly preferable.

As the "aromatic hydrocarbon group optionally having substituents" and "$C_{6-14}$ aryl group optionally having substituents", a phenyl group, a biphenyl group, a 3-nitrophenyl group, a 4-nitro-phenyl group, a 4-hydroxy-3-pyridyl group, a 2-chloro-3-phenyl group, a 3-chloro-3-phenyl group, a 4-chloro-3-phenyl group, a 3,4-dichloro-3-phenyl group, a 2-fluoro-phenyl group, a 3-fluoro-phenyl group, a 4-fluoro-phenyl group, a 2,4-difluoro-phenyl group, a 4-bromo-phenyl group, a 4-methyl-phenyl group, a 2,4-dimethyl-phenyl group, a 3,4-dimethyl-phenyl group, a 4-trifluoromethyl-phenyl group, 2,4-bistrifluoromethyl-phenyl group, 2-methoxy-phenyl group, a 3-methoxy-phenyl group, a 4-methoxy-phenyl group, a 2,4-dimethoxy-phenyl group, a 2,5-dimethoxy-phenyl group, a 3-amino-phenyl group, a 4-amino-phenyl group, a 4-diethylamino-phenyl group, a 4-ethoxycarbonyl-phenyl group, a 3-methylcarbamoyl-phenyl group, a 4-methylsulfamoyl-phenyl group, a 3,4-ethylenedioxy-phenyl group, a 4-acetoxy-phenyl group, a 4-methylsulfonyl-phenyl group, a 4-sulfamoyl-phenyl group, a 4-dibenzylsulfamoyl-phenyl group, a 3-acetylamino-phenyl group, a 4-methylsulfonylamino-phenyl group, a 4-carboxy-phenyl group, a 4-carbamoyl-phenyl group, a 2-naphthyl group and the like are preferable.

As $A^3$, a hydrogen atom, a halogen atom (e.g., fluorine atom, chlorine atom, bromine atom), a $C_{1-4}$ alkyl group (e.g., methyl, ethyl) or a $C_{1-4}$ ethoxycarbonyl group (e.g., methoxycarbonyl, ethoxycarbonyl) and the like are preferable.

As the sulfamoyl group optionally having substituents represented by $R^{1a}$ in the aforementioned formulas (Ia) and (Ia1), for example, a sulfamoyl, a $C_{1-6}$ alkylsulfamoyl group (e.g., methylsulfamoyl etc.), a $C_{7-15}$ aralkylsulfamoyl group (e.g., benzylsulfamoyl etc.) can be mentioned, and as the alkylsulfonyl group optionally having substituents, for example, unsubstituted methylsulfonyl, ethylsulfonyl and the like, as well as an alkylsulfonyl substituted by halogen (e.g., chloromethylsulfonyl, 1,1-difluoroethylsulfonyl etc.) and the like can be mentioned. As the $C_{1-2}$ alkylenedioxy group designated by the two bonded $R^{1a}$ substituting adjacent carbon atoms, methylenedioxy and ethylenedioxy can be mentioned.

As the carbamoyl group optionally having substituents represented by $R^{1c}$ in the aforementioned formulas (Ib) and (Ib1), for example, an unsubstituted carbamoyl, as well as a mono-$C_{1-6}$ alkyl-carbamoyl (e.g., methylcarbamoyl, ethylcarbamoyl etc.), a di-$C_{1-6}$ alkyl-carbamoyl (e.g., dimethylcarbamoyl, diethylcarbamoyl, ethylmethylcarbamoyl etc.), a $C_{6-14}$ aryl-carbamoyl (e.g., phenylcarbamoyl, 1-naphthylcarbamoyl, 2-naphthylcarbamoyl etc.), a 5 or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl etc.) and the like can be mentioned.

As the alkylsulfonyl group optionally having substituents represented by $R^{1c}$, those mentioned as the alkylsulfonyl group optionally having substituents, which is represented by $R^{1a}$ can be mentioned.

As the $C_{1-2}$ alkylenedioxy group designated by the two bonded $R^{1c}$ substituting adjacent carbon atoms, methylenedioxy and ethylenedioxy can be mentioned.

As the sulfamoyl group optionally having substituents, which is represented by $R^{1b}$ in the aforementioned formulas (Ia2), (Ib2), (Ic1) and (Ic2), those mentioned as the sulfamoyl group optionally having substituents, which is represented by $R^{1a}$ can be mentioned, and as the carbamoyl group optionally having substituents, which is represented by $R^{1b}$ those mentioned as the carbamoyl group optionally having substituents, which is represented by $R^{1c}$, can be mentioned.

As the alkyl group optionally having substituents, which is represented by $R^{1b}$, an optionally halogenated $C_{1-6}$ alkyl [e.g., $C_{1-6}$ alkyl (e.g., methyl, ethyl, propyl, isopropyl, butyl, isobutyl, sec-butyl, tert-butyl, pentyl, hexyl etc.) optionally having 1 to 5, preferably 1 to 3, halogen atoms (e.g., fluorine, chlorine, bromine, iodine etc.), such as methyl, chloromethyl, difluoromethyl, trichloromethyl, trifluoromethyl, ethyl, 2-bromomethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like], and a hydroxy-$C_{1-6}$ alkyl (e.g., hydroxymethyl, hydroxyethyl, hydroxypropyl, hydroxy-isopropyl etc.) can be mentioned.

As the optionally esterified carboxyl group, which is represented by $R^{1b}$, for example, an unsubstituted carboxyl group, as well as a $C_{1-6}$ alkoxy-carbonyl (e.g., methoxycarbonyl, ethoxycarbonyl, propoxycarbonyl, tert-butoxycarbonyl etc.) can be mentioned.

As the halogen atom represented by $R^{1b}$, for example, fluorine, chlorine, bromine, iodine and the like can be mentioned.

As the amino group optionally having substituents, which is represented by $R^{1b}$, unsubstituted amino, as well as mono-$C_{1-6}$ alkylamino (e.g., methylamino, ethylamino etc.), mono-$C_{6-14}$ arylamino (e.g., phenylamino, 1-naphthylamino, 2-naphthylamino etc.), di-$C_{1-6}$ alkylamino (e.g., dimethylamino, diethylamino, ethylmethylamino etc.), di-$C_{6-14}$ arylamino (e.g., diphenylamino etc.), formylamino, $C_{1-6}$ alkyl-carbonylamino (e.g., acetylamino etc.), $C_{6-14}$ aryl-carbonylamino (e.g., benzoylamino, naphthoylamino etc.), $C_{1-6}$ alkoxy-carbonylamino (e.g., methoxycarbonylamino, ethoxycarbonylamino, propoxycarbonylamino, butoxycarbonylamino etc.), $C_{1-6}$ alkylsulfonylamino (e.g., methylsulfonylamino, ethylsulfonylamino etc.), $C_{6-14}$ arylsulfonylamino (e.g., phenylsulfonylamino, 2-naphthylsulfonylamino, 1-naphthylsulfonylamino etc.) and the like can be mentioned.

As the hydroxy group optionally having substituents, which is represented by $R^{1b}$, an unsubstituted hydroxy, as well as an alkoxy optionally having substituents [e.g., optionally halogenated $C_{1-8}$ alkoxy (e.g., $C_{1-8}$ alkoxy (e.g., methoxy, ethoxy, propoxy, isopropoxy, butoxy, isobutoxy, sec-butoxy, pentyloxy, hexyloxy etc.) optionally having 1 to 5, preferably 1 to 3, halogen atoms (e.g., fluorine, chlorine, bromine, iodine etc.), such as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy etc., and the like), a $C_{1-6}$ alkoxy-carbonyl-$C_{1-6}$ alkoxy (e.g., ethoxycarbonylmethyloxy etc.)], a $C_{6-14}$ aryloxy (e.g., phenyloxy, 1-naphthyloxy, 2-naphthyloxy etc.), a $C_{7-16}$ aralkyloxy (e.g., benzyloxy, phenethyloxy etc.), a $C_{1-6}$ alkyl-carbonyloxy (e.g., acetoxy, propionyloxy etc.), a $C_{6-14}$ aryl-carbonyloxy (e.g., benzoyloxy, naphthylcarbonyloxy etc.), a $C_{1-6}$ alkoxy-carbonyloxy (e.g., methoxycarbonyloxy, ethoxycarbonyloxy, propoxycarbonyloxy, butoxycarbonyloxy etc.), a mono-$C_{1-6}$ alkylcarbamoyloxy (e.g., methylcarbamoyloxy, ethylcarbamoyloxy etc.), a di-$C_{1-6}$ alkyl-carbamoyloxy (e.g., dimethylcarbamoyloxy, diethylcarbamoyloxy etc.), a $C_{6-14}$ aryl-carbamoyloxy (e.g., phenylcarbamoyloxy, naphthylcarbamoyloxy etc.), a nicotinoyloxy and the like can be mentioned.

As the alkylsulfonyl group optionally having substituents, which is represented by $R^{1b}$, those mentioned as the alkylsulfonyl group optionally having substituents, which is represented by $R^{1a}$, can be mentioned.

As the $C_{1-2}$ alkylenedioxy group designated by the two bonded $R^{1b}$ substituting adjacent carbon atoms, methylenedioxy and ethylenedioxy can be mentioned.

As the $C_{1-4}$ aliphatic hydrocarbon group optionally having substituents, which is represented by $R^2$ in the aforementioned formulas (Ia), (Ia3), (Ib) and (Ib3), an optionally halogenated $C_{1-4}$ alkyl [e.g., a $C_{1-4}$ alkyl (e.g., methyl, ethyl, propyl, isopropyl, butyl, isobutyl, sec-butyl, tert-butyl etc.) optionally having 1 to 5, preferably 1 to 3, halogen atoms (e.g., fluorine, chlorine, bromine, iodine etc.), such as methyl, chloromethyl, difluoromethyl, trichloromethyl, trifluoromethyl, ethyl, 2-bromomethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl etc.], a hydroxy-$C_{1-4}$ alkyl (e.g., hydroxymethyl, hydroxyethyl, hydroxypropyl, hydroxy-isopropyl etc.), an optionally halogenated $C_{2-4}$ alkenyl (e.g., $C_{2-4}$ alkenyl (e.g., vinyl, propenyl, isopropenyl, 2-buten-1-yl etc.) optionally having 1 to 5, preferably 1 to 3, halogen atoms (e.g., fluorine, chlorine, bromine, iodine etc.)), carboxy $C_{2-4}$ alkenyl (e.g., 2-carboxyethenyl, 2-carboxy-2-methylethenyl etc.), optionally halogenated $C_{2-4}$ alkynyl [e.g., a $C_{2-4}$ alkynyl (e.g., 1-fluoroethyne, 2-fluoroethyne, 2-butyn-1-yl etc.) optionally having 1 to 5, preferably 1 to 3, halogen atoms (e.g., fluorine, chlorine, bromine, iodine etc.)], an optionally halogenated $C_{3-4}$ cycloalkyl [e.g., a $C_{3-4}$ cycloalkyl (e.g., cyclopropyl, cyclobutyl etc.) optionally having 1 to 5, preferably 1 to 3, halogen atoms (e.g., fluorine, chlorine, bromine, iodine etc.), such as cyclopropyl, cyclobutyl etc.] and the like can be mentioned.

As the optionally esterified carboxyl group, which is represented by $R^2$, those mentioned as the optionally esterified carboxyl group, which is represented by $R^{1b}$, can be mentioned.

As the carbamoyl group optionally having substituents, which is represented by $R^2$, those mentioned as the carbamoyl group optionally having substituents, which is represented by $R^{1c}$ can be mentioned.

As the amino group optionally having substituents, which is represented by $R^2$, those mentioned as the amino group optionally having substituents, which is represented by $R^{1b}$ can be mentioned.

As the cyclic amino group represented by $R^2$, a 5 to 7-membered saturated cyclic amino optionally having, besides one nitrogen atom and carbon atoms, 1 to 4 of 1 or 2 kinds of hetero atoms selected from nitrogen atom, sulfur atom and oxygen atom. Specifically, pyrrolidin-1-yl, piperidino, piperazin-1-yl, morpholino, thiomorpholino, hexahydroazepin-1-yl and the like are used.

As the alkylthio group optionally having substituents, which is represented by $R^2$, for example, an unsubstituted $C_{1-6}$ alkylthio (e.g., methylthio, ethylthio, propylthio, butylthio, pentylthio etc.), an optionally halogenated $C_{1-6}$ alkylthio, a $C_{7-16}$ aralkylthio (e.g., benzylthio, phenethylthio etc.) and the like can be mentioned.

As the alkoxy group optionally having substituents, which is represented by $R^2$, for example, an optionally halogenated $C_{1-8}$ alkoxy [e.g., a $C_{1-8}$ alkoxy (e.g., methoxy, ethoxy, propoxy, isopropoxy, butoxy, isobutoxy, sec-butoxy, pentyloxy, hexyloxy etc.) optionally having 1 to 5, preferably 1 to 3, halogen atoms (e.g., fluorine, chlorine, bromine, iodine etc.), such as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy etc.], a $C_{1-6}$ alkoxy-carbonyl-$C_{1-6}$ alkoxy (e.g., ethoxycarbonylmethyloxy etc.) and the like can be mentioned.

As the saturated or unsaturated divalent $C_{3-5}$ carbon chain designated by the two bonded $R^2$ substituting adjacent carbon atoms, for example, trimethylene, tetramethylene, butadienylene and the like can be mentioned.

The $C_{1-4}$ aliphatic hydrocarbon group optionally having substituents, an optionally esterified carboxyl group, a carbamoyl group optionally having substituents, an amino group optionally having substituents, a cyclic amino group, an alkylthio group optionally having substituents and an alkoxy group optionally having substituents, which is represented by $R^{2a}$ and $R^{2b}$ in the aforementioned formulas (Ia1) and (Ib1), are the same as those exemplified for $R^2$, and examples of the saturated or unsaturated divalent $C_{3-5}$ carbon chain, which is designated by $R^{2a}$ and $R^{2b}$ bonded to each other, are the same as those exemplified for the saturated or unsaturated divalent $C_{3-5}$ carbon chain, which is designated by two $R^2$ bonded to each other.

As the $C_{1-4}$ aliphatic hydrocarbon group optionally having substituents, which is represented by $R^{1d}$ in the aforementioned formulas (Ia4) and (Ib4), those mentioned as the $C_{1-4}$ aliphatic hydrocarbon group optionally having substituents, which is represented by $R^2$ can be mentioned.

As the sulfamoyl group optionally having substituents, which is represented by $R^{1d}$, those mentioned as the sulfamoyl group optionally having substituents, which is represented by $R^{1a}$, can be mentioned.

As the carbamoyl group optionally having substituents, which is represented by $R^{1d}$, those mentioned as the carbamoyl group optionally having substituents, which is represented by $R^{1c}$, can be mentioned.

As the optionally esterified carboxyl group, which is represented by $R^{1d}$, those mentioned as the optionally esterified carboxyl group, which is represented by $R^{1d}$, can be mentioned.

As the halogen atom represented by $R^{1d}$, for example, fluorine, chlorine, bromine, iodine and the like can be mentioned.

As the amino group optionally having substituents, which is represented by $R^{1d}$, those mentioned as the amino group optionally having substituents, which is represented by $R^{1b}$ can be mentioned.

As the cyclic amino group, which is represented by $R^{1d}$, those mentioned as the cyclic amino group, which is represented by $R^2$, can be mentioned.

As the hydroxy group optionally having substituents, which is represented by $R^{1d}$, those mentioned as the hydroxy group optionally having substituents, which is represented by $R^{1b}$, can be mentioned.

As the alkylthio optionally having substituents group, which is represented by $R^{1d}$, those mentioned as the alkylthio optionally having substituents group, which is represented by $R^2$, can be mentioned.

As the alkylsulfonyl group optionally having substituents, which is represented by $R^{1d}$, those mentioned as the alkylsulfonyl group optionally having substituents, which is represented by $R^{1a}$, can be mentioned.

As the $C_{1-2}$ alkylenedioxy group designated by the two bonded $R^{1d}$ substituting adjacent carbon atoms, methylenedioxy and ethylenedioxy can be mentioned.

As the saturated or unsaturated divalent $C_{3-5}$ carbon chain designated by the two bonded $R^{1d}$ substituting adjacent carbon atoms, those mentioned as the saturated or unsaturated divalent $C_{3-5}$ carbon chain designated by bonded $R^2$, can be mentioned.

As the $C_{1-6}$ lower alkyl group represented by $R^a$ and $R^b$ in the aforementioned formulas (Ia4) and (Ib4), methyl, ethyl, propyl, isopropyl, butyl, isobutyl, sec-butyl, tert-butyl, pentyl, hexyl and the like can be mentioned.

As the ring formed by $R^a$ and $R^b$ bonded together with the nitrogen atom, azetidin-1-yl, pyrrolidin-1-yl, piperidino, morpholino and the like can be mentioned.

As the halogen atom represented by $R^3$ in the aforementioned formulas (Ia), (Ia1), (Ia2), (Ia3), (Ia4), (Ib), (Ib1), (Ib2), (Ib3), (Ib4), (Ic1) and (Ic2), fluorine atom, chlorine atom, bromine atom, iodine atom and the like can be mentioned.

As the $C_{1-4}$ aliphatic hydrocarbon group optionally having substituents designated by $R^3$, those mentioned as the $C_{1-4}$ aliphatic hydrocarbon group optionally having substituents represented by $R^2$ can be mentioned.

As the optionally esterified carboxyl group represented by $R^3$, those mentioned as the optionally esterified carboxyl group represented by $R^{1b}$ can be mentioned.

The compounds represented by the aforementioned formulas (Ia), (Ia1), (Ia2), (Ia3), (Ia4), (Ib), (Ib1), (Ib2), (Ib3), (Ib4), (Ic1) and (Ic2) are all encompassed in the compound represented by the formula (I).

More specifically, for example, the compounds produced by Examples 1-83 to be mentioned below are used as compound (I), of which 3-[4-(4-chlorophenyl)-1,3-thiazol-2-yl]-4-methylpyridine (compound No. 74), 3-[4-(4-fluorophenyl)-1,3-thiazol-2-yl]-4-methylpyridine (compound No. 78), 4-[2-(4-methyl-pyridin-3-yl)-1,3-thiazol-4-yl]benzenesulfonamide (compound No. 154), 3-[2-(4-fluorophenyl)-1,3-thiazol-4-yl]-4-methylpyridine (compound No. 137), 4-[4-(4-methyl-pyridin-3-yl)-1,3-thiazol-2-yl]benzenesulfonamide (compound No. 135) and the like are preferable.

As the salts of the compounds represented by the formula (I), for example, a metal salt, an ammonium salt, a salt with an organic base, a salt with an inorganic acid, a salt with an organic acid, a salt with a basic or acidic amino acid and the like can be mentioned. Preferable examples of the metal salt are, for example, alkali metal salts such as sodium salt, potassium salt and the like; alkaline earth metal salts such as calcium salt, magnesium salt, barium salt and the like; aluminum salt and the like can be mentioned. Preferable examples of the salt with an organic base are, for example, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like can be mentioned. Preferable examples of the salt with an inorganic acid are, for example, salts with hydrochloric acid, hydrobromic acid, nitric acid, sulfuric acid, phosphoric acid and the like can be mentioned. Preferable examples of the salt with an organic acid are, for example, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. Preferable examples of the salt with a basic amino acid are, for example, salts with arginine, lysine, ornithine and the like can be mentioned and preferable examples of the salt with an acidic amino acid are, for example, salts with aspartic acid, glutamic acid and the like can be mentioned.

Of these, a pharmacologically acceptable salt is preferable. For example, when the compound has an acidic functional group therein, an inorganic salt such as an alkali metal salt (e.g., sodium salt, potassium salt etc.), an alkaline earth metal salt (e.g., calcium salt, magnesium salt, barium salt etc.) and the like, an ammonium salt and the like can be mentioned. When the compound has a basic functional group therein, for example, a salt with an inorganic acid such as hydrochloric acid, hydrobromic acid, nitric acid, sulfuric acid, phosphoric acid and the like, or a salt with an organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

Now the production method of the compound represented by the formula (I) is described. Throughout the present specification, the starting compounds and synthetic intermediates may be used as a free form or a salt similar to the salts of compound (I), or may be subjected to a reaction in the form of a reaction mixture, or after isolation according to a known means. In the following, a compound represented by the formula (symbol accorded to the formula) or a salt thereof is simply referred to as compound (symbol accorded to the formula).

Production Method 1

The compound (I-1) can be produced by the reaction shown by the following formulas.

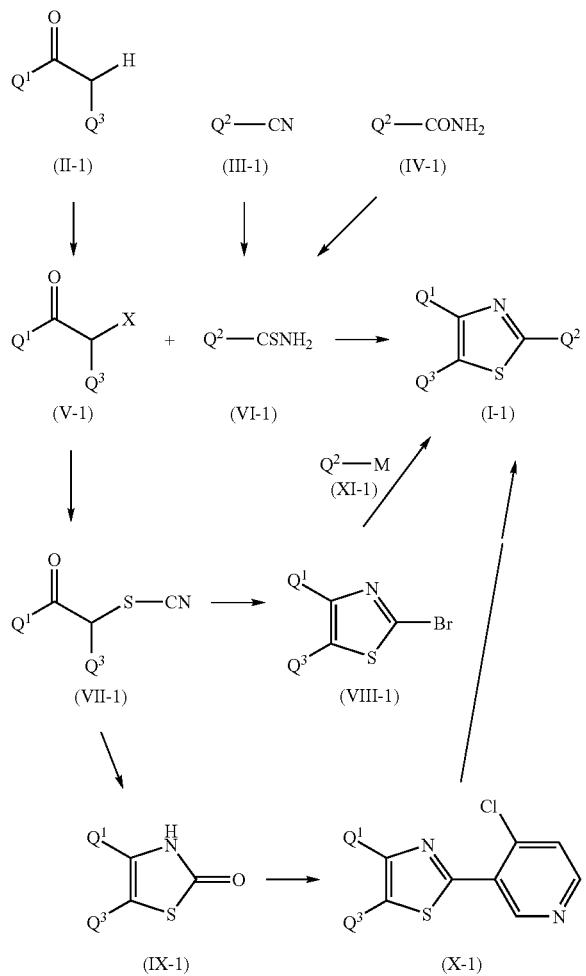

wherein $Q^1$ is an aromatic hydrocarbon group optionally having substituents or a heterocyclic group optionally having substituents, $Q^2$ is a 3-pyridyl group optionally having substituents, $Q^3$ is a hydrogen atom, a halogen atom, a $C_{1-4}$ aliphatic hydrocarbon group optionally having substituents or an optionally esterified carboxyl group, X is a halogen atom such as chlorine atom, a bromine atom and the like, M is an alkali metal atom such as potassium, sodium, lithium and the like.

The compound (V-1) can be obtained by halogenating compound (II-1) according to a method known per se or a method analogous thereto. This reaction can be performed according to a method known per se, such as the method described in Shin Jikken Kagaku Koza (New Courses in Experimental Chemistry), vol. 14, p. 331 (Maruzen) or a method analogous thereto. As the halogenating agent used for this reaction, chlorine, bromine, NCS, NBS, phosphorus pentachloride, cupric bromide and the like are mentioned. Particularly, bromine and cupric bromide are preferable. In this reaction, the halogenating agent is used in 1 to 10 equivalents, preferably 1-3 equivalents, relative to ketone form (II-1). The reaction temperature is from 20° C. to 100° C., preferably 0° C.–50° C. The reaction time is about 5 min. to 20 hrs. This reaction is generally carried out in an organic solvent that does not affect the reaction. As the organic solvent that does not affect the reaction, for example, organic acids such as acetic acid and the like, acetic acid esters such as ethyl acetate, isopropyl acetate and the like, ethers such as diethyl ether, dioxane, tetrahydrofuran and the like, saturated hydrocarbons such as hexane, pentane and the like, halogenated hydrocarbons such as dichloromethane, chloroform and the like, aromatic hydrocarbons such as benzene, toluene and the like, and the like are used. These may be used upon mixing one or more kinds thereof at an appropriate ratio.

In addition, compound (VI-1) can be obtained by thioamidating compound (III-1) according to a method known per se or a method analogous thereto. This reaction can be performed by a method known per se, such as the method described in Shin Jikken Kagaku Koza (New Courses in Experimental Chemistry), vol. 14, p. 1827 (Maruzen) or a method analogous thereto. In this reaction, hydrogen sulfide is mainly used as a thioamidating agent. The reaction temperature is from 20° C. to 100° C., preferably 20° C.–50° C. The reaction time is about 5 min. to 20 hrs. This reaction is generally carried out in an organic solvent that does not affect the reaction. As the organic solvent that does not affect the reaction, for example, basic solvents such as DMF, DMSO and the like, ethers such as diethyl ether, dioxane, tetrahydrofuran and the like, saturated hydrocarbons such as hexane, pentane and the like, halogenated hydrocarbons such as dichloromethane, chloroform and the like, aromatic hydrocarbons such as benzene, toluene and the like, and the like are used. These may be used upon mixing one or more kinds thereof at an appropriate ratio. In addition, compound (VI-1) can be also synthesized from the corresponding carboxamide compound (IV-1) according to a method described in, for example, Shin Jikken Kagaku Koza (New Courses in Experimental Chemistry), vol. 14, p. 1827 (Maruzen).

The thiazole compound (I-1) can be obtained by subjecting compound (V-1) and compound (VI-1) to a reaction known per se, such as reaction according to, for example, Shin Jikken Kagaku Koza (New Courses in Experimental Chemistry), vol. 14, p. 2191 (Maruzen) or a method analogous thereto. In this reaction, a solvent inert to the reaction, such as THF, alcohols, dichloromethane and the like are used. The compound (V-1) is used in a 0.2 to 2 equivalents, preferably 1.0 to 1.5 equivalents, relative to compound (VI-1). The reaction temperature is 0° C.–150° C., preferably 20° C.–120° C.

The compound (I-1) can be also synthesized by a method that goes through compound (VII-1) and compound (VIII-1) or compound (VII-1) and compounds (IX-1) and (X-1). That is, compound (I-1) can be obtained by converting compound (V-1) to thiocyanate compound (VII-1), and then to bromothiazole (VIII-1) according to a method known per se, such as a method of Journal of Indian Chemical Society, vol. 37, pp. 773–774 (1960) or Tetrahedron, vol. 56, pp. 3161–3165 (2000), and coupling the compound with compound (XI-1)(M is metal) prepared separately, by a reaction known per se, such as a method described in, for example, Tetrahedron Letters, vol. 41, pp. 1707–1710 (2000) or a method analogous thereto.

In addition, compound (I-1) can be also obtained from compound (VII-1) by a reaction known per se, such as the method described in Journal of Indian Chemical Society, vol. 32, pp. 427–430 (1955) or a method analogous thereto via compounds (IX-1) and (X-1). In compound (1–1), moreover, the functional group of $Q^1$, $Q^2$ and $Q^3$ can be converted by a reaction known per se, such as the method described in *Tetrahedron Letters*, vol. 41, pp. 1707–1710 (2000) or a method analogous thereto. Specifically, acylation and alkylation of $Q^1$ and $Q^3$, and halogenation of $Q^2$ and the like are included.

Production Method 2

The compound (I-2) can be produced by the reaction shown by the following formula.

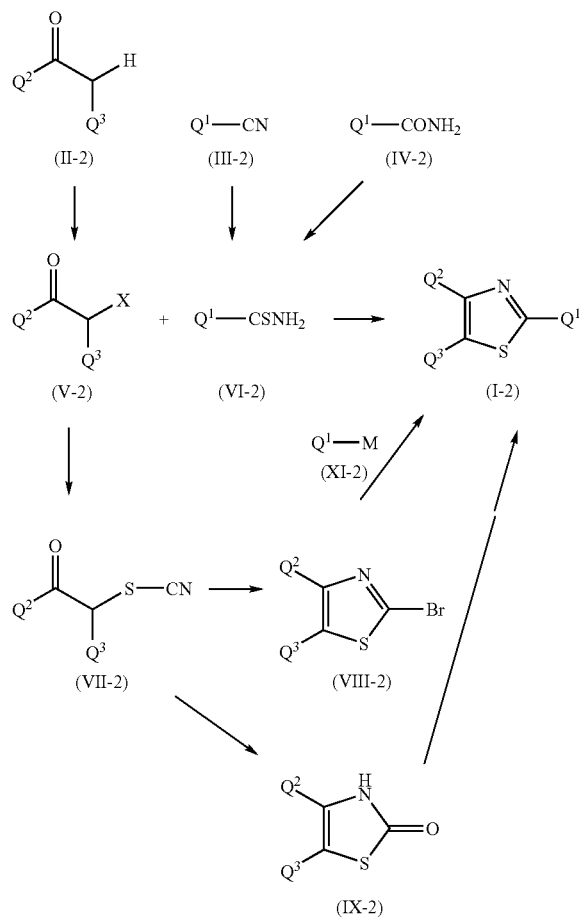

wherein each symbol is as defined above.

The compound (V-2) can be obtained by halogenating compound (II-2) according to a method known per se or a method analogous thereto. This reaction can be performed according to a method known per se, such as the method described in *Shin Jikken Kagaku Koza* (*New Courses in Experimental Chemistry*), vol. 14, p. 331 (Maruzen) or a method analogous thereto. As the halogenating agent used for this reaction, chlorine, bromine, NCS, NBS, phosphorus pentachloride, cupric bromide and the like are mentioned. Particularly, bromine and cupric bromide are preferable. In this reaction, the halogenating agent is used in 1 to 10 equivalents, preferably 1–3 equivalents, relative to ketone form (II-2). The reaction temperature is from 20° C. to 100° C., preferably 0° C.–50° C. The reaction time is about 5 min. to 20 hrs. This reaction is generally carried out in an organic solvent that does not affect the reaction. As the organic solvent that does not affect the reaction, for example, organic acids such as acetic acid and the like, acetic acid esters such as ethyl acetate, isopropyl acetate and the like, ethers such as diethyl ether, dioxane, tetrahydrofuran and the like, saturated hydrocarbons such as hexane, pentane and the like, halogenated hydrocarbons such as dichloromethane, chloroform and the like, aromatic hydrocarbons such as benzene, toluene and the like, and the like are used. These may be used upon mixing one or more kinds thereof at an appropriate ratio.

In addition, compound (VI-2) can be obtained by thioamidating compound (III-2) according to a method known per se or a method analogous thereto. This reaction can be performed by a method known per se, such as the method described in *Shin Jikken Kagaku Koza* (*New Courses in Experimental Chemistry*), vol. 14, p. 1827 (Maruzen) or a method analogous thereto. In this reaction, hydrogen sulfide is mainly used as a thioamidating agent. The reaction temperature is from 20° C. to 100° C., preferably 20° C.–50° C. The reaction time is about 5 min. to 20 hrs. This reaction is generally carried out in an organic solvent that does not affect the reaction. As the organic solvent that does not affect the reaction, for example, basic solvents such as DMF, DMSO and the like, ethers such as diethyl ether, dioxane, tetrahydrofuran and the like, saturated hydrocarbons such as hexane, pentane and the like, halogenated hydrocarbons such as dichloromethane, chloroform and the like, aromatic hydrocarbons such as benzene, toluene and the like, and the like are used. These may be used upon mixing one or more kinds thereof at an appropriate ratio. In addition, compound (VI-2) can be also synthesized from the corresponding carboxamide compound (IV-2) according to a method described in, for example, *Shin Jikken Kagaku Koza* (*New Courses in Experimental Chemistry*), vol. 14, p. 1827 (Maruzen).

The thiazole compound (I-2) can be obtained by subjecting compound (V-2) and compound (VI-2) to a reaction known per se, such as reaction according to, for example, *Shin Jikken Kagaku Koza* (*New Courses in Experimental Chemistry*), vol. 14, p. 2191 (Maruzen) or a method analogous thereto. In this reaction, a solvent inert to the reaction, such as THF, alcohols, dichloromethane and the like are used. The compound (V-2) is used in a 0.2 to 2 equivalents, preferably 1.0 to 1.5 equivalents, relative to compound (VI-2). The reaction temperature is 0° C.–150° C., preferably 20° C.–120° C.

The compound (I-2) can be also synthesized by a method that goes through compound (VII-2) and compound (VIII-2) or compound (VII-2) and compound (IX-2). That is, compound (I-2) can be obtained by converting compound (V-2) to thiocyanate compound (VII-2), and then to bromothiazole (VIII-2) according to a method known per se, such as a method of *Journal of Indian Chemical Society*, vol. 37, pp. 773–774 (1960) or *Tetrahedron*, vol. 56, pp. 3161–3165 (2000), and coupling the compound with compound (XI-2)(M is metal) prepared separately, by a reaction known per se, such as a method described in, for example, *Tetrahedron Letters*, vol. 41, pp. 1707–1710 (2000) or a method analogous thereto.

In addition, compound (I-2) can be also obtained from compound (VII-2) by a reaction known per se, such as the method described in *Journal of Indian Chemical Society*, vol. 32, pp. 427–430 (1955) or a method analogous thereto via compound (IX-2). In compound (I-2), moreover, the functional group of $Q^1$, $Q^2$ and $Q^3$ can be converted by a reaction known per se, such as the method described in *Tetrahedron Letters*, vol. 41, pp. 1707–1710 (2000) or a method analogous thereto. Specifically, acylation and alkylation of $Q^1$ and $Q^3$, and halogenation of $Q^2$ and the like are included.

Production Method 3

The compound (I-3) can be produced by the reaction shown by the following formula.

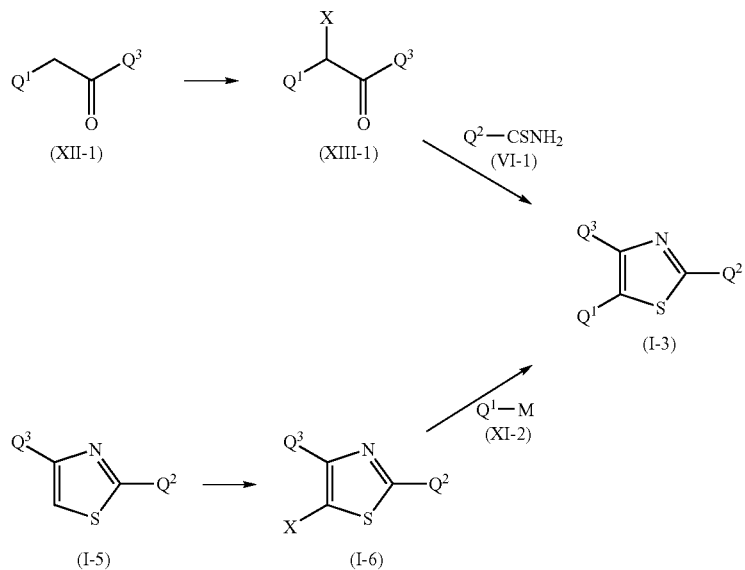

wherein each symbol is as defined above.

The compound (I-3) can be also obtained by condensation of compound (XIII-1) obtained from compound (XII-1) as a starting material with compound (VI-1) obtained by the aforementioned method. The compound (XII-1) can be synthesized according to the method of *Synthesis*, pp. 705–706 (1975) or *Journal of Chemical and Engineering Data*, vol. 19, pp. 392–393 (1974) or JP-A-5-345772. The compound (XIII-1) can be obtained from compound (XII-1) as a starting material according to the aforementioned method for obtaining compound (V-1) from compound (II-1). In addition, condensation of compound (XIII-1) and compound (VI-1) can be carried out according to condensation of compound (V-1) and compound (VI-1).

In addition, compound (I-3) can be also obtained by halogenation using compound (1–5), wherein the 5-position of thiazole ring is unsubstituted, which is obtained by the aforementioned method, as a starting material according to the method described in *Shin Jikken Kagaku Koza* (*New Courses in Experimental Chemistry*), vol. 14, p. 331 (Maruzen) to give compound (I-6), wherein the 5-position is halogenated, and substitution using compound (XI-2) according to the method used to give compound (I-1) from compound (VIII-1).

Production Method 4

The compound (I-4) can be produced by the reaction shown by the following formula.

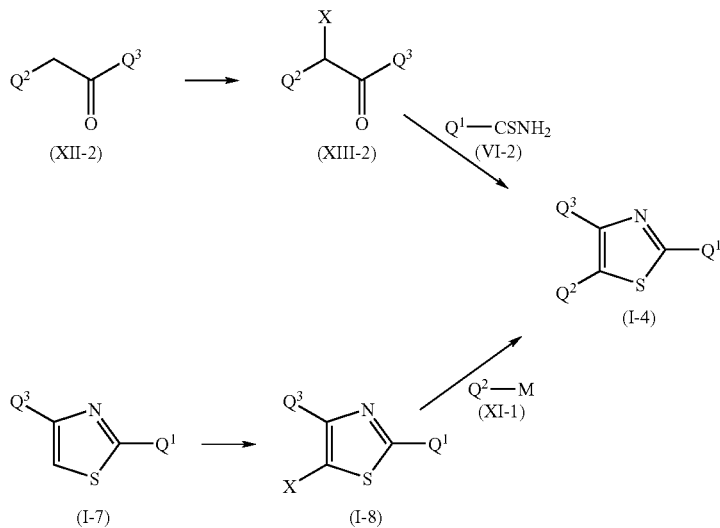

wherein each symbol is as defined above.

The compound (I-4) can be also obtained by condensation of compound (XIII-2) obtained from compound (XII-2) as a starting material with compound (VI-2) obtained by the aforementioned method. The compound (XII-2) can be synthesized according to the method of *Synthesis*, pp. 705–706 (1975) or *Journal of Chemical and Engineering Data*, vol. 19, pp. 392–393 (1974) or JP-A-5-345772. The compound (XIII-2) can be obtained from compound (XII-2) as a starting material according to the aforementioned method for obtaining compound (V-1) from compound (II-1). In addition, condensation of compound (XIII-2) and compound (VI-2) can be carried out according to condensation of compound (V-1) and compound (VI-1).

In addition, compound (I-4) can be also obtained by halogenation using compound (I-7), wherein the 5-position of thiazole ring is unsubstituted, which is obtained by the aforementioned method, as a starting material according to the method described in *Shin Jikken Kagaku Koza (New Courses in Experimental Chemistry)*, vol. 14, p. 331 (Maruzen) to give compound (I-8), wherein the 5-position is halogenated, and substitution using compound (XI-1) according to the method used to give compound (I-1) from compound (VIII-1).

When the objective product obtained by the above-mentioned reaction is a free form, it may be converted to a salt according to a conventional method, and when it is obtained as a salt, it may be converted to a free form or a different salt according to a conventional method. The compound (I) thus obtained can be isolated and purified from a reaction solution by a known means such as phase transfer, concentration, solvent extraction, fractional distillation, crystallization, recrystallization, chromatography and the like.

In each of the aforementioned reactions, when a starting compound contains amino, carboxy or hydroxy as a substituent, it may be protected by a group generally used in peptide chemistry and the like. The protecting group is removed as necessary after the reaction to give the object compound.

As the protecting group of amino, there are exemplified formyl, and $C_{1-6}$ alkyl-carbonyl (e.g., acetyl, propionyl etc.), phenylcarbonyl, $C_{1-6}$ alkyloxy-carbonyl (e.g., methoxycarbonyl, ethoxycarbonyl etc.), phenyloxycarbonyl, $C_{7-10}$ aralkyloxy-carbonyl (e.g., benzyloxycarbonyl etc.), trityl, phthaloyl and the like, all of which are optionally substituted. Examples of these substituents include halogen atom (e.g., fluorine, chlorine, bromine, iodine etc.), $C_{1-6}$ alkyl-carbonyl (e.g., acetyl, propionyl, valeryl etc.), nitro and the like, wherein the number of substituents is approximately 1 to 3.

As the protecting group of carboxy, there are exemplified $C_{1-6}$ alkyl (e.g., methyl, ethyl, propyl, isopropyl, butyl, tert-butyl etc.), phenyl, trityl, silyl and the like, all of which are optionally substituted. Examples of these substituents include halogen atom (e.g., fluorine, chlorine etc.), formyl, $C_{1-6}$ alkyl-carbonyl (e.g., acetyl, propionyl, butylcarbonyl etc.), nitro, $C_{1-6}$ alkyl (e.g., methyl, ethyl, tert-butyl etc.), $C_{6-10}$ aryl (e.g., phenyl, naphthyl etc.) and the like, wherein the number of substituents is approximately 1 to 3.

As the protecting group of hydroxy, there are exemplified $C_{1-6}$ alkyl (e.g., methyl, ethyl, propyl, isopropyl, butyl, tert-butyl etc.), phenyl, $C_{7-11}$ aralkyl (e.g., benzyl etc.), formyl, $C_{1-6}$ alkyl-carbonyl (e.g., acetyl, propionyl etc.), phenyloxycarbonyl, $C_{7-11}$ aralkyloxy-carbonyl (e.g., benzyloxycarbonyl etc.), tetrahydropyranyl, tetrahydrofuranyl or silyl and the like, all of which are optionally substituted. Examples of these substituents include halogen atom (e.g., fluorine, chlorine, bromine, iodine etc.), $C_{1-6}$ alkyl (e.g., methyl, ethyl, tert-butyl etc.), $C_{7-11}$ aralkyl (e.g., benzyl etc.), $C_{6-10}$ aryl (e.g., phenyl, naphthyl etc.), nitro and the like, wherein the number of substituents is approximately 1 to 4.

For removing the protecting group, a method known per se or a method analogous thereto is used. For example, a method comprising treatment with an acid, a base, ultraviolet radiation, hydrazine, phenylhydrazine, sodium N-methyldithiocarbamate, tetrabutyl ammonium fluoride, palladium acetate and the like or reduction reaction is used.

In any case, compound (I) can be synthesized by each of known deprotection, acylation reaction, alkylation reaction, hydrogenation reaction, oxidization reaction, reduction reaction, carbon chain extension reaction and substituent exchange reaction, where desired, alone or two or more thereof in combination. For these reactions, for example, the methods described in *Shin Jikken Kagaku Koza (New Courses in Experimental Chemistry)*, vol. 15 (1977), (Maruzen) are employed.

When the objective product obtained by the above-mentioned reaction is a free form, it may be converted to a salt according to a conventional method, and when it is obtained as a salt, it may be converted to a free form or a different salt according to a conventional method. The compound (I) thus obtained can be isolated and purified from a reaction solution by a known means such as phase transfer, concentration, solvent extraction, fractional distillation, crystallization, recrystallization, chromatography and the like.

When compound (I) is present as a configuration isomer, diastereomer, conformer and the like, it can be isolated as desired by the aforementioned separation and purification means. When compound (I) is a racemate, it can be separated into an S form and an R form by a general means for optical resolution.

When compound (I) has a steric isomer, such isomer alone and a mixture thereof are encompassed in the present invention.

The compound (I) may be a hydrate or a non-hydrate.

The compound (I) may be labeled with an isotope (e.g., $^3H$, $^{14}C$, $^{35}S$) and the like.

A prodrug of compound (I) is a compound which is converted into compound (I) as a result of a reaction with an enzyme, gastric acid etc. under physiological conditions in vivo. Thus, the compound is converted into compound (I) by enzymatical oxidation, reduction, hydrolysis etc., or by hydrolysis due to gastric acid etc. A prodrug of compound (I) may be a compound obtained by subjecting an amino group of compound (I) to an acylation, alkylation or phosphorylation (e.g., a compound obtained by subjecting an amino group of compound (I) to an eicosanoylation, alanylation, pentylaminocarbonylation, (5-methyl-2-oxo-1,3-dioxolen-4-yl)methoxycarbonylation, tetrahydrofuranylation, pivaloylmethylation, pivaloyloxymethylation, tert-butylation, etc.); a compound obtained by subjecting a hydroxy group in compound (I) to an acylation, alkylation, phosphorylation and boration (e.g., a compound obtained by subjecting a hydroxy group of compound (I) to an acetylation, palmitoylation, propanoylation, pivaloylation, succinylation, fumarylation, alanylation, dimethylaminomethylcarbonylation, etc.); a compound obtained by subjecting a carboxyl group of compound (I) to an esterification or amidation (e.g., a compound obtained by subjecting a carboxyl group of compound (I) to an ethyl-esterification, phenyl-esterification, carboxymethyl-esterification, dimethylaminomethyl-esterification, pivaloyloxymethyl-esterification, ethoxycarbonyloxyethyl-esterification, phthalidyl-esterification, (5-methyl-2-oxo-1,3-dioxolen-4-yl)methyl-esterification, cyclohexyloxycarbonylethyl-esterification and methylamidation, etc.) and the like. Any of these compounds can be produced from compound (I) by a method known per se.

A prodrug of compound (I) may also be one which is converted to compound (I) under physiological conditions, such as those described in "IYAKUHIN no KAIHATSU (Development of Pharmaceuticals)", Vol. 7, Design of Molecules, p. 163–198, Published by HIROKAWA SHOTEN (1990).

The compounds (I), (I-1), (I-2), (I-3), (I-4), (I-5), (I-6), (I-7), (I-8), (Ia), (Ia1), (Ia2), (Ia3), (Ia4), (Ib), (Ib1), (Ib2), (Ib3), (Ib4), (Ic1) and (Ic2) (hereinafter the both are also referred to as the compound of the present invention) provide a superior effect as a medicine and show a particularly superior steroid $C_{17,20}$-lyase-inhibitory activity. The compound of the present invention shows low toxicity and lower side effects. Therefore, they can be used for mammals (e.g., human, calf, horse, pig, dog, cat, monkey, mouse, rat etc., particularly human), are useful as, for example, (i) an androgen or estrogen reducing agent or (ii) an agent for the treatment or prevention of various diseases such as diseases related to androgen or estrogen, such as (1) primary cancer, metastasis or recurrence of malignant tumor (e.g., prostate cancer, breast cancer, uterine cancer, ovarian cancer etc.), (2) various symptoms accompanying the cancers (e.g., pain, cachexia etc.), and (3) sex hormone dependent diseases (e.g., prostatic hypertrophy, masculinism, hypertrichosis, male pattern baldness, male infant-type prematurity, endometriosis, hysteromyoma, adenomyosis of uterus, mastopathy, polycystic ovary syndrome etc.) and the like.

The compound of the present invention shows a superior effect even when used alone. When combined with a different pharmaceutical preparation or therapy, the effect can be reinforced furthermore. As the combination drug and therapy, for example, there are mentioned, but not limited to, "sex hormone agents (hormone preparation)", "alkylating agents", "antimetabolites", "carcinostatic antibiotics", "plant alkaloids", "immunotherapeutic agents", "pharmaceutical agents inhibiting action of cell growth factor and its receptor" and the like (hereinafter to be briefly referred to as a combination drug). Besides the combined use, the compound of the present invention and a different compound that provides preferable efficacy (specifically, various efficacies to be mentioned below) when combined with the compound may be contained in a single preparation to give a mixture.

Examples of the "hormone preparation" include fosfestrol, diethylstilbestrol, chlorotrianisene, medroxyprogesterone acetate, megesterol acetate, chlormadinone acetate, cyproterone acetate, danazol, allylestrenol, gestrinone, mepartricine, raloxifene, ormeloxifene, levormeloxifene, antiestrogen (e.g., tamoxifen citrate, toremifene citrate etc.), contraceptive pill, mepitiostane, testolactone, aminoglutethimide, LHRH receptor modulator [LH-RH receptor agonist (e.g., goserelin acetate, buserelin acetate, leuprorelin acetate etc.), LH-RH receptor antagonist (e.g., ganirelix, cetrorelix, abarelix etc.)], droloxifene, epitiostanol, ethinylestradiol sulfonate, aromatase inhibitor (e.g., fadrozole hydrochloride, anastrozole, letrozole, exemestane, vorozole, formestane etc.), antiandrogen (e.g., flutamide, bicalutamide, nilutamide etc.), 5α-reductase inhibitor (e.g., finasteride, episteride etc.), adrenocortical hormone preparation (e.g., cortisol, dexamethasone, prednisolone, betamethasone, triamcinolone etc.), androgen synthesis inhibitor (e.g., abiraterone etc.), retinoid and an agent to delay metabolism of retinoid (e.g., liarozole etc.) and the like.

Examples of the "alkylating agents" include nitrogen mustard, nitrogen mustard-n-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine phosphate sodium, triethylene melamine, carmustine, lomustine, streptozocin, pipobroman, etoglucide, carboplatin, cisplatin, miboplatin, nedaplatin, oxaliplatin, altretamin, ambamustine, dibrospidium hydrochloride, fotemustine, prednimustine, pumitepa, ribomustin, temozolomide, treosulfan, trophosphamide, zinostatin stimalamer, adozelesin, cystemstin, bizelesin and the like.

Examples of the "antimetabolites" include mercaptopurine, 6-mercaptopurine riboside, thioinosine, methotrexate, enocitabine, cytarabine, cytarabine ocphosphate, ancitabine hydrochloride, 5-FU pharmaceutical agents (e.g., fluorouracil, tegafur, UFT, doxifluridine, carmofur, galocitabine, emitefur etc.), aminopterin, calcium leucovorin, tabloid, butocin, calcium folinate, calcium levofolinate, cladribine, fludarabine, gemcitabine, hydroxycarbamide, pentostatin, piritrexim, idoxuridine, mitoguazone, tiazofurin and the like.

Examples of the "carcinostatic antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride and the like.

Examples of the "plant alkaloids" include etoposide, etoposide phosphate, vinblastine sulfate, vincristine sulfate, vindesine sulfate, teniposide, paclitaxel, vinorelbine and the like.

Examples of the "immunotherapeutic agents" (BRM) include picibanil, krestin, sizofiran, lentinan, ubenimex, interferon, interleukin, macrophage colony stimulating factor, granulocyte-colony stimulating factor, erythropoietin, lymphotoxin, BCG vaccine, *Corynebacterium parvum*, levamisole, polysaccharide K, procodazol and the like.

As the "cell growth factor" in the "pharmaceutical agents inhibiting action of the cell growth factor and its receptor", any substance can be used as long as it enhances proliferation of cells. In general, a factor which is a peptide having a molecular weight of not more than 20,000, and which can show effect upon binding with receptor at a low concentration is exemplified. Specific examples include (1) EGF (epidermal growth factor) or a substance having substantially the same activity therewith [e.g., EGF, heregulin (HER2 ligand) etc.], (2) insulin or a substance having substantially the same activity therewith [e.g., insulin, IGF (insulin-like growth factor)-1, IGF-2 etc.], (3) FGF (fibroblast growth factor) or a substance having substantially the same activity therewith [e.g., acidic FGF, basic FGF, KGF (keratinocyte growth factor), FGF-10 etc.], (4) other cell growth factors [e.g., CSF (colony stimulating factor), EPO (erythropoietin), IL-2(interleukin-2), NGF (nerve growth factor), PDGF (platelet-derived growth factor), TGFβ (transforming growth factor β), HGF (hepatocyte growth factor), VEGF (vascular endothelial growth factor) etc.] and the like.

The "receptor of the cell growth factor" may be any receptor as long as it has a binding ability with the above-mentioned cell growth factor. Specific examples include EGF receptor, HER2 (heregulin receptor), insulin receptor, IGF receptor, FGF receptor-1, FGF receptor-2 and the like.

Examples of the "pharmaceutical agents inhibiting action of the cell growth factor" include antibodies against cell growth factor and receptor thereof, such as EGF receptor antibody (e.g., cetuximab) and HER2 antibody (e.g., herceptin); tyrosine kinase inhibitors such as Iressa (EGF receptor tyrosine kinase inhibitor), TAK-165 (HER2 tyrosine kinase inhibitor), GW2016 (EGF receptor/HER2 tyrosine kinase inhibitor) and the like; ribozyme that inhibits expression of cell growth factor and receptor thereof; antisense medicaments and the like.

In addition to the aforementioned pharmaceutical agents, L-asparaginase, aceglatone, procarbazine hydrochloride, cobalt protoporphyrin complex, mercurial hematoporphyrin sodium, topoisomerase I inhibitor (e.g., irinotecan, topotecan etc.), topoisomerase II inhibitor (e.g., sobuzoxane etc.), differentiation inducing agent (e.g., retinoid, vitamine D etc.), angiogenesis inhibitor, α-blocker (e.g., tamsulosin hydrochloride etc.) and the like can be also used.

Along with a chemical therapy to administer the compound of the present invention, for example, a therapy other than the chemical therapy such as an operation including orchiectomy, thermotherapy, radiation therapy and the like can be applied in combination.

Particularly, the compound of the present invention can more effectively remove androgen or estrogen in blood when used in combination with an LHRH receptor modulator (LHRH modulator) such as LHRH receptor agonist (e.g., goserelin acetate, buserelin acetate, leuprorelin acetate etc.) and LHRH receptor antagonist (e.g., ganirelix, cetrorelix, abarelix etc.).

The compound of the present invention has high selectivity to steroid $C_{17,20}$-lyase and shows less influence on drug metabolizing enzymes, such as CYP3A4. Since influence on drug metabolizing enzymes (e.g., CYP3A4) is small, it serves well as a safe pharmaceutical agent with less limitation on combined drug.

For combined use of compound (I) and combination drug, the administration time of compound (I) and combination drug is not limited, and compound (I) and combination drug may be simultaneously administered to the administration objects or administered with time lag. The dose of the combination drug may be similar to that clinically employed, which can be determined as appropriate depending on the administration objects, administration route, disease, combination and the like.

The mode of administration of compound (I) and combination drug is not particularly limited, and compound (I) and combination drug only need to be combined on administration. Such administration mode is exemplified by (1) administration of a single pharmaceutical preparation obtained by simultaneous formulation of compound (I) and combination drug, (2) simultaneous administration of two kinds of pharmaceutical preparations obtained by separate formulation of compound (I) and combination drug by the same administration route, (3) time lag administration of two kinds of pharmaceutical preparations obtained by separate formulation of compound (I) and combination drug by the same administration route, (4) simultaneous administration of two kinds of pharmaceutical preparations obtained by separate formulation of compound (I) and combination drug by different administration routes, (5) time lag administration of two kinds of pharmaceutical preparations obtained by separate formulation of compound (I) and combination drug by different administration routes (e.g., administration of compound (I) → combination drug and administration in reverse order) and the like.

As the pharmaceutically acceptable carrier, various organic and inorganic carrier substances for conventional production material are used and appropriately added as an excipient, a lubricant, a binder, a disintegrating agent and a thickener to solid preparations; as a solvent, a dispersing agent, a solubilizer, a suspending agent, an isotonicity agent, a buffer and a soothing agent to liquid preparations, and the like. Where necessary, additives such as an antiseptic, an antioxidant, a coloring agent, a sweetener and the like can be used according to a conventional method. Preferable examples of the excipient include lactose, sucrose, D-mannitol, starch, crystalline cellulose, light anhydrous silicic acid and the like. Preferable examples of the lubricant include magnesium stearate, calcium stearate, talc, colloidal silica and the like. Preferable examples of the binder include crystalline cellulose, sucrose, D-mannitol, dextrin, hydroxypropylcellulose, hydroxypropylmethylcellulose, polyvinylpyrrolidone and the like. Preferable examples of the disintegrating agent include starch, carboxymethyl cellulose, carboxymethyl cellulose calcium, crosscarmellose sodium, sodium carboxym ethyl starch and the like. Preferable examples of the thickener include natural gums, cellulose derivative, acrylate polymer and the like. Preferable examples of the solvent include water for injection, alcohol, propylene glycol, Macrogol, sesame oil, corn oil and the like. Preferable examples of the dispersing agent include Tween 80, HCO 60, polyethylene glycol, carboxymethyl cellulose, alginate sodium and the like. Preferable examples of the solubilizer include polyethylene glycol, propylene glycol, D-mannitol, benzyl benzoate, ethanol, tris-aminomethane, cholesterol, triethanolamine, sodium carbonate, sodium citrate and the like. Preferable examples of the suspending agent include surfactants such as stearyl triethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, carboxymethylcellulose sodium, methylcellulose, hydroxymethylcellulose, hydroxyethyl cellulose, hydroxypropylcellulose etc., and the like. Preferable examples of the isotonicity agent include sodium chloride, glycerine, D-mannitol and the like. Preferable examples of the buffer include buffer solutions of phosphate, acetate, carbonate, citrate and the like. Preferable examples of the soothing agent include benzyl alcohol and the like. Preferable examples of the antiseptic include p-hydroxybenzoic acid esters, chlorobutanol, benzyl alcohol, phenethyl alcohol, dehydroacetic acid, sorbic acid and the like. Preferable examples of the antioxidant include sulfite, ascorbic acid and the like.

The pharmaceutical preparation of the present invention can be produced according to a conventional method, wherein the content of the compound of the present invention in the preparation is generally 0.1–100% (w/w). Specific examples are shown in the following.

(1) Tablet, Powder, Granule, Capsule:

These can be produced by adding, for example, an excipient, a disintegrating agent, a binder, a lubricant and the like to the compound of the present invention, and subjecting the mixture to compression molding, and where necessary, coating for masking of taste, enteric coating or coating for sustained release.

(2) Injection:

An injection can be produced by preparing the compound of the present invention into an aqueous injection together with, for example, a dispersing agent, a preservative, an isotonicity agent and the like, or dissolving, suspending or emulsifying in vegetable oil, such as olive oil, sesame oil, cottonseed oil, corn oil etc., propylene glycol and the like, to give an oily injection.

(3) Suppository:

A suppository can be produced by making the compound of the present invention into an oily or aqueous solid, semisolid or liquid composition. Examples of the oily base to be used for such a composition include glyceride of higher fatty acid (e.g., cacao butter, Witepsol etc.), medium fatty acid (e.g., migliol etc.), vegetable oil (e.g., sesame oil, soybean oil, cottonseed oil etc.) and the like. Examples of the aqueous gel base include natural gums, cellulose derivative, vinyl polymer, acrylate polymer and the like.

While the content of the compound of the present invention in these preparations varies depending on the kind of preparation, it is generally 0.01–50%.

The amount of the compound of the present invention to be used in the aforementioned pharmaceutical preparation varies depending on the compound to be selected, animal species selected to be the administration object, frequency of administration and the like. The compound exerts effectiveness over a wide range of dosages. For example, the daily dose of a pharmaceutical preparation of the present invention when orally administered to an adult patient with solid tumor (e.g., patient with prostate cancer), as expressed in the effective amount of the compound of the present invention, is generally about 0.00 1 to about 500 mg/kg body weight, preferably about 0.1 to about 40 mg/kg body weight, more preferably about 0.5 to about 20 mg/kg body weight. When it is used for parenteral administration in combination with a different anticancer agent, the dose is generally smaller than the doses mentioned above. However, the amount of the compound actually administered is determined based on the selection of the compound, dosage form, age, body weight and sex of the patient, level of disease state, administration route, the period and intervals of the administration and the like, and can be modified at any time according to the judgment of doctors.

While the administration route of the aforementioned pharmaceutical preparation is not particularly limited by various conditions, for example, it can be administered orally or parenterally. As used herein, by the "parenteral" is meant intravenous, intramuscular, subcutaneous, intranasal, intracutaneous, instillation, intracranial, endorectal, intravaginal and intraperitoneal administrations.

The period and intervals of the administration of the aforementioned pharmaceutical preparation are modified according to various conditions and determined according to the judgment of doctors at any time. The administration method includes, for example, divisional administration, consecutive daily administration, intermittent administration, administration in large amounts in a short term, repeat administration and the like. In the case of oral administration, for example, the preparation is desirably administered once a day to several times a day (particularly 2 or 3 times a day) by dividing the dose. It is also possible to administer as a sustained release preparation or intravenous infusion over a long time.

The present invention is explained in more detail by way of the following Reference Examples and Examples. These Examples are mere embodiments and do not limit the present invention in any way and can be modified as long as they do not deviate from the scope of the present invention. In the following Reference Examples and Examples, silica gel 60 (70–230 or 230–400 mesh) manufactured by Merck was used as the filler for column chromatography. The melting point was measured using Yanaco MP-J3. $^1$H NMR spectrum was measured in Varian Gemini-200 (200 MHz) or MERCURY (300 MHz) using tetramethylsilane as the internal standard. The symbols in the Examples mean the following and abbreviations in the Examples mean the following.

s: singlet, d: doublet, t: triplet, q: quartet, dd: double doublet, dt: double triplet, m: multiplet, br: broad, J: coupling constant, room temperature: 20–30° C., DMF: dimethylformamide, THF: tetrahydrofuran.

RERERENCE EXAMPLE 1

(2',4'-dimethyl)phenyl-2-bromoacetophenone (1)

(2',4'-Dimethyl)-2-acetophenone (14.8 g, 100 mmol) was dissolved in ethyl acetate (200 ml) and copper bromide (45.0 g, 200 ml) was added. The mixture was heated under reflux for 3 hrs. After cooling, solid was filtered off. The filtrate was concentrated under reduced pressure and the residue was purified by silica gel column chromatography, which was then converted to a powder from isopropyl ether to give the title compound (11.9 g, 52%).

elemental analysis for $C_{10}H_{11}OBr$

|  | C (%) | H (%) |
| --- | --- | --- |
| Calculated: | 52.89; | 4.88 |
| Found: | 52.69; | 4.90 |

$^1$H-NMR (200 Hz, CDCl$_3$) δ: 2.37(3H, s), 2.52 (3H, s), 4.42 (2H, s), 7.09 (1H, d, J=7.0 Hz), 7.11(1H, s), 7.62 (1H, d, J=7.0 Hz).

RERERENCE EXAMPLE 2

Examples of the compounds produced according to the method described in Reference Example 1 using commercially available acetylbenzene derivative or acetylpyridine derivative as a starting material are shown in Table 1.

TABLE 1

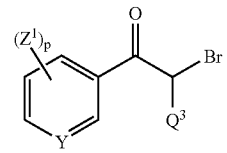

| Comp. No. | $(Z^1)_p$ | $Q^3$ | Y | yield (%) | melting point: (° C.) |
| --- | --- | --- | --- | --- | --- |
| 1 | 2,4-dimethyl | hydrogen | C | 52 | 36–38 |
| 2 | 2-hydroxy | hydrogen | C | 65 | 40–42 |
| 3 | 4-hydroxy | hydrogen | C | 100 | 124–126 |
| 4 | 3,4-dimethyl | hydrogen | C | 59 | 56 |
| 5 | 2,4-difluoro | hydrogen | C | 90 | oil |
| 6 | 2,4-bistrifluoromethyl | hydrogen | C | 94 | 50–52 |
| 7 | 4-trifluoromethyl | hydrogen | C | 86 | 56–57 |
| 8 | hydrogen | methyl | C | 93 | liq. |
| 9 | 4-fluoro | methyl | C | 76 | liq. |
| 10 | 2-fluoro | methyl | C | 88 | liq. |

REFERENCE EXAMPLE 3

4'-(dibenzylsulfamoyl)-2-bromoacetophenone (11)

4.-(Dibenzylsulfamoyl)acetophenone (1.89 g, 5.0 mmol) prepared from 4-acetylbenzenesulfonic acid according to the method described in *J. Med. Chem.*, 43, 214–223 (2000) was dissolved in chloroform (10 ml) and a solution of bromine (0.80 g, 5.0 mmol) dissolved in chloroform (5 ml) was added dropwise at room temperature over 10 min., and the mixture was stirred for 40 min. Chloroform was concentrated under reduced pressure, and recrystallized from a small amount of diethyl ether to give the title compound (1.92 g, 86%).

elemental analysis for $C_{21}H_{21}NO_3SBr$

|  | C (%) | H (%) | N (%) |
|---|---|---|---|
| Calculated: | 56.38; | 4.73; | 3.13 |
| Found: | 56.61; | 4.85; | 3.40 |

$^1$H-NMR (200 Hz, $CDCl_3$) δ: 4.38 (4H, s), 4.46 (2H, s), 7.03–7.27 (10H, m).

REFERENCE EXAMPLE 4

Examples of the compounds produced according to the method described in Reference Example 3 using commercially available acetylbenzene derivative or acetylpyridine derivative as a starting material are shown in Table 2.

TABLE 2

| Comp. No. | $(Z^1)_p$ | $Q^3$ | Y | yield (%) | melting point: (° C.) |
|---|---|---|---|---|---|
| 11 | 4-dibenzylsulfamoyl | hydrogen | C | 86 | 89 |
| 12 | 4-methylsulfonyl | hydrogen | C | 90 | 126 |
| 13 | 4-methylsulfamoyl | hydrogen | C | 74 | 140 |

REFERENCE EXAMPLE 5

4-methylnicotinonitrile (14)

Referring to JP-A-7-10841, 2,6-dichloro-4-methylnicotinonitrile (manufactured by Mabridge) (17.0 g, 90.9 mmol) was dissolved in methanol (450 ml), and 10% Pd—C (1.7 g, 10 wt. %) and sodium acetate (15.2 g, 186 mmol) were added. The mixture was stirred at room temperature under hydrogen pressure for 16 hrs. and the catalyst and the like were filtered off. The solvent was concentrated under reduced pressure, and the resulting mixture was partitioned between dichloromethane (300 ml)-5% aqueous sodium hydrogen carbonate (200 ml). The organic layer was dried and the resulting mixture was concentrated under reduced pressure. Recrystallization from a small amount of isopropyl ether gave the title compound (9.2 g, 86%).

sublimability elemental analysis for $C_7H_6N_2$

|  | C (%) | H (%) | N (%) |
|---|---|---|---|
| Calculated: | 71.17; | 5.12; | 23.71 |
| Found: | 71.19; | 5.40; | 23.88 |

$^1$H-NMR (200 Hz, $CDCl_3$) δ: 2.58 (3H, s), 7.31 (1H, d, J=5.8 Hz), 8.66 (1H, d, J=5.8 Hz), 8.80 (1H, s).

REFERENCE EXAMPLE 6

3-acetyl-4-methylpyridine (15)

To a solution of compound (14)(2.0 g, 16.9 mmol) in ether (13 ml) was added a methylmagnesium iodide-ether solution (18.2 ml, 27.4 mmol) under ice-cooling. The reaction mixture was heated to 50° C. and stirred overnight. The reaction mixture was again ice-cooled and 5% hydrochloric acid (400 ml) was added. The reaction mixture was neutralized with a 1N aqueous sodium hydroxide solution and extracted with ethyl acetate. The extract was combined and dried ($MgSO_4$) and the solvent was evaporated under reduced pressure. The obtained residue was purified by silica gel column chromatography to give a yellow oil (1.26 g, 55%).

$^1$H-NMR (200 Hz, $CDCl_3$) δ: 2.57 (3H, s), 2.65 (3H, s), 7.20 (1H, d, J=5.2 Hz), 8.55 (1H, d, J=5.2 Hz), 8.95 (1H, s).

RERERENCE EXAMPLE 7

3-(2-bromoacetyl)pyridine Hydrobromate (16)

To a solution of 3-acetylpyridine (5.00 g, 41.3 mmol) in acetic acid (100 ml) was added 47% hydrobromic acid (7.10 ml, 41.3 mmol), and a solution of bromine (2.12 ml, 41.3 mmol) in acetic acid (50 ml) was added dropwise under ice-cooling. After the completion of the dropwise addition, the reaction mixture was heated to 80° C. and the mixture was stirred for one hr. After cooling, the precipitated crystals were collected by filtration, washed with ethanol-ethyl acetate and dried under reduced pressure to give white crystals.

melting point: 228° C.

$^1$H-NMR (200 Hz, $DMSO-d_6$) δ: 5.08 (2H, s), 7.93 (1H, dd, J=8.0 Hz, 5.6 Hz), 8.69 (1H, d, J=8.0 Hz), 8.99 (1H, d, J=5.6 Hz), 9.33 (1H, s).

REFERENCE EXAMPLE 8

Examples of the compounds produced according to the method described in Reference Example 7 using compound (15) and 3-propionylpyridine as starting materials are shown in Table 3.

TABLE 3

| Comp. No. | $Q^2$ | $Q^3$ | yield (%) | melting point: (° C.) |
|---|---|---|---|---|
| 17 | 3-(4-methylpyridyl) | hydrogen | 70 | amorphous |
| 18 | 3-pyridyl | methyl | 80 | 148–150 |

REFERENCE EXAMPLE 9

4-chloronicotinaldehyde (19)

A solution (50 ml) of 4-chloropyridine (25.0 g, 0.22 mol) in tetrahydrofuran was added dropwise to a tetrahydrofuran solution (300 ml) of lithium diisopropylamide prepared from a solution (179 ml, 0.29 mol) of 1.6 M n-butyllithium in hexane and diisopropylamine (33.4 g, 0.33 mol) under an argon atmosphere at −78° C. After stirring for 30 min., DMF (19.3 g, 0.26 mol) was added and the mixture was gradually heated to room temperature. The reaction mixture was extracted with ethyl acetate (200 ml)-5% $NH_4Cl$ aq. (300 ml). The organic layer was dried ($MgSO_4$) and the solvent was evaporated under reduced pressure to give a crude title compound (27 g, 86%) as an oil.

$^1$H-NMR (200 Hz, $CDCl_3$) δ: 7.45 (1H, d, J=5.0 Hz), 8.69 (1H, d, J=5.0 Hz), 9.05 (1H, s), 10.51 (1H, s).

REFERENCE EXAMPLE 10

4-chloronicotinonitrile (20)

The compound (19) (27.0 g, 0.19 mol), hydroxylamine hydrochloride (13.01 g, 0.19 mol) and sodium acetate (15.6 g, 0.19 mol) were suspended in methanol (100 ml) and the mixture was stirred at room temperature for 2 hrs. The solvent was evaporated and the residue was dissolved in chloroform (100 ml). Phosphorus oxychloride (125 g) was added and the mixture was heated under ref lux for 3 hrs. The solvent was evaporated and the residue was added to water (200 ml), which was adjusted to pH=7 with sodium carbonate. The mixture was extracted with ethyl acetate (200 ml×2) and the organic layer was dried ($MgSO_4$). The solvent was evaporated under reduced pressure to give the title compound (18 g, 68%).

$^1$H-NMR (200 Hz, $CDCl_3$) δ: 7.52 (1H, d, J=5.0 Hz), 8.72 (1H, d, J=5.0 Hz), 8.87 (1H, s).

REFERENCE EXAMPLE 11

4-methoxynicotinonitrile (21)

To a solution of compound (20)(2.77 g, 20.0 mmol) in methanol (5 ml) was added a 28% sodium methylate-methanol solution (5.0 g, 24.0 mmol) at room temperature and the mixture was stirred for one hr. The solvent was concentrated and the obtained residue was partitioned between ethyl acetate and iced-brine. The organic layer was dried over anhydrous magnesium sulfate and the solvent was evaporated under reduced pressure. The obtained residue was recrystallized from a small amount of isopropyl ether to give the title compound (2.3 g, 86%).

elemental analysis for $C_7H_8N_2O$

|  | C (%) | H (%) | N (%) |
|---|---|---|---|
| Calculated: | 62.68; | 4.51; | 20.88 |
| Found: | 62.74; | 4.69; | 20.59 |

$^1$H-NMR (200 Hz, $CDCl_3$) δ: 4.02 (3H, s), 6.93 (1H, d, J=5.8 Hz), 8.65 (1H, d, J=5.8 Hz), 8.69 (1H, s).

REFERENCE EXAMPLE 12

Examples of the compounds produced according to the method described in Reference Example 11 using compound (20) as a starting material are shown in Table 4.

TABLE 4

| Comp. No. | $(Z^1)_p$ | Y | yield (%) | melting point: (° C.) |
|---|---|---|---|---|
| 21 | 4-methoxy | N | 86 | 110–112 |
| 22 | 4-isopropoxy | N | 90 | 48 |
| 23 | 4-dimethylamino | N | 90 | 82–83 |
| 24 | 4-methylthio | N | 90 | amorphous |

REFERENCE EXAMPLE 13

4-vinylnicotinonitrile (25)

To a solution of compound (20)(1.00 g, 7.21 mmol) in dimethylformamide (15 ml) were added tributyl(vinyl)tin (2.50 ml, 8.65 mmol) and dichlorobis(triphenylphosphine) palladium (0.40 g, 0.58 mmol), and the mixture was stirred at 120° C. under an argon atmosphere for one hr. The reaction mixture was poured into ice water and extracted with ethyl acetate. The extract was combined and washed with brine and dried ($MgSO_4$). The solvent was evaporated under reduced pressure and the obtained residue was purified by silica gel column chromatography to give a white powder (0.93 g, 99%).

melting point: 56–57° C.

$^1$H-NMR (200 Hz, $CDCl_3$) δ: 5.80 (1H, d, J=11.0 Hz), 6.21 (1H, d, J=17.6 Hz), 7.02 (1H, dd, J=11.0 Hz, 17.6 Hz), 7.54 (1H, d, J=5.6 Hz), 8.73 (1H, d, J=5.6 Hz), 8.85 (1H, s).

REFERENCE EXAMPLE 14

4-ethylnicotinonitrile (26)

The compound (25) (0.73 g, 5.61 mmol) was dissolved in ethyl acetate (15 ml) and 10% palladium carbon (20 mg) was added. The mixture was stirred at normal temperature and normal pressure under a hydrogen atmosphere for 2 hrs. for hydrogenation. The reaction mixture was passed through celite and the filtrate was partitioned between ethyl acetate and brine. The aqueous layer was extracted with ethyl acetate, and the extract was combined and dried ($MgSO_4$). The solvent was evaporated under reduced pressure. The obtained residue was purified by silica gel column chromatography to give a colorless oil (0.62 g, 84%).

$^1$H-NMR (200 Hz, $CDCl_3$) δ: 1.34 (3H, t, J=7.6 Hz), 2.89 (2H, q, J=7.6 Hz), 7.30 (1H, d, J=5.6 Hz), 8.68 (1H, d, J=5.6 Hz), 8.80 (1H, s).

REFERENCE EXAMPLE 15

4-methylpyridine-3-carbothioamide (27)

To a solution of compound (14)(9.2 g, 77.9 mmol) in dimethylformamide (500 ml) was added triethylamine (800 mg, 7.79 mmol; 10 mol %), and the mixture was stirred at room temperature for 16 hrs. while introducing hydrogen sulfide gas. The solvent was concentrated and the obtained residue was partitioned between dichloromethane and brine. The aqueous layer was extracted with dichloromethane. The extracts were combined and dried over anhydrous magnesium sulfate. The solvent was evaporated under reduced pressure and the obtained residue was recrystallized from a small amount of ethyl acetate to give the title compound (10.2 g, 86%).

elemental analysis for $C_7H_8N_2S$

|  | C (%) | H (%) | N (%) |
|---|---|---|---|
| Calculated: | 55.24; | 5.30; | 18.40 |
| Found: | 55.38; | 5.42; | 18.43 |

$^1$H-NMR (200 Hz, CDCl$_3$) δ: 2.49(3H, s), 7.13 (1H, d, J=5.2 Hz), 7.28 (1H, brs), 7.86 (1H, brs), 8.39 (1H, d, J=5.2 Hz), 8.49(1H, s).

REFERENCE EXAMPLE 16

Examples of the compounds produced according to the method described in Reference Example 15 using commercially available or synthesized nicotinonitrile derivative (compounds (21–24), (26)), or commercially available cyanobenzene derivative as a starting material are shown in Table 5.

TABLE 5

$H_2N—SC$ — [structure with $(Z^1)_p$ and Y]

| Comp. No. | $(Z^1)_p$ | Y | yield (° C.) | melting point: (° C.) |
|---|---|---|---|---|
| 27 | 4-methyl | N | 86 | 106–108 |
| 28 | 4-methoxy | N | 41 | 155–157 |
| 29 | 4-isopropoxy | N | 51 | 115 |
| 30 | 4-dimethylamino | N | 44 | 140–143 |
| 31 | 4-methylthio | N | 69 | 180–182 |
| 32 | 4-ethyl | N | 100 | 149–150 |
| 33 | 4-hydroxy | C | 53 | 195–196 |
| 34 | 2,4-difluoro | C | 36 | 127–129 |
| 35 | 2-chloro | C | 11 | amorphous |
| 36 | 3,4-butadienylene | N | 59 | 205–207 |
| 37 | 3-sulfamoyl | C | 36 | 127–129 |
| 38 | 4-fluoro | C | 22 | 151–152 |
| 39 | 4-sulfamoyl | C | 71 | amorphous |

REFERENCE EXAMPLE 17

4-chlorophenylacetyl thiocyanate (40)

4-Chlorophenylacetyl bromide (12.2 g, 52.3 mmol) was suspended in ethanol (50 ml) and heated to 60° C.–70° C. An aqueous solution (10 ml) of KSCN (5.59 g, 57.5 mmol) was added by small portions, and after addition, the mixture was stirred at 80° C. for 10 min. The reaction mixture was left standing at room temperature for 4 hrs. Water (150 ml) was added and the precipitated solid was collected by filtration. The residue was washed twice with water (150 ml) and dried under reduced pressure to give the title compound (10.1 g, 91%).

REFERENCE EXAMPLE 18

4-(4-chlorophenyl)-2-bromo-1,3-thiazole (41)

The compound (40) (2.1 g, 10.0 mmol) was suspended in acetic acid (10 ml) and 47% HBr-acetic acid (1 ml) was added. The mixture was stirred with heating at 80° C. for 2 hrs. The reaction mixture was concentrated under reduced pressure to dryness and the residue was partitioned between ethyl acetate and 5% NaHCO$_3$ aq. The aqueous layer was extracted with ethyl acetate, and the extracts were combined, washed with saturated brine and dried (MgSO$_4$). The solvent was evaporated under reduced pressure and isopropyl ether was added to the obtained residue, which was filtrated to give the title compound (1.2 g, 44%).

$^1$H-NMR (200 Hz, CDCl$_3$) δ: 7.39 (2H, d, J=8.8 Hz), 7.41 (1H, s), 7.80 (1H, d, J=5.6 Hz).

REFERENCE EXAMPLE 19

4-(4-chlorophenyl)-2-oxo-1,3-thiazole (42)

The compound (40)(10.9 mg, 52.2 mmol) was suspended in acetic acid (50 ml) and 50% sulfuric acid (15 ml) was added dropwise at 60° C. The mixture was heated under reflux for 2 hrs. After cooling, the reaction mixture added to ice (200 g). The precipitated crystals were collected by filtration, washed twice with water (200 ml) and dried under reduced pressure to give the title compound (10.1 g, 91%).

melting point: 230–233° C.

$^1$H-NMR (200 Hz, CDCl$_3$) δ: 6.28 (1H, s), 7.37 (2H, d, J=7.0 Hz), 7.52 (2H, d, J=7.0 Hz), 11.46 (1H, brs).

REFERENCE EXAMPLE 20

4-(4-chlorophenyl)-[2-(4-chloropyridin-3-yl)]-1,3-thiazole (43)

According to the synthetic example of compound (19), 4-chloropyridine (1.14 g, 10.0 mmol) and LDA (12 mmol) were reacted and ZnCl$_2$ (1.63 g, 12.0 mmol) was added to the obtained the reaction mixture. The mixture was stirred at −78° C. for 10 min. and compound (41) (548 mg, 2.0 mmol) and tetrakistriphenylphosphinepalladium (580 mg, 0.5 mmol) were added. The mixture was stirred at room temperature for 30 hrs. The reaction mixture was partitioned between ethyl acetate and NH$_4$Cl aq., and the ethyl acetate layer was washed once with NH$_4$Cl aq. The extract was dried (MgSO$_4$) and the solvent was evaporated under reduced pressure. The obtained residue was purified by silica gel column chromatography to give the title compound (250 mg, 40%).

melting point: 149–150° C.

$^1$H-NMR (200 Hz, CDCl$_3$) δ: 7.17 (1H, s), 7.49 (2H, d, J=8.0 Hz), 7.63–7.67 (1H, m), 7.84 (2H, d, J=8.0 Hz), 8.59 (1H, d, J=6.0 Hz), 9.11 (1H, s).

EXAMPLE 1

4-(2,4-dimethylphenyl)-[2-(4-methylpyridin-3-yl)]-1,3-thiazole monohydrochloride (44)

A mixture of compound (1) (227 mg, 1.0 mmol), compound (27) (152 mg, 1.0 mmol) and ethanol (3 ml) was heated under reflux for 6 hrs. After cooling, the solvent was evaporated under reduced pressure, and the obtained residue was partitioned between ethyl acetate and saturated aqueous sodium hydrogen carbonate. The organic layer was dried (MgSO$_4$) and the solvent was evaporated under reduced pressure. The residue was recrystallized from 4N hydrochloric acid/ethyl acetate to give crystals (220 mg, 69%) of monohydrochloride.

melting point: 148–150° C.

$^1$H-NMR (200 Hz, CDCl$_3$) δ: 2.33 (3H, s), 2.47 (3H, s), 2.83 (3H, s), 7.10–7.17 (2H, m), 7.59 (1H, d, J=7.6 Hz), 7.96 (1H, d, J=5.8 Hz), 8.10(1H, s), 8.79 (1H, d, J=5.8 Hz), 9.22 (1H, s).

EXAMPLE 2

Examples of the compounds produced according to the method described in Reference Example 1 using commercially available or synthesized α-bromoketone derivatives (compounds (1–13), (16–18)) and commercially available or synthesized thioacetamide derivatives (compounds (27–39)) as starting materials are shown in Table 6 to Table 12.

TABLE 6

| Comp. No. | $(Z^1)_p$ | $Q^3$ | $(Z^2)_q$ | $Y^1$ | $Y^2$ | salt | yield (%) | melting point: (° C.) |
|---|---|---|---|---|---|---|---|---|
| 45 | 4-phenyl | hydrogen | hydrogen | C | N | HBr | 82 | 238–241 |
| 46 | 4-nitro | hydrogen | hydrogen | C | N | HBr | 92 | 267–271 |
| 47 | 4-bromo | hydrogen | hydrogen | C | N | HBr | 71 | 213–216 |
| 48 | 3-nitro | hydrogen | hydrogen | C | N | HBr | 91 | 238–241 |
| 49 | 3-methoxy | hydrogen | hydrogen | C | N | HBr | 83 | 231–233 |
| 50 | 2-methoxy | hydrogen | hydrogen | C | N | HBr | 81 | 242–243 |
| 51 | 2,4-dimethoxy | hydrogen | hydrogen | C | N | HBr | 70 | 224–225 |
| 52 | 4-phenyl | hydrogen | 4-trifluoromethyl | C | N |  | 83 | 94–95 |
| 53 | 4-bromo | hydrogen | 4-trifluoromethyl | C | N |  | 93 | 69–71 |
| 54 | 2,5-dimethoxy | hydrogen | hydrogen | C | N | HBr | 79 | 223–226 |
| 55 | 4-diethylamino | hydrogen | hydrogen | C | N |  | 65 | 76–77 |
| 56 | 2,4-dimethyl | hydrogen | hydrogen | C | N | HCl | 78 | 152 |
| 57 | 2,4-dimethyl | hydrogen | 4-trifluoromethyl | C | N | HBr | 33 | 152 |
| 58 | 4-fluoro | hydrogen | 4-trifluoromethyl | C | N |  | 81 | 52–53 |

TABLE 7

| Comp. No. | $(Z^1)_p$ | $Q^3$ | $(Z^2)_q$ | $Y^1$ | $Y^2$ | salt | yield (%) | melting point: (° C.) |
|---|---|---|---|---|---|---|---|---|
| 59 | 4-nitro | hydrogen | 4-trifluoromethyl | C | N | HBr | 80 | 165–167 |
| 60 | 3-nitro | hydrogen | 4-trifluoromethyl | C | N | HBr | 70 | 178–183 |
| 61 | 3-methoxy | hydrogen | 4-trifluoromethyl | C | N | HBr | 70 | 140–145 |
| 62 | 2-methoxy | hydrogen | 4-trifluoromethyl | C | N | HBr | 42 | 176–180 |
| 63 | 4-methyl | hydrogen | 4-trifluoromethyl | C | N | HBr | 58 | 184 |
| 64 | 4-methoxy | hydrogen | 4-trifluoromethyl | C | N | HCl | 40 | 93–95 |
| 65 | 3-chloro | hydrogen | 4-trifluoromethyl | C | N | HBr | 65 | 140–143 |
| 66 | 2-chloro | hydrogen | 4-trifluoromethyl | C | N | HCl | 82 | 87–90 |
| 67 | 3,4-dimethyl | hydrogen | 4-trifluoromethyl | C | N | HBr | 47 | 123 |
| 68 | 4-hydroxy | hydrogen | 4-trifluoromethyl | C | N |  | 40 | 117–119 |
| 69 | 4-ethoxycarbonyl | hydrogen | 4-trifluoromethyl | C | N | HBr | 69 | 168–170 |
| 70 | 4-diethylamino | hydrogen | 4-trifluoromethyl | C | N | HCl | 91 | 105–110 |
| 71 | 3-methylcarbamoyl | hydrogen | 4-trifluoromethyl | C | N |  | 89 | 132–133 |

TABLE 8

| Comp. No. | $(Z^1)_p$ | $Q^3$ | $(Z^2)_q$ | $Y^1$ | $Y^2$ | salt | yield (%) | melting point: (° C.) |
|---|---|---|---|---|---|---|---|---|
| 72 | 4-trifluoromethyl | hydrogen | 4-trifluoromethyl | C | N | HBr | 60 | 144–145 |
| 73 | 3,4-butadienylene | hydrogen | 4-trifluoromethyl | C | N | HBr | 77 | 107 |
| 74 | 4-chloro | hydrogen | 4-methyl | C | N |  | 38 | 119 |
| 75 | hydrogen | methyl | 4-trifluoromethyl | C | N |  | 34 | 75 |
| 76 | 2,5-dimethoxy | hydrogen | 4-trifluoromethyl | C | N | HBr | 52 | 154–157 |
| 77 | 2,4-dimethoxy | hydrogen | 4-trifluoromethyl | C | N | HBr | 46 | 157–160 |
| 78 | 4-fluoro | hydrogen | 4-methyl | C | N |  | 44 | 129 |
| 79 | 4-fluoro | hydrogen | 4-trifluoromethyl | C | N | HCl | 67 | 100–102 |
| 80 | hydrogen | methyl | 4,5-butadienylene | C | N |  | 47 | amorphous |
| 81 | hydrogen | methyl | hydrogen | N | N |  | 31 | 146–147 |
| 82 | hydrogen | hydrogen | 4-trifluoromethyl | C | N | HBr | 36 | 150–152 |
| 83 | 3,4-dichloro | hydrogen | 4-trifluoromethyl | C | N | HBr | 41 | 146–148 |
| 84 | 4-fluoro | hydrogen | 4-methoxy | C | N |  | 17 | 184 |
| 85 | 2,4-dimethyl | hydrogen | 4-methoxy | C | N | HCl | 16 | 154 |
| 86 | hydrogen | methyl | 4-methyl | C | N |  | 13 | 65 |
| 87 | hydrogen | methyl | hydrogen | C | N |  | 24 | 80 |
| 88 | 4-hydroxy | hydrogen | 4-methyl | C | N |  | 72 | 218 |

TABLE 9

| Comp. No. | $(Z^1)_p$ | $Q^3$ | $(Z^2)_q$ | $Y^1$ | $Y^2$ | salt | yield (%) | melting point: (° C.) |
|---|---|---|---|---|---|---|---|---|
| 89 | 4-methylsulfamoyl | hydrogen | 4,5-butadienylene | C | N |  | 24 | amorphous |
| 90 | 3,4-ethylenedioxy | hydrogen | 4-trifluoromethyl | C | N | HBr | 54 | 148–150 |
| 91 | 4-fluoro | methyl | 4-trifluoromethyl | C | N | HCl | 16 | 84 |
| 92 | 4-fluoro | methyl | 4-methyl | C | N |  | 21 | 82 |
| 93 | 2-fluoro | hydrogen | 4-trifluoromethyl | C | N | HBr | 81 | 155–158 |
| 94 | 3-fluoro | hydrogen | 4-trifluoromethyl | C | N | HBr | 64 | 160–163 |
| 95 | 4-acetoxy | hydrogen | 4-trifluoromethyl | C | N |  | 97 | 116–118 |
| 96 | 2,4-bistrifluoromethyl | hydrogen | 4-trifluoromethyl | C | N | HCl | 67 | 102–103 |
| 97 | 3,4-ethylenedioxy | hydrogen | 4-methoxy | C | N |  | 52 | 152 |
| 98 | hydrogen | ethoxycarbonyl | 4-trifluoromethyl | C | N |  | 46 | oil |
| 99 | 4-fluoro | methyl | hydrogen | C | N |  | 31 | 136 |
| 100 | 4-fluoro | hydrogen | dimethylamino | C | N | 2HCl | 78 | 189–192 |
| 101 | 4-fluoro | hydrogen | 4-methylthio | C | N | HCl | 64 | 195–199 |
| 102 | hydrogen | hydrogen | 4-trifluoromethyl | N | N | 2HCl | 76 | 171–173 |

TABLE 10

| Comp. No. | $(Z^1)_p$ | $Q^3$ | $(Z^2)_q$ | $Y^1$ | $Y^2$ | salt | yield (%) | melting point: (° C.) |
|---|---|---|---|---|---|---|---|---|
| 103 | 4-methyl | hydrogen | 4-methyl | C | N |  | 65 | 98 |
| 104 | 2-methoxy | hydrogen | 4-methyl | C | N |  | 28 | 106 |
| 105 | 3,4-ethylenedioxy | hydrogen | 4-methyl | C | N |  | 58 | 87 |
| 106 | 2,4-dimethoxy | hydrogen | 4-methyl | C | N |  | 22 | 88 |
| 107 | 3,4-dimethyl | hydrogen | 4-methyl | C | N |  | 53 | 78 |
| 108 | 2,4-difluoro | hydrogen | 4-methyl | C | N |  | 21 | 89 |
| 109 | 2,4-bistrifluoromethyl | hydrogen | 4-methyl | C | N | HCl | 27 | 155 |
| 110 | 3-methoxy | hydrogen | 4-methyl | C | N |  | 35 | amorphous |
| 111 | 3-nitro | hydrogen | 4-methyl | C | N |  | 61 | 149 |
| 112 | 4-ethoxycarbonyl | hydrogen | 4-methyl | C | N |  | 62 | 116 |
| 113 | 3-fluoro | hydrogen | 4-methyl | C | N |  | 37 | 136 |
| 114 | 2-chloro | hydrogen | 4-methyl | C | N | HCl | 44 | 136 |
| 115 | 4-trifluoromethyl | hydrogen | 4-methyl | C | N | HBr | 48 | 128 |
| 116 | 4-fluoro | hydrogen | 4-ethyl | C | N | HBr | 74 | 233–235 |
| 117 | 4-fluoro | hydrogen | 4-(benzylmethyl)amino | C | N | 2HCl | 64 | 204–205 |

TABLE 11

| Comp. No. | $(Z^1)_p$ | $Q^3$ | $(Z^2)_q$ | $Y^1$ | $Y^2$ | salt | yield (%) | melting point: (° C.) |
|---|---|---|---|---|---|---|---|---|
| 118 | 4-dibenzylsulfamoyl | hydrogen | 4-trifluoromethyl | C | N | | 74 | 130 |
| 119 | 4-dibenzylsulfamoyl | hydrogen | 4-methyl | C | N | | 45 | 160 |
| 120 | 3-acetylamino | hydrogen | 4-trifluoromethyl | C | N | HCl | 70 | 154–155 |
| 121 | hydrogen | hydrogen | 4-methyl | N | N | | 32 | 110 |
| 122 | 4-methylsulfamoyl | hydrogen | 4-trifluoromethyl | C | N | | 63 | 197 |
| 123 | 4-methylsulfamoyl | hydrogen | 4-methyl | C | N | | 46 | 164 |
| 124 | 4-fluoro | hydrogen | 4-isopropoxy | C | N | | 64 | 114 |
| 125 | 4-methylsulfonyl | hydrogen | 4-methyl | C | N | | 51 | 167 |
| 126 | 2-fluoro | methyl | 4-methyl | C | N | | 39 | 95 |
| 127 | 3,4-butadienylene | hydrogen | 4-methyl | C | N | | 63 | 116 |
| 128 | 3-methoxy | hydrogen | 4-isopropoxy | C | N | | 55 | 74–76 |
| 129 | hydrogen | hydrogen | hydrogen | N | N | HBr | 64 | 195–198 |
| 130 | 4-methylsulfamoyl | hydrogen | hydrogen | C | N | HCl | 58 | 211–213 |
| 131 | 4-methylsulfonyl | hydrogen | hydrogen | C | N | HBr | 74 | 220–223 |

TABLE 12

| Comp. No. | $(Z^1)_p$ | $Q^3$ | $(Z^2)_q$ | $Y^1$ | $Y^2$ | salt | yield (%) | melting point: (° C.) |
|---|---|---|---|---|---|---|---|---|
| 132 | 4-hydroxy | hydrogen | 4,5-butadienylene | C | N | | 79 | 142 |
| 133 | 4-fluoro | hydrogen | 4,5-butadienylene | C | N | | 33 | 95 |
| 134 | 4-methyl | hydrogen | 2-chloro | N | C | | 90 | 111–112 |
| 135 | 4-methyl | hydrogen | 4-sulfamoyl | N | C | | 54 | 192–195 |
| 136 | hydrogen | hydrogen | 4-fluoro | N | C | HBr | 84 | 225–227 |
| 137 | 4-methyl | hydrogen | 4-fluoro | N | C | HCl | 93 | 180–183 |
| 138 | 4-methyl | methyl | 4-sulfamoyl | N | C | | 50 | 202–204 |
| 139 | 4-methyl | hydrogen | 2,4-difluoro | N | C | HBr | 82 | 225–230 |

EXAMPLE 3 ethyl 5-[4-(4-chlorophenyl)-1,3-thiazol-2-yl]nicotinic acid (140)

A solution of compound (41) (0.25 g, 0.91 mmol) in tetrahydrofuran (5 ml) was cooled to −78° C. under an argon atmosphere and 1.6 M n-butyllithium-hexane solution (0.57 ml, 0.91 mmol) was added. After stirring at −78° C. for 30 min., a solution of zinc chloride (0.12 g, 0.91 mmol) in tetrahydrofuran (2 ml) was added to the reaction mixture. The reaction mixture was warmed to room temperature and stirred for 30 min. and ethyl 5-bromonicotinate (0.21 g, 0.91 mmol) and tetrakis(triphenylphosphine)palladium (0.16 g, 0.14 mmol) were added. The mixture was heated to 75° C. and stirred for 2 hrs. After cooling, the reaction mixture was poured into ice water and partitioned between ethyl acetate and brine. The aqueous layer was extracted with ethyl acetate and the extracts were combined and dried ($MgSO_4$), and the solvent was evaporated under reduced pressure. The obtained residue was purified by silica gel column chromatography, and crystallized from ethyl acetate-n-hexane to give white crystals (0.16 g, 51%).

melting point: 132–135° C.

elemental analysis for $C_{17}H_{13}ClN_2O_2S$

|  | C (%) | H (%) | N (%) |
|---|---|---|---|
| Calculated: | 59.21; | 3.80; | 8.12 |
| Found: | 59.15; | 3.66; | 7.97 |

$^1$H-NMR (200 Hz, $CDCl_3$) δ: 1.50 (3H, t, J=7.1 Hz), 4.49 (2H, q, J=7.1 Hz), 7.44 (2H, d, J=8.6 Hz), 7.59 (1H, s), 7.96 (2H, d, J=8.6 Hz), 8.86 (1H, s), 9.27 (1H, s), 9.41 (1H, s).

EXAMPLE 4 methyl 3-[4-(4-chlorophenyl)-1,3-thiazol-2-yl]isonicotinic acid (141)

The compound (43) (6.0 g, 20.0 mmol), triethylamine (5.32 g, 52.6 mmol), palladium acetate (930 mg, 4.0 mmol), and dppf (2.22 g, 4.0 mmol) were dissolved in DMF (80 ml)-methanol (40 ml) under an argon atmosphere and the mixture was stirred at 70° C. for 40 hrs. under a carbon monoxide atmosphere. The solvent was evaporated and, after cooling, the reaction mixture was partitioned between ethyl acetate and aqueous sodium hydrogen carbonate. The aqueous layer was extracted with ethyl acetate. The extracts were combined, dried ($MgSO_4$), and the solvent was evaporated under reduced pressure. The obtained residue was purified by silica gel column chromatography, and crystallized from ethyl acetate-n-hexane to give white crystals (4.71 g, 69%).

melting point: 92–94° C.

elemental analysis for $C_{16}H_{11}ClN_2O_2S$

|  | C (%) | H (%) | N (%) |
|---|---|---|---|
| Calculated: | 58.09; | 3.35; | 8.47 |
| Found: | 58.23; | 3.56; | 8.58 |

$^1$H-NMR (200 Hz, $CDCl_3$) δ: 3.83 (3H, s), 7.41 (2H, d, J=8.4 Hz), 7.55 (1H, d, J=4.4 Hz), 7.60 (1H, s), 7.87 (2H, d, J=8.4 Hz), 8.78 (1H, d, J=5.2 Hz), 9.05 (1H, s).

EXAMPLE 5

4-{3-[4-(4-chlorophenyl)-1,3-thiazol-2-yl]pyridine-4-yl}morpholine (142)

Morpholine (5 ml) was added to compound (43) (120 mg, 0.40 mmol) and sodium iodide (156 mg, 0.40 mmol). The reaction mixture was heated to 80° C. and stirred for 6 hrs. The solvent was evaporated under reduced pressure, and the obtained residue was partitioned between ethyl acetate and aqueous sodium hydrogen carbonate. The aqueous layer was extracted with ethyl acetate. The extracts were combined, dried ($MgSO_4$) and the solvent was evaporated under reduced pressure. The residue was purified by silica gel column chromatography, and crystallized from ethyl acetate-n-hexane to give white crystals (100 mg, 67%).

melting point: 169° C.

elemental analysis for $C_{19}H_{16}ClN_3OS \cdot 0.5H_2O$

|  | C (%) | H (%) | N (%) |
|---|---|---|---|
| Calculated: | 60.23; | 4.52; | 11.09 |
| Found: | 59.71; | 4.58; | 11.47 |

$^1$H-NMR (200 Hz, $CDCl_3$) δ: 3.06 (4H, m), 3.88 (4H, m), 7.01 (1H, d, J=5.8 Hz), 7.27 (1H, s), 7.42 (2H, d, J=8.6 Hz), 7.59 (1H, s), 7.95 (2H, d, J=8.6 Hz), 8.53 (1H, d, J=5.8 Hz), 9.14 (1H, s).

EXAMPLE 6

Examples of the compounds produced according to the method described in Example 5 using commercially available amine derivative as a starting material are shown in Table 13.

TABLE 13

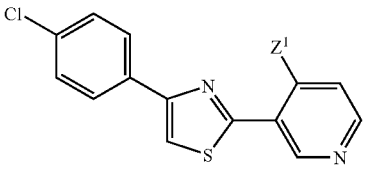

| Comp. No. | $Z^1$ | yield (%) | melting point: (° C.) |
|---|---|---|---|
| 143 | 4-(4-chlorophenyl)-4-hydroxypiperidino | 30 | 198 |
| 144 | carbamoylmethylamino | 40 | 202 |

EXAMPLE 7

2-{3-[4-(4-chlorophenyl)-1,3-thiazol-2-yl]pyridin-4-yl}propan-2-ol (145)

The compound (141) (857 mg, 2.5 mmol) was dissolved in anhydrous tetrahydrofuran (5 ml) and a 2M solution (3 ml, 6.0 mmol) of MeMgI in ether was added under ice-cooling. The reaction mixture was stirred at room temperature for one hr.

The reaction mixture was partitioned between ethyl acetate and aqueous ammonium chloride and the aqueous layer was extracted with ethyl acetate. The organic layers were combined and dried ($MgSO_4$). The solvent was evaporated under reduced pressure, and the residue was purified by silica gel column chromatography to give the title compound as white crystals (480 mg, 61%).

melting point: 146° C.

elemental analysis for $C_{17}H_{15}ClN_2OS$

|  | C (%) | H (%) | N (%) |
|---|---|---|---|
| Calculated: | 61.72; | 4.57; | 8.47 |
| Found: | 61.98; | 4.58; | 8.55 |

$^1$H-NMR (200 Hz, $CDCl_3$) δ: 1.55 (3H, s), 1.59 (3H, s), 7.43 (2H, d, J=8.8 Hz), 7.52 (1H, d, J=5.0 Hz), 7.64 (1H, s), 7.72 (1H, s), 7.81 (2H, d, J=8.8 Hz), 8.68 (1H, d, J=5.0 Hz), 8.93 (1H, s).

EXAMPLE 8

3-[4-(4-chlorophenyl)-1,3-thiazol-2-yl]-N,N-dimethylisonicotinamide (146)

The compound (141) (170 mg, 0.5 mmol) was dissolved in methanol (10 ml)-1N NaOH aq. (10 ml) and the mixture was stirred at 40° C. for one hr. The pH of the reaction mixture was adjusted to around 6, and the precipitated solid was collected by filtration, which was dried in vacuo and dissolved in dimethylformamide (3 ml) together with WSC (117 mg, 0.6 mmol), HOBt (85 mg, 0.6 mmol) and dimethylamine (27 mg, 0.6 mmol). The mixture was stirred at 30° C. for 2 hrs. The reaction mixture was partitioned between ethyl acetate and aqueous sodium hydrogen carbonate. The aqueous layer was extracted with ethyl acetate, and the organic layers were combined and dried ($MgSO_4$). The solvent was evaporated under reduced pressure, and the residue was purified by silica gel column chromatography to give the title compound as white crystals (120 mg, 35%).

melting point: 195° C.

elemental analysis for $C_{17}H_{14}ClN_3OS$

|  | C (%) | H (%) | N (%) |
|---|---|---|---|
| Calculated: | 59.38; | 4.10; | 12.22 |
| Found: | 59.11; | 4.17; | 12.23 |

$^1$H-NMR (200 Hz, $CDCl_3$) δ: 2.80 (3H, s), 3.14 (3H, s), 7.39 (1H, d, J=5.2 Hz), 7.41 (2H, d, J=7.0 Hz), 7.57 (1H, s), 7.86 (2H, d, J=7.0 Hz), 8.71 (1H, d, J=5.2 Hz), 9.17 (1H, s).

EXAMPLE 9

Examples of the compounds produced according to the method described in Example 8 using commercially available amine derivative as a starting material are shown in Table 14.

TABLE 14

| Comp. No. | Z¹ | yield (%) | melting point: (° C.) |
|---|---|---|---|
| 147 | carbamoyl | 24 | 201 |
| 148 | methylcarbamoyl | 30 | 205 |
| 149 | (4-benzylpiperidino)carbonyl | 18 | amorphous |

EXAMPLE 10

3-[5-chloro-4-(4-chlorophenyl)-1,3-thiazol-2-yl]-4-methylpyridine (150)

The compound (74) (286 mg, 1.0 mmol) was dissolved in dimethylformamide (2 ml) and a solution of trichloroisocyanuric acid (100 mg, 0.4 mmol) in dimethylformamide (1 ml) was added under ice-cooling. The reaction mixture was stirred at room temperature for one hr. and partitioned between ethyl acetate and aqueous sodium hydrogen carbonate. The aqueous layer was extracted with ethyl acetate, and the organic layers were combined and dried (MgSO$_4$). The solvent was evaporated under reduced pressure to give the title compound as white crystals (190 mg, 59%).

melting point: 146° C.

elemental analysis for $C_{15}H_{10}Cl_2N_2S$

|  | C (%) | H (%) | N (%) |
|---|---|---|---|
| Calculated: | 56.09; | 3.14; | 8.72 |
| Found: | 55.95; | 3.13; | 8.43 |

$^1$H-NMR (200 Hz, CDCl$_3$) δ: 2.67 (3H, s), 7.25 (1H, d, J=5.2 Hz), 7.45 (2H, d, J=8.2 Hz), 8.00 (2H, d, J=8.2 Hz), 8.53 (1H, d, J=5.2 Hz), 8.89 (1H, s).

EXAMPLE 11

Examples of the compounds produced according to the method described in Example 10 using compounds (104) and (125) as starting materials are shown in Table 15.

TABLE 15

| Comp. No. | (Z¹)$_p$ | salt | yield (%) | melting point: (° C.) |
|---|---|---|---|---|
| 151 | 2-methoxy | HCl | 51 | 143 |
| 152 | 4-methylsulfamoyl |  | 85 | 138 |

EXAMPLE 12

3-[5-fluoro-4-(4-methylphenyl)-1,3-thiazol-2-yl]-4-methylpyridine (153)

The compound (103) (133 mg, 0.5 mmol) was dissolved in acetonitrile (5 ml) and a solution of Selectfluor™ (236 mg, 0.6 mmol) in acetonitrile (3 ml) was added. The reaction mixture was stirred under heating under reflux for 16 hrs. The reaction mixture was partitioned between ethyl acetate and aqueous sodium hydrogen carbonate. The aqueous layer was extracted with ethyl acetate, and the organic layers were combined and dried (MgSO$_4$). The solvent was evaporated under reduced pressure, and the residue was purified by silica gel column chromatography to give the title compound as crystals (30 mg, 21%).

melting point: 96° C.

elemental analysis for $C_{16}H_{13}FN_2S$

|  | C (%) | H (%) | N (%) |
|---|---|---|---|
| Calculated: | 67.58; | 4.61; | 9.85 |
| Found: | 67.87; | 4.77; | 9.88 |

$^1$H-NMR (200 Hz, CDCl$_3$) δ: 2.41 (3H, s), 2.69 (3H, s), 7.23–7.30 (3H, m), 7.87 (2H, d, J=8.0 Hz), 8.50 (1H, d, J=5.0 Hz), 8.84 (1H, s).

EXAMPLE 13

4-[2-(4-methylpyridin-3-yl)-1,3-thiazol-4-yl]benzenesulfonamide (154)

The compound (119) (770 mg, 1.3 mmol) was dissolved in conc. sulfuric acid (3.0 ml) and the mixture was stirred at 10° C. for 0.5 hr. The reaction mixture was poured into ice water (50 ml) and neutralized with 5% aqueous sodium hydrogen carbonate. The reaction mixture was extracted with ethyl acetate-tetrahydrofuran (1:1) and the organic layer was dried (MgSO$_4$). The solvent was evaporated under reduced pressure, and the residue was recrystallized from a small amount of dichloromethane to give the title compound as white crystals (260 mg, 67%).

melting point: 219° C.

elemental analysis for $C_{15}H_{13}N_3O_2S_2$ 0.25H$_2$O

|  | C (%) | H (%) | N (%) |
|---|---|---|---|
| Calculated: | 53.63; | 4.05; | 12.51 |
| Found: | 53.81; | 3.99; | 12.22 |

$^1$H-NMR (200 Hz, CDCl$_3$) δ: 2.68 (3H, s), 7.43 (1H, s), 7.47 (1H, d, J=5.2 Hz), 7.93 (2H, d, J=8.4 Hz), 8.24 (2H, d, J=8.4 Hz), 8.52 (1H, s), 8.55 (1H, d, J=5.2 Hz), 9.00 (1H, s).

EXAMPLE 14

As a compound that can be produced according to a method similar to the method described in Example 13 using compound (118) as a starting material, 4-{2-[4-(trifluoromethyl)pyridin-3-yl]-1,3-thiazol-4-yl}benzenesulfonamide (155) can be obtained in a yield of 52%.

melting point: 217° C.

elemental analysis for $C_{15}H_{10}F_3N_3O_2S_2$ 0.5H$_2$O

|  | C (%) | H (%) | N (%) |
| --- | --- | --- | --- |
| Calculated: | 45.68; | 2.81; | 10.65 |
| Found: | 45.94; | 2.59; | 10.84 |

$^1$H-NMR (200 Hz, CDCl$_3$) δ: 7.43 (1H, s), 7.91–8.23 (5H, m), 8.62(1H, s), 9.03 (1H, d, J=5.2 Hz), 9.14 (1H, s).

EXAMPLE 15

4-{2-[4-(trifluoromethyl)pyridin-3-yl]-1,3-thiazol-4-yl}aniline (156)

The compound (59) (0.61 g, 1.72 mmol) was dissolved in formic acid (10 ml) and Pd—C (0.06 g, 10 wt. %) was added. The mixture was stirred at normal temperature and normal pressure under a hydrogen atmosphere for 2 hrs. The catalyst and the like were filtered off and formic acid was concentrated under reduced pressure. The residue was partitioned between ethyl acetate and saturated aqueous sodium hydrogen carbonate. The organic layer was washed with brine and dried (MgSO$_4$). The solvent was evaporated under reduced pressure, and the obtained residue was purified by silica gel column chromatography to give white crystals (0.23 g, 42%).

melting point: 71–72° C.

elemental analysis for C$_{15}$H$_{10}$N$_3$SF$_3$.

|  | C (%) | H (%) | N (%) |
| --- | --- | --- | --- |
| Calculated: | 56.07; | 3.14; | 13.08 |
| Found: | 56.08; | 3.09; | 13.12 |

$^1$H-NMR (200 Hz, CDCl$_3$) δ: 3.80 (2H, s), 6.76 (2H, d, J=8.8 Hz), 7.48 (1H, s), 7.70 (1H, d, J=5.2 Hz), 7.77 (2H, d, J=8.8 Hz), 8.87 (1H, d, J=5.2 Hz), 9.05 (1H, s).

EXAMPLE 16

3-{2-[4-(trifluoromethyl)pyridin-3-yl]-1,3-thiazol-4-yl}aniline (157)

In the same manner as in Example 15, a colorless amorphous compound (0.94 g, quant.) was obtained from compound (60) (1.00 g, 2.85 mmol).

elemental analysis for C$_{15}$H$_{10}$N$_3$SF$_3$.

|  | C (%) | H (%) | N (%) |
| --- | --- | --- | --- |
| Calculated: | 56.07; | 3.14; | 13.08 |
| Found: | 56.00; | 3.23; | 13.02 |

$^1$H-NMR (200 Hz, CDCl$_3$) δ: 3.64 (2H, s), 6.71 (1H, d, J=7.6 Hz), 7.19–7.35 (3H, m), 7.65 (1H, s), 7.70 (1H, d, J=5.2 Hz), 8.88 (1H, d, J=5.2 Hz), 9.04 (1H, s).

EXAMPLE 17

N-(4-{2-[4-(trifluoromethyl)pyridin-3-yl]-1,3-thiazol-4-yl}phenyl)acetamide (158)

To a solution of compound (156) (0.20 g, 0.63 mmol) in dichloromethane (3 ml) were added pyridine (0.05 ml, 0.63 mmol) and acetyl chloride (0.04 ml, 0.63 mmol) under ice-cooling. The reaction mixture was warmed to room temperature and, after stirring for one hr., partitioned between ethyl acetate and brine. The aqueous layer was extracted with ethyl acetate, and the extracts were combined and dried (MgSO$_4$). The solvent was evaporated under reduced pressure. The obtained residue was crystallized from ethyl acetate to give white crystals (0.17 g, 76%).

melting point: 216–213° C.

elemental analysis for C$_{17}$H$_{12}$N$_3$OSF$_3$

|  | C (%) | H (%) | N (%) |
| --- | --- | --- | --- |
| Calculated: | 56.19; | 3.33; | 11.56 |
| Found: | 56.10; | 3.30; | 11.42 |

$^1$H-NMR (200 Hz, DMSO-d$_6$) δ: 2.07 (3H, s), 7.68 (2H, d, J=8.8 Hz), 7.95 (2H, d, J=8.8 Hz), 7.99 (2H, d, J=5.2 Hz), 8.10 (1H, brs), 8.30 (1H, s), 9.02 (2H, d, J=5.2 Hz), 9.11 (1H, s).

EXAMPLE 18

N-(3-{2-[4-(trifluoromethyl)pyridin-3-yl]-1,3-thiazol-4-yl}phenyl)acetamide hydrochloride (159)

In the same manner as in Example 17, a colorless amorphous compound (0.30 g, 70%) was obtained from compound (157) (0.38 g, 1.18 mmol). To a solution of this amorphous compound in methanol (3 ml) was added 4N ethyl acetate-hydrochloric acid (0.22 ml) under ice-cooling and the mixture was stirred at the same temperature for 10 min. The reaction mixture was concentrated under reduced pressure and the obtained residue was crystallized from ethyl acetate-methanol to give hydrochloride as yellow needle crystals.

melting point: 154–155° C.

elemental analysis for C$_{17}$H$_{12}$N$_3$OSF$_3$.HCl 0.1H$_2$O

|  | C (%) | H (%) | N (%) |
| --- | --- | --- | --- |
| Calculated: | 50.84; | 3.31; | 10.45 |
| Found: | 50.76; | 3.54; | 10.36 |

$^1$H-NMR (200 Hz, CDCl$_3$) δ: 2.21 (3H, s), 7.38–7.46 (2H, m), 7.62–7.74 (4H, m), 8.06 (1H, s), 8.90 (1H, d, J=4.8 Hz), 9.05 (1H, s).

EXAMPLE 19

N-(4-{2-[4-(trifluoromethyl)pyridin-3-yl]-1,3-thiazol-4-yl}phenyl)methanesulfonamide hydrochloride (160)

In the same manner as in Example 17, a colorless amorphous compound (0.25 g, 72%) was obtained from compound (156) (0.28 g, 0.87 mmol) using methanesulfonyl chloride instead of acetyl chloride. To a solution of this amorphous compound in methanol (3 ml) was added 4N ethyl acetate-hydrochloric acid (0.16 ml) under ice-cooling and the mixture was stirred at the same temperature for 10 min. The reaction mixture was concentrated under reduced pressure and the obtained residue was crystallized from ethyl acetate-methanol to give hydrochloride as yellow needle crystals.

melting point: 205–207° C.
elemental analysis for $C_{16}H_{12}N_3O_2S_2F_3 \cdot HCl$

|  | C (%) | H (%) | N (%) |
|---|---|---|---|
| Calculated: | 44.09; | 3.01; | 9.64 |
| Found: | 44.07; | 2.97; | 9.69 |

$^1$H-NMR (200 Hz, CDCl$_3$) δ: 3.06 (3H, s), 6.45 (1H, s), 7.31 (2H, d, J=8.8 Hz), 7.67 (1H, s), 7.73 (1H, d, J=4.8 Hz), 7.98 (2H, d, J=8.8 Hz), 8.91 (1H, d, J=4.8 Hz), 9.06 (1H, s).

EXAMPLE 20

N-(3-{2-[4-(trifluoromethyl)pyridin-3-yl]-1,3-thiazol-4-yl}phenyl)methanesulfonamide (161)

In the same manner as in Example 17, a colorless amorphous compound (0.28 g, 70%) was obtained from compound (157) (0.31 g, 0.96 mmol) using methanesulfonyl chloride instead of acetyl chloride. To a solution of this amorphous compound in ethyl acetate (2 ml) was added 4N ethyl acetate-hydrochloric acid (0.18 ml) under ice-cooling and the mixture was stirred at the same temperature for 10 min. The reaction mixture was concentrated under reduced pressure and the obtained residue was crystallized from ethyl acetate to give hydrochloride as yellow crystals.

melting point: 162–165° C.
elemental analysis for $C_{16}H_{12}N_3O_2S_2F_3 \cdot HCl$

|  | C (%) | H (%) | N (%) |
|---|---|---|---|
| Calculated: | 44.09; | 3.01; | 9.64 |
| Found: | 44.02; | 2.28; | 9.63 |

$^1$H-NMR (200 Hz, CDCl$_3$) δ: 3.06 (3H, s), 6.66 (1H, s), 7.27–7.42 (1H, m), 7.46 (1H, t, J=7.9 Hz), 7.72–7.84 (4H, m), 8.91 (1H, d, J=5.6 Hz), 9.05 (1H, s).

EXAMPLE 21

4-{2-[4-(trifluoromethyl)pyridin-3-yl]-1,3-thiazol-4-yl}benzoic acid (162)

To a solution of compound (69) (0.57 g, 1.24 mmol) in ethanol (15 ml) was added 1N sodium hydroxide (7.45 ml, 7.45 mmol), and the mixture was stirred at room temperature for 3 hrs. To the mixture was added 1N hydrochloric acid (7.45 ml, 7.45 mmol) and the ethanol solvent was evaporated under reduced pressure. The obtained residue was washed with water and ethanol and dried (P$_2$O$_5$) under reduced pressure to give a white powder (0.37 g, 85%).

elemental analysis for $C_{16}H_9N_2O_2SF_3 \cdot 0.4H_2O$

|  | C (%) | H (%) | N (%) |
|---|---|---|---|
| Calculated: | 53.75; | 2.76; | 7.84 |
| Found: | 53.85; | 2.60; | 7.79 |

$^1$H-NMR (200 Hz, DMSO-d$_6$) δ: 8.00–8.18 (6H, m), 8.62 (1H, s), 9.03 (1H, d, J=5.2 Hz), 9.14 (1H, s).

EXAMPLE 22

15 4-[2-(4-methylpyridin-3-yl)-1,3-thiazol-4-yl]benzoic acid (163)

In the same manner as in Example 21, a white powder (0.31 g, 94%) was obtained from compound (112) (0.37 g, 1.13 mmol).

melting point: >300° C.
elemental analysis for $C_{16}H_{12}N_2O_2S$

|  | C (%) | H (%) | N (%) |
|---|---|---|---|
| Calculated: | 65.85; | 4.08; | 9.45 |
| Found: | 64.60; | 4.19; | 9.66 |

$^1$H-NMR (200 Hz, DMSO-d$_6$) δ: 2.68 (3H, s), 7.47 (1H, d, J=5.4 Hz), 8.04 (2H, d, J=8.2 Hz), 8.17 (2H, d, J=8.2 Hz), 8.51 (1H, s), 8.56 (1H, d, J=5.4 Hz), 9.00 (1H, s).

EXAMPLE 23

4-{2-[4-(trifluoromethyl)pyridin-3-yl]-1,3-thiazol-4-yl}benzamide (164)

To a solution of compound (162) (0.45 g, 1.29 mmol) in tetrahydrofuran (12 ml) were added oxalyl chloride (0.17 ml, 2.59 mmol) and dimethylformamide (3 drops) under ice-cooling, and the mixture was stirred at room temperature for one hr. To this reaction mixture was added 28% aqueous ammonia (1.00 ml, 16.44 mmol) and the mixture was stirred at room temperature for one hr. and partitioned between ethyl acetate and saturated aqueous sodium hydrogen carbonate. The aqueous layer was extracted with ethyl acetate. The extracts were combined, washed with brine and dried (MgSO$_4$). The solvent was evaporated under reduced pressure. The obtained residue was crystallized from ethanol-ethyl acetate to give white crystals (0.45 g, quant.).

melting point: 192–193° C.
elemental analysis for $C_{16}H_{10}N_3OSF_3 \cdot 0.5AcOEt$

|  | C (%) | H (%) | N (%) |
|---|---|---|---|
| Calculated: | 54.96; | 3.59; | 10.68 |
| Found: | 54.69; | 3.47; | 10.77 |

$^1$H-NMR (200 Hz, DMSO-d$_6$) δ: 7.44 (1H.brs), 7.97–8.13 (6H, m), 8.60 (1H, s), 9.03 (1H, d, J=4.8 Hz), 9.14 (1H, s).

EXAMPLE 24

4-[2-(4-methylpyridin-3-yl)-1,3-thiazol-4-yl]benzamide (165)

In the same manner as in Example 23, a white powder (0.05 g, 17%) was obtained from compound (163) (0.30 g, 1.01 mmol).

melting point: 222–225° C.

elemental analysis for $C_{16}H_{13}N_3OS$

|  | C (%) | H (%) | N (%) |
|---|---|---|---|
| Calculated: | 65.06; | 4.44; | 14.22 |
| Found: | 64.98; | 4.56; | 14.10 |

$^1$H-NMR (200 Hz, DMSO-$d_6$) δ: 2.68 (3H, s), 7.43 (1H, brs), 7.47 (1H, d, J=5.0 Hz), 7.97–8.16 (5H, m), 8.48 (1H, s), 8.55 (1H, d, J=5.0 Hz), 9.00 (1H, s).

EXAMPLE 25

Production of 3-[4-(4-methylpyridin-3-yl)-1,3-thiazol-2-yl]benzamide i) Production of 3-cyanobenzamide A mixture of 28% aqueous ammonia (20 ml) and THF (30 ml) was cooled to 5° C. and 3-cyanobenzoyl chloride (1.45 g) was slowly added. The mixture was stirred for one hr. and the reaction mixture was extracted with ethyl acetate. The organic layer was dried and concentrated. The residue was recrystallized from ethyl acetate to give the title compound (802 mg) as colorless needle crystals.

$^1$H-NMR (CDCl$_3$+CD$_3$OD)δ: 7.61 (1H, t, J=7.8 Hz), 7.82 (1H, dt, J=7.8, 1.4 Hz), 8.13 (1H, dt, J=7.8, 1.4 Hz), 8.21 (1H, t, J=1.4 Hz).

IR (KBr): 3420, 3160, 2232, 1705, 1397 cm$^{-1}$.

ii) Production of 3-(aminocarbonothionyl)benzamide

3-Cyanobenzamide (4.67 g) was suspended in a mixture of ethanol (500 ml) and triethylamine (1.0 ml), and hydrogen sulfide gas was blown in at room temperature for 30 min. The mixture was stirred at room temperature for 4 days and the solvent was evaporated under reduced pressure. The residue was washed with a mixture of ethanol-ethyl acetate to give the title compound (5.70 g) as a pale-yellow powder.

$^1$H-NMR (DMSO-$d_6$)δ: 7.40–7.56 (2H, m), 7.91–8.08 (3H, m), 8.32 (1H, t, J=1.8 Hz), 9.58 (1H, brs), 9.98 (1H, brs).

IR (KBr): 3358, 3160, 1659, 1636, 1418 cm$^{-1}$.

iii) Production of 3-[4-(4-methylpyridin-3-yl)-1,3-thiazol-2-yl]benzamide

2-Bromo-1-(4-methylpyridin-3-yl)ethanone hydrobromate (435 mg) and 3-(aminocarbonothionyl)benzamide (202 mg) were suspended in ethanol (10 ml) and the mixture was heated under reflux for 3 hrs. The reaction mixture was cooled to room temperature and the precipitated crystals were collected by filtration and washed with a mixture of ethanol-ethyl acetate. The obtained crystals were dissolved in a mixture of aqueous sodium hydrogen carbonate-ethyl acetate-methanol and extracted with ethyl acetate. The organic layer was dried and concentrated and the residue was recrystallized from ethyl acetate-methanol to give the title compound (235 mg) as colorless powder crystals.

$^1$H-NMR (DMSO-$d_6$) δ: 2.54 (3H, s), 7.38 (1H, d, J=5.2 Hz), 7.57 (1H, brs), 7.63 (1H, t, J=7.7 Hz), 7.96–8.05 (1H, m), 8.09 (1H, s), 8.14–8.26 (2H, m), 8.43–8.50 (2H, m), 8.86 (1H, s).

IR (KBr): 3266, 3106, 3056, 1713, 1402 cm$^{-1}$.

EXAMPLE 26

Production of N-methyl-3-[4-(4-methylpyridin-3-yl)-1,3-thiazol-2-yl]benzamide i) Production of 3-cyano-N-methylbenzamide A mixture of 40% aqueous methylamine solution (20 ml) and THF (30 ml) was cooled to 5° C., and 3-cyanobenzoyl chloride (1.89 g) was slowly added. The mixture was stirred for one hr. The reaction mixture was extracted with ethyl acetate, and the organic layer was dried and concentrated. The residue was recrystallized from ethyl acetate to give the title compound (1.14 g) as colorless needle crystals.

$^1$H-NMR (CDCl$_3$) δ: 3.06 (3H, d, J=4.8 Hz), 6.26 (1H, brs), 7.59 (1H, t, J=7.9 Hz), 7.80 (1H, dt, J=7.9, 2.6 Hz), 7.95–8.10 (2H, m).

IR (KBr): 3293, 2232, 1636, 1559 cm$^{-1}$.

ii) Production of 3-(aminocarbonothionyl)-N-methylbenzamide

3-Cyano-N-methylbenzamide (930 mg) was dissolved in a mixture of ethanol (80 ml) and triethylamine (2.0 ml), and hydrogen sulfide gas was blown in at room temperature for 30 min. The mixture was stirred at room temperature for 36 hrs. and the solvent was evaporated under reduced pressure. The residue was washed with ethyl acetate to give the title compound (731 mg) as a pale-brown powder.

$^1$H-NMR (DMSO-$d_6$)δ: 2.79 (3H, d, J=4.8 Hz), 7.49 (1H, t, J=7.8 Hz), 7.86–8.04 (2H, m), 8.29 (1H, s), 8.44–8.64 (1H, m), 9.59 (1H, brs), 9.98 (1H, brs).

IR (KBr): 3304, 1630, 1416 cm$^{-1}$.

iii) Production of N-methyl-3-[4-(4-methylpyridin-3-yl)-1,3-thiazol-2-yl]benzamide 2-Bromo-1-(4-methylpyridin-3-yl)ethanone hydrobromate (408 mg) and 3-(aminocarbonothionyl)-N-methylbenzamide (204 mg) were suspended in ethanol (10 ml) and the mixture was heated under reflux for 3 hrs. The reaction mixture was cooled to room temperature and the precipitated crystals were collected by filtration and washed with ethyl acetate. The obtained crystals were dissolved in a heated mixture of aqueous sodium hydrogen carbonate-ethyl acetate and, after partitioning, the aqueous layer was extracted with ethyl acetate. The organic layer was dried and concentrated and the residue was recrystallized from ethyl acetate to give the title compound (236 mg) as pale-yellow powder crystals.

$^1$H-NMR (DMSO-$d_6$)δ: 2.54 (3H, s), 2.82 (3H, d, J=4.4 Hz), 7.38 (1H, d, J=5.0 Hz), 7.63 (1H, t, J=7.6 Hz), 7.96 (1H, d, J=7.6 Hz), 8.09 (1H, s), 8.17 (1H, d, J=7.6 Hz), 8.44 (1H, s), 8.47 (1H, d, J=5.0 Hz), 8.60–8.76 (1H, m), 8.86 (1H, s).

IR (KBr): 3268, 3139, 1672, 1553 cm$^{-1}$.

EXAMPLE 27

Production of N,N-dimethyl-3-[4-(4-methylpyridin-3-yl)-1,3-thiazol-2-yl]benzamide i) Production of 3-cyano-N,N-dimethylbenzamide 3-Cyanobenzoic acid (12.60 g) was dissolved in THF (200 ml) and thionyl chloride (13.0 g) and DMF (0.05 ml) were added.

The mixture was stirred at 60° C. for 2 hrs. The reaction mixture was concentrated under reduced pressure and re-dissolved in THF (100 ml). The solution was slowly added to 50% aqueous dimethylamine solution (80 ml) cooled to 5° C. The reaction mixture was stirred at room temperature for one hr. and extracted with ethyl acetate. The extract was dried and concentrated, and the residue was recrystallized from hexane-diisopropyl ether to give the title compound (8.00 g) as colorless powder crystals.

$^1$H-NMR (CDCl$_3$) δ: 2.99 (3H, s), 3.13 (3H, s), 7.55 (1H, t, J=8.1 Hz), 7.64–7.74 (3H, m).

IR (KBr): 3054, 2228, 1613, 1580 cm$^{-1}$.

ii) Production of 3-(aminocarbonothionyl)-N,N-dimethylbenzamide

3-Cyano-N,N-dimethylbenzamide (7.90 g) was dissolved in ethanol (500 ml) and triethylamine (2.0 ml), and hydrogen sulfide gas was blown in at room temperature for 30 min. The mixture was stirred at room temperature for 4 days and the solvent was evaporated under reduced pressure. The residue was washed with ethyl acetate to give the title compound (8.60 g) as a brown powder.

$^1$H-NMR (DMSO-d$_6$)δ: 2.91 (3H, s), 3.00 (3H, s), 7.42–7.57 (2H, m), 7.86–7.98 (2H, m), 9.59, (1H, brs), 9.97 (1H, brs).

IR (KBr): 3210, 3056, 1615, 1601 cm$^{-1}$.

iii) Production of N,N-dimethyl-3-[4-(4-methylpyridin-3-yl)-1,3-thiazol-2-yl]benzamide 2-Bromo-1-(4-methylpyridin-3-yl)ethanone hydrobromate (1.53 g) and 3-(aminocarbonothionyl)-N,N-dimethylbenzamide (1.00 g) were suspended in ethanol (20 ml) and the mixture was heated under reflux for 2 hrs. Aqueous sodium hydrogen carbonate was added to the reaction mixture and the mixture was extracted with ethyl acetate. The organic layer was dried and concentrated, and the residue was subjected to silica gel column chromatography (eluent, methanol:ethyl acetate=1:40) for purification. The eluate was recrystallized from ethyl acetate-diisopropyl ether to give the title compound (1.26 g) as pale-yellow powder crystals.

$^1$H-NMR (CDCl$_3$) δ: 2.54 (3H, s), 3.03 (3H, s), 3.15 (3H, s), 7.22 (1H, d, J=5.2 Hz), 7.38–7.41 (1H, m), 7.46–7.60 (2H, m), 8.00–8.10 (2H, m), 8.48 (1H, d, J=5.2 Hz), 8.81 (1H, s).

IR (KBr): 2930, 1634, 1395 cm$^{-1}$.

EXAMPLE 28

Production of 4-[4-(4-methylpyridin-3-yl)-1,3-thiazol-2-yl]benzamide i) Production of 4-cyanobenzamide By the reaction in the same manner as in Example 25-i) using 4-cyanobenzoyl chloride (5.30 g) and 28% aqueous ammonia (20 ml), the title compound (3.62 g) was obtained by pale-brown needle crystals.

$^1$H-NMR (CDCl$_3$+CD$_3$OD) δ: 7.76 (2H, d, J=8.1 Hz), 7.96 (2H, d, J=8.1 Hz).

IR (KBr): 3443, 3177, 2230, 1701, 1618, 1561, 1414, 1399 cm$^{-1}$.

ii) Production of 4-(aminocarbonothionyl)benzamide

By the reaction in the same manner as in Example 25-ii) using 4-cyanobenzamide (2.66 g), the title compound (3.05 g) was obtained as a yellow powder.

$^1$H-NMR (DMSO-d$_6$)δ: 7.51 (1H, brs), 7.80–7.98 (4H, m), 8.08 (1H, brs), 9.61 (1H, brs), 10.01 (1H, brs).

IR (KBr): 3164, 1659, 1632, 1568, 1427 cm$^{-1}$.

iii) Production of 4-[4-(4-methylpyridin-3-yl)-1,3-thiazol-2-yl]benzamide

By the reaction in the same manner as in Example 25-iii) using 2-bromo-1-(4-methylpyridin-3-yl)ethanone hydrobromate (503 mg) and 4-(aminocarbonothionyl)benzamide (232 mg), the title compound (300 mg) was obtained as an amorphous compound.

$^1$H-NMR (DMSO-d$_6$)δ: 2.54 (3H, s), 7.38 (1H, d, J=4.9 Hz), 7.52 (1H, brs), 7.96–8.18 (6H, m), 8.47 (1H, d, J=4.9 Hz), 8.85 (1H, s).

IR (KBr): 3169, 1703, 1416, 1397 cm$^{-1}$.

EXAMPLE 29

Production of N-methyl-4-[4-(4-methylpyridin-3-yl)-1,3-thiazol-2-yl]benzamide i) Production of 4-cyano-N-methylbenzamide By the reaction in the same manner as in Example 26-i) using 4-cyanobenzoyl chloride (5.17 g) and 40% aqueous methylamine solution (20 ml), the title compound (4.13 g) was obtained as colorless powder crystals.

$^1$H-NMR (CDCl$_3$) δ: 3.04 (3H, d, J=4.8 Hz), 6.23 (1H, brs), 7.74 (2H, d, J=8.5 Hz), 7.86 (2H, d, J=8.5 Hz).

IR (KBr): 3341, 2228, 1644, 1555 cm$^{-1}$.

ii) Production of 4-(aminocarbonothionyl)-N-methylbenzamide

By the reaction in the same manner as in Example 25-ii) using 4-cyano-N-methylbenzamide (2.04 g), the title compound (2.26 g) was obtained as a yellow powder.

$^1$H-NMR (DMSO-d$_6$)δ: 2.79 (3H, d, J=4.4 Hz), 7.83 (2H, d, J=8.8 Hz), 7.92 (2H, d, J=8.8 Hz), 8.50–8.64 (1H, m), 9.61 (1H, brs), 10.01 (1H, brs).

IR (KBr): 3113, 1634, 1547 cm$^{-1}$.

iii) Production of N-methyl-4-[4-(4-methylpyridin-3-yl)-1,3-thiazol-2-yl]benzamide By the reaction in the same manner as in Example 25-iii) using 2-bromo-1-(4-methylpyridin-3-yl)ethanone hydrobromate (482 mg) and 4-(aminocarbonothionyl)-N-methylbenzamide (243 mg), the title compound (207 mg) was obtained as an amorphous compound.

$^1$H-NMR (DMSO-d$_6$) δ: 2.54 (3H, s), 2.81 (3H, d, J=4.4 Hz), 7.38 (1H, d, J=5.2 Hz), 7.98 (2H, d, J=8.6 Hz), 8.11 (2H, d, J=8.6 Hz), 8.11 (1H, s), 8.47 (1H, d, J=5.2 Hz), 8.54–8.67 (1H, m), 8.85 (1H, s).

IR (KBr): 3343, 1645, 1563 cm$^{-1}$.

EXAMPLE 30

Production of N, 4-dimethyl-3-[4-(4-methylpyridin-3-yl)-1,3-thiazol-2-yl]benzamide i) Production of 3-iodo-N, 4-dimethylbenzamide 3-Iodo-4-methylbenzoic acid (9.84 g) was dissolved in THF (50 ml) and thionyl chloride (4 ml) and DMF (0.05 ml)

were added. The mixture was heated under ref lux for 3 hrs. The reaction mixture was concentrated under reduced pressure to give 3-iodo-4-methylbenzoyl chloride (10.18 g) as a brown powder. Then, by the reaction in the same manner as in Example 26-i), the title compound (3.47 g) was obtained from a solution of 3-iodo-4-methylbenzoyl chloride (4.00 g) and methylamine in THF (2M, 30 ml) as colorless powder crystals $^1$H-NMR (CDCl$_3$) δ: 2.46 (3H, s), 3.00 (3H, d, J=5.2 Hz), 6.11 (1H, brs), 7.28 (1H, d, J=7.6 Hz), 7.64 (1H, dd, J=1.8, 7.6 Hz), 8.19 (1H, d, J=1.8 Hz).

IR (KBr): 3322, 1638, 1549, 1480, 1410, 1316, 1265, 667 cm$^{-1}$.

ii) Production of 3-cyano-N, 4-dimethylbenzamide

3-Iodo-N, 4-dimethylbenzamide (772 mg), tetrakistriphenylphosphinepalladium (30 mg) and zinc cyanide (250 mg) were suspended in DMF (10 ml) under a nitrogen atmosphere, and the mixture was stirred at 120° C. for 12 hrs. The reaction mixture was diluted with 5% aqueous ammonia-ethyl acetate and the organic layer was washed with water and saturated brine. The organic layer was dried and concentrated, and the residue was subjected to silica gel column chromatography (eluent, hexane:ethyl acetate=2:1–0:1) for purification. The eluate was recrystallized from ethyl acetate-hexane to give the title compound (300 mg) as colorless powder crystals.

$^1$H-NMR (CDCl$_3$)δ: 2.60 (3H, s), 3.02 (1H, d, J=4.8 Hz), 6.31 (1H, brs), 7.40 (1H, d, J=8.0 Hz), 7.90 (1H, dd, J=1.8, 8.0 Hz), 8.01 (1H, d, J=1.8 Hz).

IR (KBr): 3349, 2228, 1647, 1561 cm$^{-1}$.

iii) Production of 3-(aminocarbonothionyl)-N, 4-dimethylbenzamide

By the reaction in the same manner as in Example 26-ii) using 3-cyano-N, 4-dimethylbenzamide (1.75 g), a crude title compound (2.80 g) was obtained.

$^1$H-NMR (DMSO-d$_6$)δ: 2.35 (3H, s), 2.76 (3H, d, J=4.4 Hz), 7.28 (1H, d, J=8.4 Hz), 7.66–7.76 (2H, m), 8.38–8.51 (1H, m), 9.56 (1H, brs), 10.09 (1H, brs).

IR (KBr): 3297, 3125, 1622, 1559 cm$^{-1}$.

iv) Production of N,4-dimethyl-3-[4-(4-methylpyridin-3-yl)-1,3-thiazol-2-yl]benzamide By the reaction in the same manner as in Example 25-iii) using 2-bromo-1-(4-methylpyridin-3-yl)ethanone hydrobromate (76 mg) and 3-(aminocarbonothionyl)-N,4-dimethylbenzamide (50 mg), the title compound (44 mg) was obtained as colorless powder crystals.

$^1$H-NMR (DMSO-d$_6$)δ: 2.53 (3H, s), 2.66 (3H, s), 2.81 (3H, d, J=4.8 Hz), 7.38 (1H, d, J=5.2 Hz), 7.50 (1H, d, J=7.9 Hz), 7.87 (1H, dd, J=1.8, 7.8 Hz), 8.15 (1H, s), 8.25 (1H, d, J=1.8 Hz), 8.46 (1H, d, J=5.2 Hz), 8.52–8.64 (1H, m), 8.84 (1H, s).

IR (KBr): 3340, 3044, 1663, 1551 cm$^{-1}$.

EXAMPLE 31

Production of N,N,4-trimethyl-3-[4-(4-methylpyridin-3-yl)-1,3-thiazol-2-yl]benzamide i) Production of 3-iodo-N,N,4-trimethylbenzamide By the reaction in the same manner as in Example 27-i) using 3-iodo-4-methylbenzoyl chloride (2.00 g) and 50% aqueous dimethylamine solution (20 ml), the title compound (1.72 g) was obtained as a pale-yellow oil.

$^1$H-NMR (CDCl$_3$)δ: 2.45 (3H, s), 2.99 (3H, brs), 3.08 (3H, brs), 7.20–7.34 (2H, m), 7.87 (1H, d, J=1.4 Hz).

IR (KBr): 2926, 1634, 1395 cm$^{-1}$.

ii) Production of 3-cyano-N,N,4-trimethylbenzamide

By the reaction in the same manner as in Example 30-ii) using 3-iodo-N,N,4-trimethylbenzamide (1.65 g), tetrakistriphenylphosphinepalladium (80 mg) and zinc cyanide (510 mg), the title compound (1.41 g) was obtained as a colorless oil (containing ethyl acetate).

$^1$H-NMR (CDCl$_3$)δ: 2.59 (3H, s), 3.03 (3H, s), 3.17 (3H, s), 7.39 (1H, d, J=7.9 Hz), 7.62 (1H, dd, J=1.8, 8.0 Hz), 7.69 (1H, d, J=1.8 Hz).

IR (KBr): 2936, 2226, 1634, 1404 cm$^{-1}$.

iii) Production of N,N,4-trimethyl-3-[4-(4-methylpyridin-3-yl)-1,3-thiazol-2-yl]benzamide By the reaction in the same manner as in Example 27-ii) using 3-iodo-N,N,4-trimethylbenzamide (1.30 g), crude 3-(aminocarbonothionyl)-N,N,4-trimethylbenzamide (871 mg) was obtained. Then, the title compound (19 mg) was obtained as a pale-yellow amorphous compound from 2-bromo-1-(4-methylpyridin-3-yl)ethanone hydrobromate (750 mg) and 3-(aminocarbonothionyl)-N,N,4-trimethylbenzamide (482 mg) by the reaction in the same manner as in Example 27-iii).

$^1$H-NMR (CDCl$_3$)δ: 2.56 (3H, s), 2.69 (3H, s), 3.04 (3H, brs), 3.13 (3H, brs), 7.22 (1H, d, J=4.7 Hz), 7.34–7.46 (2H, m), 7.46 (1H, s), 7.86 (1H, d, J=1.2 Hz), 8.47 (1H, d, J=4.7 Hz), 8.83 (1H, s).

IR (KBr): 2924, 1632, 1397 cm$^{-1}$.

EXAMPLE 32

Production of 4-methyl-3-{2-[2-methyl-5-(pyrrolidine-1-ylcarbonyl)phenyl]-1,3-thiazol-4-yl}pyridine i) Production of 1-(3-iodo-4-methylbenzoyl)pyrrolidine By the reaction in the same manner as in Example 26-i) using 3-iodo-4-methylbenzoyl chloride (2.00 g) and pyrrolidine (3.5 ml), the title compound (1.62 g) was obtained as a pale-yellow oil.

$^1$H-NMR (CDCl$_3$)δ: 1.80–2.04 (4H, m), 2.45 (3H, s), 3.43 (2H, t, J=6.4 Hz), 3.62 (2H, t, J=6.7 Hz), 7.24 (1H, d, J=7.5 Hz), 7.40 (1H, dd, J=1.8, 7.5 Hz), 7.97 (1H, d, J=1.8 Hz).

IR (KBr): 2971, 1624, 1422 cm$^{-1}$.

ii) Production of 1-(3-cyano-4-methylbenzoyl)pyrrolidine

By the reaction in the same manner as in Example 30-ii) using 1-(3-iodo-4-methylbenzoyl)pyrrolidine (1.55 g), tetrakistriphenylphosphinepalladium (80 mg) and zinc cyanide (460 mg), the title compound (1.44 g) was obtained as a colorless oil (containing ethyl acetate).

$^1$H-NMR (CDCl$_3$)δ: 1.80–2.05 (4H, m), 2.58 (3H, s), 3.46 (2H, t, J=6.2 Hz), 3.72 (2H, t, J=6.7 Hz), 7.38 (1H, d, J=8.0 Hz), 7.72 (1H, dd, J=1.8, 8.0 Hz), 7.79 (1H, d, J=1.8 Hz).

IR (KBr): 2975, 2228, 1620, 1445 cm$^{-1}$.

iii) Production of 4-methyl-3-{2-[2-methyl-5-(pyrrolidin-1-ylcarbonyl)phenyl]-1,3-thiazol-4-yl}pyridine By the reaction in the same manner as in Example 27-ii) using 1-(3-cyano-4-methylbenzoyl)pyrrolidine (1.24 g), crude 2-methyl-5-(pyrrolidine-1-ylcarbonyl)benzenecarbothioamide (767 mg) was obtained. Then, by the reaction in the same manner as in Example 25-iii), the title compound (44 mg) was obtained as a pale-yellow amorphous compound from 2-bromo-1-(4-methylpyridin-3-yl)ethanone hydrobromate (750 mg) and 2-methyl-5-(pyrrolidin-1-ylcarbonyl)benzenecarbothioamide (534 mg).

¹H-NMR (CDCl₃)δ: 1.60–2.10 (4H, m), 2.55 (3H, s), 2.69 (3H, s), 3.49 (2H, t, J=6.5 Hz), 3.67 (2H, t, J=6.8 Hz), 7.22 (1H, dd, J=0.8, 5.0 Hz), 7.37 (1H, dd, J=0.8, 7.5 Hz), 7.46 (1H, s), 7.51 (1H, dd, J=1.7, 7.5 Hz), 7.97 (1H, d, J=1.7 Hz), 8.47 (1H, d, J=5.0 Hz), 8.83 (1H, s).

IR (KBr): 2971, 1622, 1429 cm⁻¹.

EXAMPLE 33

Production of 4-fluoro-N-methyl-3-[4-(4-methylpyridin-3-yl)-1,3-thiazol-2-yl]benzamide i) Production of 3-cyano-4-fluoro-N-methylbenzamide By the reaction in the same manner as in Example 30-ii) using 3-bromo-4-fluoro-N-methylbenzamide (777 mg), tetrakistriphenylphosphinepalladium (40 mg) and zinc cyanide (270 mg), the title compound (210 mg) was obtained as colorless needle crystals.

¹H-NMR (CDCl₃)δ: 3.03 (3H, d, J=4.6 Hz), 6.19 (1H, brs), 7.28–7.38 (1H, m), 7.99–8.12 (2H, m).

IR (KBr): 3328, 3069, 2236, 1638, 1495 cm⁻¹.

ii) Production of 3-(aminocarbonothionyl)-4-fluoro-N-methylbenzamide

By the reaction in the same manner as in Example 27-ii) using 3-cyano-4-fluoro-N-methylbenzamide (180 mg), the title compound (210 mg) was obtained as a colorless powder.

¹H-NMR (CDCl₃+CD₃OD)δ: 2.94–3.04 (3H, m), 7.17 (1H, dd, J=8.8, 11.2 Hz), 7.49 (1H, brs), 7.92–8.03 (1H, m), 8.42 (1H, dd, J=2.2, 7.6 Hz).

IR (KBr): 3275, 3131, 1655, 1630 cm⁻¹.

iii) Production of 4-fluoro-N-methyl-3-[4-(4-methylpyridin-3-yl)-1,3-thiazol-2-yl]benzamide By the reaction in the same manner as in Example 25-iii) using 2-bromo-1-(4-methylpyridin-3-yl)ethanone hydrobromate (260 mg) and 3-(aminocarbonothionyl)-4-fluoro-N-methylbenzamide (167 mg), the title compound (142 mg) was obtained as pale-yellow powder crystals.

¹H-NMR (DMSO-d₆)δ: 2.54 (3H, s), 2.82 (3H, dd, J=4.4 Hz), 7.40 (1H, d, J=5.2 Hz), 7.58 (1H, dd, J=8.8, 11.0 Hz), 7.96–8.08 (1H, m), 8.22 (1H, s), 8.49 (1H, d, J=5.2 Hz), 8.65–8.86 (2H, m), 8.89 (1H, s).

IR (KBr): 3254, 3102, 1653, 1507 cm⁻¹.

EXAMPLE 34

Production of 2-chloro-N-methyl-5-[4-(4-methylpyridin-3-yl)-1,3-thiazol-2-yl]benzamide i) Production of 2-chloro-5-cyano-N-methylbenzamide By the reaction in the same manner as in Example 30-ii) using 5-bromo-2-chloro-N-methylbenzamide (677 mg), tetrakistriphenylphosphinepalladium (40 mg) and zinc cyanide (206 mg), the title compound (339 mg) was obtained as colorless needle crystals.

¹H-NMR (CDCl₃)δ: 3.05 (3H, d, J=4.8 Hz), 6.23 (1H, brs), 7.54 (1H, d, J=8.0 Hz), 7.65 (1H, dd, J=1.8, 8.0 Hz), 7.97 (1H, d, J=1.8 Hz).

IR (KBr): 3277, 2238, 1653, 1551 cm⁻¹.

ii) Production of 5-(aminocarbonothionyl)-2-chloro-N-methylbenzamide

By the reaction in the same manner as in Example 27-ii) using 2-chloro-5-cyano-N-methylbenzamide (310 mg), the title compound (320 mg) was obtained as a yellow powder.

¹H-NMR (DMSO-d₆)δ: 2.77 (3H, d, J=4.4 Hz), 7.56 (1H, d, J=9.2 Hz), 7.88–8.02 (2H, m), 8.38–8.54 (1H, m), 9.63 (1H, brs), 10.03 (1H, brs).

IR (KBr): 3289, 3177, 1634, 1549, 1408, 1285 cm⁻¹.

iii) Production of 2-chloro-N-methyl-5-[4-(4-methylpyridin-3-yl)-1,3-thiazol-2-yl]benzamide By the reaction in the same manner as in Example 25-iii) using 2-bromo-1-(4-methylpyridin-3-yl)ethanone hydrobromate (180 mg) and 5-(aminocarbonothionyl)-2-chloro-N-methylbenzamide (132 mg), the title compound (138 mg) was obtained as pale-yellow powder crystals.

¹H-NMR (DMSO-d₆)δ: 2.52 (3H, s), 2.79 (3H, d, J=4.4 Hz), 7.38 (1H, d, J=4.9 Hz), 7.66 (1H, d, J=8.3 Hz), 8.01 (1H, d, J=2.2 Hz), 8.07 (1H, dd, J=2.2, 8.3 Hz), 8.11 (1H, s), 8.46 (1H, d, J=4.9 Hz), 8.50–8.62 (1H, m), 8.84 (1H, s).

IR(KBr): 3277, 1645, 1063 cm⁻¹.

EXAMPLE 35

Production of N-{3-[4-(4-methylpyridin-3-yl)-1,3-thiazol-2-yl]phenyl}acetamide i) Production of N-(3-cyanophenyl)acetamide 3-Aminobenzonitrile (5.70 g) and N,N-dimethylaminopyridine (20 mg) were dissolved in pyridine (40 ml) and the mixture was cooled to 5° C. Acetic anhydride (5.8 ml) was added and the mixture was stirred at room temperature for 12 hrs. The reaction mixture was concentrated under reduced pressure. Ethyl acetate and 1N hydrochloric acid were added to the residue, and the organic layer was washed with 1N hydrochloric acid, saturated aqueous sodium hydrogen carbonate, and saturated brine. The organic layer was dried, concentrated and recrystallized from hexane-ethyl acetate to give the title compound (5.78 g) as pale-brown powder crystals.

¹H-NMR (CDCl₃)δ: 2.21 (3H, s), 7.34–7.48 (2H, m), 7.62 (1H, brs), 7.72 (1H, dt, J=7.0, 2.4 Hz), 7.93(1H, s).

IR (KBr): 3303, 3272, 2228, 1667, 1559 cm⁻¹.

ii) Production of N-[3-(aminocarbonothionyl)phenyl]acetamide

By the reaction in the same manner as in Example 27-ii) using N-(3-cyanophenyl)acetamide (2.05 g), the title compound (2.09 g) was obtained as a yellow powder.

¹H-NMR (DMSO-d₆)δ: 2.05 (3H, s), 7.25–7.48 (2H, s), 7.78 (1H, d, J=8.0 Hz), 8.05 (1H, s), 9.48 (1H, brs), 9.87 (1H, brs), 10.11 (1H, s).

IR (KBr): 3260, 3152, 1663, 1611, 1586, 1551, 1445 cm⁻¹.

iii) Production of N-{3-[4-(4-methylpyridin-3-yl)-1,3-thiazol-2-yl]phenyl}acetamide By the reaction in the same manner as in Example 25-iii) using 2-bromo-1-(4-methylpyridin-3-yl)ethanone hydrobromate (315 mg) and N-[3-(aminocarbonothionyl)phenyl]acetamide (197 mg), the title compound (142 mg) was obtained as a yellow amorphous compound.

¹H-NMR (CDCl₃+CD₃OD)δ: 2.21 (3H, s), 2.52 (3H, s), 7.21 (1H, d, J=5.2 Hz), 7.34 (1H, s), 7.40 (1H, d, J=8.2 Hz), 7.66–7.80 (2H, m), 8.08–8.22 (2H, m), 8.46 (1H, d, J=5.2 Hz), 8.81 (1H, s).

IR (KBr): 3056, 2988, 1684, 1615, 1561 cm⁻¹.

EXAMPLE 36

Production of N-{4-[4-(4-methylpyridin-3-yl)-1,3-thiazol-2-yl]phenyl}acetamide i) Production of N-(4-cyanophenyl)acetamide By the reaction in the same manner as in Example 35-i) using 4-aminobenzonitrile (5.51 g) and acetic anhydride (5.7 ml), the title compound (5.88 g) was obtained as colorless needle crystals.

$^1$H-NMR (CDCl$_3$+CD$_3$OD)δ: 2.20 (3H, s), 7.59 (2H, d, J=8.7 Hz), 7.68 (2H, d, J=8.7 Hz).
IR (KBr): 3304, 3260, 2222, 1667, 1599 cm$^{-1}$.

ii) Production of N-[4-(aminocarbonothionyl)phenyl]acetamide

By the reaction in the same manner as in Example 27-ii) using N-(4-cyanophenyl)acetamide (1.92 g), the title compound (2.17 g) was obtained as a pale-yellow powder.

$^1$H-NMR (DMSO-d$_6$)δ: 2.07 (3H, s), 7.60 (2H, d, J=8.8 Hz), 7.90 (2H, d, J=8.8 Hz), 9.36 (1H, brs), 9.71 (1H, brs).
IR (KBr): 3283, 3112, 1667, 1593, 1412 cm$^{-1}$.

iii) Production of N-{4-[4-(4-methylpyridin-3-yl)-1,3-thiazol-2-yl]phenyl}acetamide By the reaction in the same manner as in Example 25-iii) using 2-bromo-1-(4-methylpyridin-3-yl)ethanone hydrobromate (313 mg) and N-[4-(aminocarbonothionyl)phenyl]acetamide (194 mg), the title compound (172 mg) was obtained as colorless needle crystals.

$^1$H-NMR (DMSO-d$_6$)δ: 2.09 (3H, s), 2.52 (3H, s), 7.36 (1H, d, J=5.0 Hz), 7.74 (2H, d, J=8.8 Hz), 7.95 (2H, d, J=8.8 Hz), 7.96 (1H, s), 8.65 (1H, d, J=5.0 Hz), 8.82 (1H, s).
IR (KBr): 3042, 1690, 1603, 1543 cm$^{-1}$.

EXAMPLE 37

Production of 4-methyl-3-[4-(4-methylpyridin-3-yl)-1,3-thiazol-2-yl]phenylformamide 4-Methyl-3-[2-(2-methyl-5-nitrophenyl)-1,3-thiazol-4-yl]pyridine (98 mg) and reduced iron (170 mg) were suspended in a mixture of formic acid (3 ml)-ethyl formate (3 ml). 1N Hydrochloric acid (0.2 ml) was added and the mixture was stirred at 80° C. for 12 hrs. The reaction mixture was diluted with ethyl acetate and the insoluble material was filtered off. The organic layer was neutralized with saturated aqueous sodium hydrogen carbonate. The organic layer was separated and concentrated by drying. The residue was subjected to silica gel column chromatography (eluent, hexane:ethyl acetate=1:1–0:1) for purification. Recrystallization from ethyl acetate gave the title compound (15 mg) as pale-yellow columnar crystals.

$^1$H-NMR (DMSO-d$_6$)δ: 2.53 (3H, s), 2.57 (3H, s), 7.30–7.42 (2H, m), 7.61 (1H, dd, J=2.2, 8.4 Hz), 8.10 (1H, s), 8.18 (1H, d, J=2.2 Hz), 8.32 (1H, s), 8.46 (1H, d, J=4.8 Hz), 8.83 (1H, s), 10.34 (1H, s).
IR (KBr): 2861, 1686, 1620 cm$^{-1}$.

EXAMPLE 38

Production of N-{4-methyl-3-[4-(4-methylpyridin-3-yl)-1,3-thiazol-2-yl]phenyl}acetamide 4-Methyl-3-[2-(2-methyl-5-nitrophenyl)-1,3-thiazol-4-yl]pyridine (100 mg) and reduced iron (180 mg) were suspended in acetic acid (2 ml)-acetic anhydride (0.04 ml) and the mixture was stirred at 70° C. for 4 hrs. The reaction mixture was diluted with ethyl acetate and the insoluble material was filtered off. The organic layer was neutralized with saturated aqueous sodium hydrogen carbonate. The organic layer was separated and concentrated by drying. The residue was subjected to silica gel column chromatography (eluent, hexane:ethyl acetate=1:1–0:1) for purification. Recrystallization from ethyl acetate gave the title compound (43 mg) as colorless powder crystals.

$^1$H-NMR (CDCl$_3$)δ: 2.19 (3H, s), 2.54 (3H, s), 2.61 (3H, s), 7.18–7.30 (2H, m), 7.42 (1H, s), 7.58 (1H, dd, J=2.2, 8.4 Hz), 7.71 (1H, brs), 7.94 (1H, d, J=2.2 Hz), 8.46 (1H, d, J=4.8 Hz), 8.82 (1H, s).
IR (KBr): 1671, 1613, 1541 cm$^{-1}$.

EXAMPLE 39

Production of 4-methyl-3-[2-(2-pyridyl)-1,3-thiazol-4-yl]pyridine i) Production of pyridine-2-carbothioamide By the reaction in the same manner as in Example 25-ii) using 2-cyanopyridine (5.20 g), the title compound (4.73 g) was obtained as a yellow powder.

$^1$H-NMR (DMSO-d$_6$)δ: 7.55–7.66 (1H, m), 7.90–8.04 (1H, m), 8.46–8.64 (2H, m), 9.95 (1H, brs), 10.19 (1H, brs).
IR (KBr): 3353, 3154, 1603, 1582 cm$^{-1}$.

ii) Production of 4-methyl-3-[2-(2-pyridyl)-1,3-thiazol-4-yl]pyridine

By the reaction in the same manner as in Example 25-iii) using 2-bromo-1-(4-methylpyridin-3-yl)ethanone hydrobromate (446 mg) and pyridine-2-carbothioamide (157 mg), the title compound (67 mg) was obtained as pale-red powder crystals.

$^1$H-NMR (CDCl$_3$)δ: 2.55 (3H, s), 7.23 (1H, d, J=4.9 Hz), 7.30–7.42 (1H, m), 7.48 (1H, s), 7.83 (1H, dt, J=1.4, 7.9 Hz), 8.26 (1H, d, J=7.6 Hz), 8.48 (1H, d, J=4.9 Hz), 8.60–8.70 (1H, m), 8.84 (1H, s).
IR (KBr): 3100, 1582, 1433 cm$^{-1}$.

EXAMPLE 40

Production of 4-methyl-3-[2-(3-pyridyl)-1,3-thiazol-4-yl]pyridine

By the reaction in the same manner as in Example 25-iii) using 2-bromo-1-(4-methylpyridin-3-yl)ethanone hydrobromate (432 mg) and thionicotinamide (152 mg), the title compound (110 mg) was obtained as colorless powder crystals.

$^1$H-NMR (CDCl$_3$)δ: 2.55 (3H, s), 7.24 (1H, d, J=5.0 Hz), 7.37–7.46 (2H, m), 8.26–8.36 (1H, m), 8.49 (1H, d, J=5.0 Hz), 8.69 (1H, dd, J=1.8, 4.8 Hz), 8.82 (1H, s), 9.24 (1H, dd, J=1.0, 2.2 Hz).
IR (KBr): 3046, 1597, 1466 cm$^{-1}$.

EXAMPLE 41

Production of 4-methyl-3-[2-(4-pyridyl)-1,3-thiazol-4-yl]pyridine

By the reaction in the same manner as in Example 25-iii) using 2-bromo-1-(4-methylpyridin-3-yl)ethanone hydrobromate (428 mg) and thioisonicotinamide (153 mg), the title compound (77 mg) was obtained as colorless powder crystals.

¹H-NMR (CDCl₃)δ: 2.55 (3H, s), 7.24 (1H, d, J=5.0 Hz), 7.51 (1H, s), 7.88 (2H, dd, J=1.8, 4.4 Hz), 8.50 (1H, d, J=5.0 Hz), 8.74 (2H, dd, J=1.8, 4.4 Hz), 8.82 (1H, s). IR (KBr): 3044, 1597, 1468, 820 cm⁻¹.

EXAMPLE 42

Production of 5-[4-(4-methylpyridin-3-yl)-1,3-thiazol-2-yl]nicotinamide i) Production of 5-bromonicotinamide 5-Bromonicotinic acid (5.05 g), ammonium chloride (2.10 g), 1-ethyl-3-(3-dimethylaminopropyl)-carbodiimide hydrochloride (7.30 g), 1-hydroxy-1H-benzotriazole monohydrate (3.90 g) and triethylamine (5.5 ml) were suspended in DMF (40 ml) and the mixture was stirred at room temperature for 16 hrs. Ethyl acetate and water were added to the reaction mixture and the organic layer was washed with saturated aqueous sodium hydrogen carbonate, water and saturated brine. The organic layer was concentrated by drying and recrystallized from ethyl acetate to give the title compound (2.33 g) as colorless needle crystals.
¹H-NMR (CDCl₃+CD₃OD)δ: 8.41 (1H, t, J=2.2 Hz), 8.77 (1H, d, J=2.2 Hz), 8.94 (1H, d, J=2.2 Hz).
IR (KBr): 3389, 3194, 3032, 1657, 1620 cm⁻¹.

ii) Production of 5-cyanonicotinamide

5-Bromonicotinamide (905 mg) and copper cyanide (630 mg) were suspended in DMF (15 ml) and the mixture was stirred at 140° C. for 24 hrs. Aqueous ammonia was added to the reaction mixture at room temperature and the solvent was evaporated under reduced pressure. The residue was subjected to silica gel column chromatography (eluent, methanol:ethyl acetate=1:10) for purification to give the title compound (110 mg) as a colorless powder.
¹H-NMR (DMSO-d₆)δ: 7.88 (1H, s), 8.31 (1H, s), 8.67 (1H, s), 9.20 (1H, brs), 9.27 (1H, brs).
IR (KBr): 3398, 3198, 2238, 1663 cm⁻¹.

iii) Production of 5-(aminocarbothionyl)nicotinamide

By the reaction in the same manner as in Example 25-ii) using 5-cyanonicotinamide (80 mg), the title compound (62 mg) was obtained as a yellow powder.
¹H-NMR (DMSO-d₆)δ: 7.73 (1H, s), 8.26 (1H, s), 8.50–8.60 (1H, m), 8.98–9.16 (2H, m), 9.83 (1H, s), 10.19 (1H, s).
IR (KBr): 3137, 1699, 1630, 1410 cm⁻¹.

iv) Production of 5-[4-(4-methylpyridin-3-yl)-1,3-thiazol-2-yl]nicotinamide

By the reaction in the same manner as in Example 25-iii) using 2-bromo-1-(4-methylpyridin-3-yl)ethanone hydrobromate (64 mg) and 5-(aminocarbothionyl)nicotinamide (37 mg), the title compound (16 mg) was obtained as colorless powder crystals.
¹H-NMR (DMSO-d₆)δ: 2.54 (3H, s), 7.39 (1H, d, J=5.1 Hz), 7.80 (1H, s), 8.19 (1H, s), 8.41 (1H, s), 8.48 (1H, d, J=5.1 Hz), 8.75 (1H, t, J=2.3 Hz), 8.87 (1H, s), 9.13 (1H, d, J=2.3 Hz), 9.34 (1H, d, J=2.3 Hz).
IR (KBr): 3316, 3131, 1713, 1420 cm⁻¹.

EXAMPLE 43

Production of N-methyl-5-[4-(4-methylpyridin-3-yl)-1,3-thiazol-2-yl]nicotinamide i) Production of 5-cyano-N-methylnicotinamide By the reaction in the same manner as in Example 30-ii) using 5-bromo-N-methylnicotinamide (3.11 g), tetrakistriphenylphosphinepalladium (160 mg) and zinc cyanide (1.09 g), the title compound (420 mg) was obtained as colorless powder crystals.
¹H-NMR (CDCl₃+CD₃OD)δ: 3.00 (3H, s), 8.49 (1H, t, J=2.1 Hz), 8.96 (1H, d, J=2.1 Hz), 9.18 (1H, d, J=2.1 Hz).
IR (KBr): 3310, 2234, 1651, 1559 cm⁻¹.

ii) Production of 5-(aminocarbonothionyl)-N-methylnicotinamide

By the reaction in the same manner as in Example 25-ii) using 5-cyano-N-methylnicotinamide (380 mg), the title compound (436 mg) was obtained as a pale-green powder.
¹H-NMR (CDCl₃+CD₃OD)δ: 3.00 (3H, s), 8.56 (1H, t, J=2.2 Hz), 9.01 (1H, d, J=2.2 Hz), 9.16 (1H, d, J=2.2 Hz).
IR (KBr): 3330, 3127, 1642, 1287 cm⁻¹.

iii) Production of N-methyl-5-[4-(4-methylpyridin-3-yl)-1,3-thiazol-2-yl]nicotinamide By the reaction in the same manner as in Example 25-iii) using 2-bromo-1-(4-methylpyridin-3-yl)ethanone hydrobromate (470 mg) and 5-(aminocarbonothionyl)-N-methylnicotinamide (238 mg), the title compound (193 mg) was obtained as pale-yellow powder crystals.
¹H-NMR (DMSO-d₆)δ: 2.54 (3H, s), 2.85 (3H, d, J=4.6 Hz), 7.39 (1H, d, J=5.2 Hz), 8.18 (1H, s), 8.48 (1H, d, J=5.2 Hz), 8.72 (1H, t, J=2.2 Hz), 8.80–8.94 (1H, m), 8.86 (1H, s), 9.09 (1H, d, J=2.2 Hz), 9.33 (1H, d, J=2.2 Hz).
IR (KBr): 3233, 1669, 1551, 1435 cm⁻¹.

EXAMPLE 44

Production of N-ethyl-5-[4-(4-methylpyridin-3-yl)-1,3-thiazol-2-yl]nicotinamide i) Production of 5-bromo-N-ethylnicotinamide By the reaction in the same manner as in Example 42-i) using 5-bromonicotinic acid (5.01 g), a solution (25 ml) of ethylamine in THF, 1-ethyl-3-(3-dimethylaminopropyl)-carbodiimide hydrochloride (7.30 g), 1-hydroxy-1H-benzotriazole monohydrate (3.97 g) and triethylamine (5.7 ml), the title compound (2.02 g) was obtained as colorless powder crystals.
¹H-NMR (CDCl₃)δ: 1.28 (3H, t, J=6.3 Hz), 3.40–3.64 (2H, m), 6.14 (1H, brs), 8.26 (1H, t, J=2.2 Hz), 8.78 (1H, d, J=2.2 Hz), 8.85 (1H, d, J=2.2 Hz).
IR (KBr): 3301, 3027, 1640, 1537 cm⁻¹.

ii) Production of 5-cyano-N-ethylnicotinamide

By the reaction in the same manner as in Example 42-ii) using 5-bromo-N-ethylnicotinamide (580 mg) and copper cyanide (350 mg), the title compound (141 mg) was obtained as colorless powder crystals.
¹H-NMR (CDCl₃+CD₃OD)δ: 1.27 (3H, t, J=7.4 Hz), 3.48 (2H, q, J=7.4 Hz), 8.51 (1H, t, J=2.2 Hz), 8.95 (1H, d, J=2.2 Hz), 9.19 (2H, d, J=2.2 Hz).
IR (KBr): 3310, 3054, 2236, 1645, 1549 cm⁻¹.

iii) Production of 5-(N-ethylaminocarbothionyl)nicotinamide

By the reaction in the same manner as in Example 27-ii) using 5-cyano-N-ethylnicotinamide (120 mg), the title compound (99 mg) was obtained as a yellow powder.
¹H-NMR (DMSO-d₆)δ: 1.15 (3H, t, J=7.1 Hz), 3.20–3.44 (2H, m), 8.55 (1H, t, J=2.2 Hz), 8.70–8.84 (1H, m), 9.20–9.12 (2H, m), 9.83 (1H, brs), 10.20 (1H, brs).
IR (KBr): 3285, 3146, 1663, 1545 cm⁻¹.

iv) Production of N-ethyl-5-[4-(4-methylpyridin-3-yl)-1,3-thiazol-2-yl]nicotinamide By the reaction in the same manner as in Example 25-iii) using 2-bromo-1-(4-methylpyridin-3-yl)ethanone hydrobromate (104 mg) and 5-(N-ethylaminocarbothionyl)nicotinamide (70 mg), the title compound (60 mg) was obtained as colorless powder crystals.

$^1$H-NMR (DMSO-d$_6$)δ: 1.17 (3H, t, J=7.2 Hz), 2.54 (3H, s), 320–3.50 (2H, m), 7.39 (1H, d, J=4.8 Hz), 8.19 (1H, s), 8.48 (1H, d, J=4.8 Hz), 8.72 (1H, t, J=2.2 Hz), 8.87 (1H, s), 8.80–8.99 (1H, m), 9.10 (1H, d, J=2.2 Hz), 9.33 (1H, d, J=2.2 Hz).

IR (KBr): 3148, 1738, 1657, 1549 cm$^{-1}$.

EXAMPLE 45

Production of N-methyl-6-[4-(4-methylpyridin-3-yl)-1,3-thiazol-2-yl]pyridine-2-carboxamide i) Production of 6-cyano-N-methylpyridine-2-carboxamide By the reaction in the same manner as in Example 30-ii) using 6-bromo-N-methylpyridine-2-carboxamide (513 mg), tetrakistriphenylphosphinepalladium (70 mg) and zinc cyanide (315 mg), the title compound (200 mg) was obtained as colorless powder crystals.

$^1$H-NMR (CDCl$_3$)δ: 3.06 (3H, d, J=5.1 Hz), 7.07–7.95 (1H, brs), 7.82 (1H, dd, J=1.2, 7.8 Hz), 8.03 (1H, t, J=7.8 Hz), 8.43 (1H, dd, J=1.2, 7.8 Hz).

IR (KBr): 3366, 2247, 1680, 1537 cm$^{-1}$.

ii) Production of 6-(aminocarbonothionyl)-N-methylpyridine-2-carboxamide

By the reaction in the same manner as in Example 25-ii) using 6-cyano-N-methylpyridine-2-carboxamide (192 mg), the title compound (208 mg) was obtained as a yellow powder.

$^1$H-NMR (CDCl$_3$+CD$_3$OD)δ: 3.03 (3H, s), 8.01 (1H, t, J=5.2 Hz), 8.31 (1H, dd, J=0.8, 5.2 Hz), 8.84 (1H, dd, J=0.8, 5.2 Hz).

IR (KBr): 3162, 1651, 1622, 1541, 1456 cm$^{-1}$.

iii) Production of N-methyl-6-[4-(4-methylpyridin-3-yl)-1,3-thiazol-2-yl]pyridine-2-carboxamide By the reaction in the same manner as in Example 25-iii) using 2-bromo-1-(4-methylpyridin-3-yl)ethanone hydrobromate (289 mg) and 6-(aminocarbonothionyl)-N-methylpyridine-2-carboxamide (144 mg), the title compound (121 mg) was obtained as pale-yellow powder crystals.

$^1$H-NMR (CDCl$_3$)δ: 2.56 (3H, s), 3.13 (3H, d, J=3.4 Hz), 7.22–7.27 (1H, m), 7.53 (1H, s), 7.90–8.03 (1H, m), 7.99 (1H, t, J=5.2 Hz), 8.27 (1H, dd, J=0.8, 5.2 Hz), 8.38 (1H, dd, J=0.8, 5.2 Hz), 8.50 (1H, d, J=3.2 Hz), 8.84 (1H, s).

IR (KBr): 3412, 3094, 1676, 1537 cm$^{-1}$.

EXAMPLE 46

Production of N-methyl-6-[4-(4-methylpyridin-3-yl)-1,3-thiazol-2-yl]nicotinamide i) Production of 6-chloro-N-methylnicotinamide By the reaction in the same manner as in Example 42-i) using 6-chloronicotinic acid (5.67 g), a solution (2 M, 25 ml) of methylamine in THF, 1-ethyl-3-(3-dimethylaminopropyl)-carbodiimide hydrochloride (10.30 g), 1-hydroxy-1H-benzotriazole monohydrate (5.90 g) and triethylamine (5.2 ml), the title compound (3.23 g) was obtained as colorless powder crystals.

$^1$H-NMR (CDCl$_3$)δ: 3.03 (3H, d, J=4.8 Hz), 6.53 (1H, brs), 7.41 (1H, d, J=8.4 Hz), 8.10 (1H, dd, J=2.6, 8.4 Hz), 8.74 (1H, d, J=2.6 Hz).

IR (KBr): 3306, 3059, 1651, 1557 cm$^{-1}$.

ii) Production of 6-cyano-N-methylnicotinamide

By the reaction in the same manner as in Example 30-ii) using 6-chloro-N-methylnicotinamide (1.58 g), tetrakistriphenylphosphinepalladium (70 mg) and zinc cyanide (877 mg), the title compound (290 mg) was obtained as colorless powder crystals.

$^1$H-NMR (CDCl$_3$)δ: 3.07 (3H, d, J=4.8 Hz), 6.34 (1H, brs), 7.80 (1H, dd, J=0.6, 8.1 Hz), 8.27 (1H, dd, J=2.2, 8.1 Hz), 9.04 (1H, dd, J=0.6, 2.2 Hz).

IR (KBr): 3293, 3092, 2236, 1645, 1559 cm$^{-1}$.

iii) Production of 6-(aminocarbonothionyl)-N-methylnicotinamide

By the reaction in the same manner as in Example 25-ii) using 6-cyano-N-methylnicotinamide (500 mg), the title compound (480 mg) was obtained as a yellow powder.

$^1$H-NMR (DMSO-d$_6$)δ: 2.82 (3H, d, J=4.4 Hz), 8.32 (1H, dd, J=2.1, 8.4 Hz), 8.55 (1H, d, J=8.4 Hz), 8.70–8.88 (1H, m), 8.97 (1H, d, J=2.1 Hz), 10.03 (1H, brs), 10.29 (1H, brs).

IR (KBr): 3370, 3333, 1640, 1599, 1551 cm$^{-1}$.

iv) Production of N-methyl-6-[4-(4-methylpyridin-3-yl)-1,3-thiazol-2-yl]nicotinamide By the reaction in the same manner as in Example 25-iii) using 2-bromo-1-(4-methylpyridin-3-yl)ethanone hydrobromate (180 mg) and 6-(aminocarbonothionyl)-N-methylnicotinamide (109 mg), the title compound (92 mg) was obtained as a yellow amorphous compound.

$^1$H-NMR (DMSO-d$_6$)δ: 2.54 (3H, s), 2.84 (3H, d, J=4.0 Hz), 7.38 (1H, d, J=5.0 Hz), 8.20 (1H, s), 8.29 (1H, d, J=8.4 Hz), 8.32–8.42 (1H, m), 8.47 (1H, d, J=5.0 Hz), 8.70–8.84 (1H, m), 8.86 (1H, s), 9.05 (1H, t, J=0.9 Hz).

IR (KBr): 3312, 1645, 1593 cm$^{-1}$.

EXAMPLE 47

Production of 4-[4-(4-methylpyridin-3-yl)-1,3-thiazol-2-yl]isoindolin-1-one i) Production of 1-oxo-4-isoindolincarbonitrile By the reaction in the same manner as in Example 30-ii) using 4-bromoisoindolin-1-one (805 mg), tetrakistriphenylphosphinepalladium (140 mg) and zinc cyanide (540 mg), the title compound (250 mg) was obtained as pale-yellow powder crystals.

$^1$H-NMR (DMSO-d$_6$)δ: 4.59 (2H, s), 7.69 (1H, t, J=7.7 Hz), 8.00 (1H, d, J=7.7 Hz), 8.04–8.16 (1H, m), 8.92 (1H, brs).

IR (KBr): 3090, 2230, 1705 cm$^{-1}$.

ii) Production of 4-[4-(4-methylpyridin-3-yl)-1,3-thiazol-2-yl]isoindolin-1-one

By the reaction in the same manner as in Example 25-ii) using 1-oxo-4-isoindolincarbonitrile (310 mg), 1-oxoisoindolin-4-carbothioamide was obtained as pale-green powder. Then, by the reaction in the same manner as in Example 25-iii) using 2-bromo-1-(4-methylpyridin-3-yl)ethanone hydrobromate (520 mg) and 1-oxoisoindolin-4-carbothioamide, the title compound (51 mg) was obtained as colorless powder crystals.

$^1$H-NMR (DMSO-d$_6$)δ: 2.56 (3H, s), 4.79 (2H, s), 7.39 (1H, d, J=5.1 Hz), 7.68 (1H, t, J=7.3 Hz), 7.83 (1H, d, J=7.3 Hz), 8.16 (1H, s), 8.20 (1H, d, J=7.3 Hz), 8.47 (1H, d, J=5.1 Hz), 8.80 (1H, brs), 8.90 (1H, s).

IR (KBr): 3077, 1698, 750 cm$^{-1}$.

EXAMPLE 48

Production of 2-methyl-4-[4-(4-methylpyridin-3-yl)-1,3-thiazol-2-yl]isoindolin-1-one i) Production of 2-methyl-1-oxo-4-isoindolincarbonitrile By the reaction in the same manner as in Example 30-ii) using 4-bromo-2-methylisoindolin-1-one (808 mg), tetrakistriphenylphosphinepalladium (70 mg) and zinc cyanide (340 mg), the title compound (230 mg) was obtained as colorless powder crystals.

$^1$H-NMR (DMSO-d$_6$)δ: 3.10 (3H, s), 4.68 (2H, s), 7.58–7.78 (1H, m), 7.99 (1H, d, J=7.2 Hz), 8.07 (1H, dd, J=0.8, 7.6 Hz).

IR (KBr): 2942, 2234, 1696 cm$^{-1}$.

ii) Production of 2-methyl-4-[4-(4-methylpyridin-3-yl)-1,3-thiazol-2-yl]isoindolin-1-one By the reaction in the same manner as in Example 25-ii) using 2-methyl-1-oxo-4-isoindolincarbonitrile (364 mg), crude 2-methyl-1-oxoisoindolin-4-carbothioamide (603 mg) was obtained as a brown powder. Then, by the reaction in the same manner as in Example 25-iii), 2-bromo-1-(4-methylpyridin-3-yl)ethanone hydrobromate (500 mg) and 2-methyl-1-oxoisoindolin-4-carbothioamide (520 mg), the title compound (187 mg) was obtained as colorless powder crystals.

$^1$H-NMR (DMSO-d$_6$)δ: 2.55 (3H, s), 3,14 (3H, s), 4.86 (2H, s), 7.40 (1H, d, J=4.2 Hz), 7.66 (1H, t, J=7.7 Hz), 7.81 (1H, d, J=7.7 Hz), 8.10–8.22 (2H, m), 8.48 (1H, d, J=4.2 Hz), 8.89 (1H, s).

IR (KBr): 3079, 1701, 1468 cm$^{-1}$.

EXAMPLE 49

Production of 5-[4-(4-methylpyridin-3-yl)-1,3-thiazol-2-yl]pyridin-2(1H)-one i) Production of 6-tert-butoxynicotinonitrile By the reaction in the same manner as in Example 30-ii) using 6-bromonicotinonitrile (1.00 g), tetrakistriphenylphosphinepalladium (35 mg) and zinc cyanide (370 mg), the title compound (490 mg) was obtained as colorless needle crystals.

$^1$H-NMR (CDCl$_3$)δ: 1.60 (9H, s), 6.68 (1H, d, J=8.6 Hz), 7.70 (1H, dd, J=2.4, 8.6 Hz), 8.43 (1H, d, J=2.2 Hz).

IR (KBr): 2976, 2230, 1603, 1485 cm$^{-1}$.

ii) Production of 6-tert-butoxy-3-pyridinecarbothioamide

By the reaction in the same manner as in Example 25-ii) using 6-tert-butoxynicotinonitrile (300 mg), the title compound (240 mg) was obtained as pale-yellow plate crystals.

$^1$H-NMR (CDCl$_3$)δ: 1.60 (9H, s), 6.63 (1H, dd, J=0.6, 8.8 Hz), 7.07 (1H, brs), 7.51 (1H, brs), 8.11 (1H, dd, J=2.7, 8.8 Hz), 8.64 (1H, dd, J=0.6, 2.7 Hz).

IR (KBr): 3144, 1620, 1595, 1323 cm$^{-1}$.

iii) 5-[4-(4-methylpyridin-3-yl)-1,3-thiazol-2-yl]pyridin-2(1H)-one

By the reaction in the same manner as in Example 25-iii) using 2-bromo-1-(4-methylpyridin-3-yl)ethanone hydrobromate (188 mg) and 6-tert-butoxy-3-pyridinecarbothioamide (167 mg), the title compound (120 mg) was obtained as colorless powder crystals.

$^1$H-NMR (DMSO-d$_6$)δ: 2.50 (3H, s), 6.49 (1H, d, J=9.6 Hz), 7.35 (1H, d, J=4.8 Hz), 7.90 (1H, s), 8.02 (1H, dd, J=2.7, 9.6 Hz), 8.11 (1H, d, J=2.7 Hz), 8.44 (1H, d, J=4.8 Hz), 8.01 (1H, s).

IR (KBr): 3090, 2768, 1682, 1601 cm$^{-1}$.

EXAMPLE 50

Production of 3-[4-(4-methylpyridin-3-yl)-1,3-thiazol-2-yl]isoquinoline

By the reaction in the same manner as in Example 25-ii) using 3-isoquinolinecarbonitrile (1.07 g), crude isoquinoline-3-carbothioamide (1.26 g) was obtained as a yellow powder. Then, by the reaction in the same manner as in Example 25-iii), the title compound (449 mg) was obtained as colorless powder crystals from 2-bromo-1-(4-methylpyridin-3-yl)ethanone hydrobromate (1.06 g) and isoquinoline-3-carbothioamide (795 mg).

$^1$H-NMR (DMSO-d$_6$)δ: 2.58 (3H, s), 7.40 (1H, d, J=5.1 Hz), 7.71–7.93 (2H, m), 8.12 (1H, s), 8.15–8.26 (2H, m), 8.48 (1H, d, J=5.1 Hz), 8.71 (1H, s), 8.90 (1H, s), 9.42 (1H, s).

IR (KBr): 3092, 1622, 1590, 1578 cm$^{-1}$.

EXAMPLE 51

Production of 1-[4-(4-methylpyridin-3-yl)-1,3-thiazol-2-yl]isoquinoline i) Production of isoquinoline-1-carbothioamide By the reaction in the same manner as in Example 25-ii) using 1-isoquinolinecarbonitrile (1.01 g), the title compound (1.08 g) was obtained as a pale-yellow powder.

$^1$H-NMR (DMSO-d$_6$)δ: 7.60–7.78 (2H, m), 7.84 (1H, d, J=5.6 Hz), 7.99 (1H, d, J=8.3 Hz), 8.26 (1H, d, J=8.3 Hz), 8.43 (1H, d, J=5.6 Hz), 10.00, (1H, brs), 10.43 (1H, brs).

IR (KBr): 3034, 1653, 1426, 835 cm$^{-1}$.

ii) Production of 1-[4-(4-methylpyridin-3-yl)-1,13-thiazol-2-yl]isoquinoline

By the reaction in the same manner as in Example 25-iii) using 2-bromo-1-(4-methylpyridin-3-yl)ethanone hydrobromate (660 mg) and isoquinoline-1-carbothioamide (400 mg), the title compound (244 mg) was obtained as yellow powder crystals.

$^1$H-NMR (DMSO-d$_6$)δ: 2.60 (3H, s), 7.43 (1H, d, J=5.0 Hz), 7.80–7.96 (2H, m), 8.02 (1H, d, J=5.6 Hz), 8.05–8.18 (1H, m), 8.23 (1H, s), 8.51 (1H, d, J=5.0 Hz), 8.64 (1H, d, J=5.6 Hz), 8.93 (1H, s), 9.70–9.88 (1H, m).

IR (KBr): 3102, 1553, 1397, 949 cm$^{-1}$.

EXAMPLE 52

Production of 2,4-dimethoxy-5-[4-(4-methylpyridin-3-yl)-1,3-thiazol-2-yl]pyrimidine i) Production of 2,4-dimethoxy-5-pyrimidinecarbonitrile By the reaction in the same manner as in Example 30-ii) using 5-bromo-2,4-dimethoxypyrimidine (4.97 g), tetrakistriphenylphosphinepalladium (200 mg) and zinc cyanide (2.04 mg), the title compound (1.85 g) was obtained as colorless needle crystals.

$^1$H-NMR (CDCl$_3$)δ: 4.08, (3H, s), 4.12 (3H, s), 8.54 (1H, s).

IR (KBr): 2971, 2236, 1601, 1541 cm$^{-1}$.

ii) Production of 2,4-dimethoxy-5-[4-(4-methylpyridin-3-yl)-1,3-thiazol-2-yl]pyrimidine By the reaction in the same manner as in Example 25-ii) using 2,4-dimethoxy-5-pyrimidinecarbonitrile (1.32 g), crude 2,4-dimethoxypyrimidine-5-carbothioamide (1.92 g) was obtained as a brown powder. Then, by the reaction in the same manner as in Example 25-iii) using 2-bromo-1-(4-methylpyridin-3-yl)ethanone hydrobromate (1.07 g) and 2,4-dimethoxypyrimidine-5-carbothioamide (880 mg), the title compound (235 mg) was obtained as colorless powder crystals.

$^1$H-NMR (CDCl$_3$)δ: 2.55 (3H, s), 4.01 (3H, s), 4.24 (3H, s), 7.22 (1H, d, J=5.2 Hz), 7.44 (1H, s), 8.47 (1H, d, J=5.2 Hz), 8.81 (1H, s), 9.30 (1H, s).

IR (KBr): 3019, 1601, 1561 cm$^{-1}$.

EXAMPLE 53

Production of 3-[5-methyl-4-(4-methylpyridin-3-yl)-1,3-thiazol-2-yl]benzamide i) Production of 1-(4-methylpyridin-3-yl)propan-1-one A solution of 4-methylnicotinonitrile (5.90 g) in diethyl ether (75 ml) was cooled to 5° C. and an ethylmagnesium bromide diethyl ether solution (3.0M, 25 ml) was gradually added thereto. The reaction mixture was heated under reflux for 2 hrs. and added to 1N hydrochloric acid (200 ml). The mixture was stirred at room temperature for 30 min. Sodium bicarbonate was added to neutralize the reaction mixture, and the mixture was extracted with ethyl acetate. The organic layer was dried and concentrated, and the residue was subjected to silica gel column chromatography (eluent, hexane:ethyl acetate=3:1–2:1) for purification to give the title compound (5.07 g) as a pale-red oil.

$^1$H-NMR (CDCl$_3$)δ: 1.23 (3H, t, J=7.3 Hz), 2.54 (3H, s), 2.98 (2H, q, J=7.3 Hz), 7.19 (1H, d, J=5.1 Hz), 8.54 (1H, d, J=5.1 Hz), 8.91 (1H, s).

IR (KBr): 2978, 1692, 1591 cm$^{-1}$.

ii) Production of 2-bromo-1-(4-methylpyridin-3-yl)propane-1-one hydrobromate

To a solution of 1-(4-methylpyridin-3-yl)propan-1-one (4.72 g) in acetic acid (35 ml) was added hydrobromic acid (5.5 ml) and the mixture was cooled to 10° C. A solution of bromine (5.0 g) in acetic acid (15 ml) was gradually added to the reaction mixture and the mixture was stirred at 80° C. for one hr. The solvent was evaporated under reduced pressure and the residue was recrystallized from ethyl acetate to give the title compound (5.56 g) as a pale-yellow powder.

$^1$H-NMR (DMSO-d$_6$)δ: 1.82 (3H, d, J=6.6 Hz), 2.60 (3H, s), 5.81 (1H, q, J=6.6 Hz), 7.95 (1H, d, J=5.7 Hz), 8.88 (1H, d, J=5.7 Hz), 9.30 (1H, brs).

IR (KBr): 2573, 1705, 1636, 1595 cm$^{-1}$.

iii) Production of 3-[5-methyl-4-(4-methylpyridin-3-yl)-1,3-thiazol-2-yl]benzamide By the reaction in the same manner as in Example 25-iii) using 2-bromo-1-(4-methylpyridin-3-yl)propan-1-one hydrobromate (379 mg) and 3-(aminocarbonothionyl)benzamide (216 mg), the title compound (242 mg) was obtained as colorless powder crystals.

$^1$H-NMR (DMSO-d$_6$)δ: 2.28 (3H, s), 2.41 (3H, s), 7.41 (1H, d, J=5.2 Hz), 7.53 (1H, brs), 7.59 (1H, t, J=7.8 Hz), 7.96 (1H, d, J=7.8 Hz), 8.06 (1H, d, J=7.8 Hz), 8.20 (1H, brs), 8.34–8.40 (1H, m), 8.47–8.54 (2H, m).

IR (KBr): 3191, 1701, 1672, 1422, 1383 cm$^{-1}$.

EXAMPLE 54

Production of 3-[5-isopropyl-4-(4-methylpyridin-3-yl)-1,3-thiazol-2-yl]benzamide i) Production of 3-methyl-1-(4-methylpyridin-3-yl)butan-1-one A solution of 4-methylnicotinonitrile (5.00 g) in diethyl ether (75 ml) was cooled to 5C and a solution (ca. 0.8 M, 78 ml) of isobutylmagnesium bromide in diethyl ether was gradually added thereto. The mixture was heated under reflux for 24 hrs. and added to 1N hydrochloric acid (400 ml). The mixture was stirred at room temperature for 2 hrs. The reaction mixture was neutralized, and extracted with ethyl acetate. The organic layer was dried and concentrated, and the residue was subjected to silica gel column chromatography (eluent, hexane:ethyl acetate=3:1) for purification to give the title compound (3.20 g) as a pale-yellow oil.

$^1$H-NMR (CDCl$_3$)δ: 0.99 (6H, d, J=6.6 Hz), 2.16–2.40 (1H, m), 2.52 (3H, s), 2.81 (2H, d, J=7.0 Hz), 7.19 (1H, d, J=5.2 Hz), 8.53 (1H, d, J=5.2 Hz), 8.85 (1H, s).

IR (KBr): 2959, 1688, 1591 cm$^{-1}$.

ii) Production of 2-bromo-3-methyl-1-(4-methylpyridin-3-yl)butan-1-one hydrobromate By the reaction in the same manner as in Example 53-ii) using 3-methyl-1-(4-methylpyridin-3-yl)butan-1-one (3.10 g) and bromine (2.68 g), the title compound (3.69 g) was obtained as a pale-yellow powder.

$^1$H-NMR (DMSO-d$_6$)δ: 1.07 (3H, d, J=6.6 Hz), 1.09 (3H, d, J=6.4 Hz), 2.21–2.43 (1H, m), 2.58 (3H, s), 5.70 (1H, d, J=6.6 Hz), 7.92 (1H, d, J=5.9 Hz), 8.88 (1H, d, J=5.9 Hz), 9.31 (1H, s).

IR (KBr): 2710, 1711, 1636, 1588 cm$^{-1}$.

iii) Production of 3-[5-isopropyl-4-(4-methylpyridin-3-yl)-1,3-thiazol-2-yl]benzamide By the reaction in the same manner as in Example 25-iii) using 2-bromo-3-methyl-1-(4-methylpyridin-3-yl)butan-1-one hydrobromate (387 mg) and 3-(aminocarbonothionyl)benzamide (271 mg), the title compound (32 mg) was obtained as a brown amorphous compound.

$^1$H-NMR (CDCl$_3$)δ: 1.30 (6H, d, J=6.6 Hz), 2.30 (3H, s), 2.96–3.16 (1H, m), 5.83 (1H, brs), 6.31 (1H, brs), 7.26 (1H, d, J=5.1 Hz), 7.53 (1H, t, J=7.7 Hz), 7.89 (1H, dt, J=7.7, 1.6 Hz), 8.08 (1H, dt, J=7.7, 1.6 Hz), 8.37 (1H, t, J=1.6 Hz), 8.49 (1H, s), 8.52 (1H, d, J=5.1 Hz).

IR (KBr): 3318, 3191, 2963, 1669, 1387 cm$^{-1}$.

EXAMPLE 55

Production of 3-[5-chloro-4-(4-methylpyridin-3-yl)-1,3-thiazol-2-yl]-N,N-dimethylbenzamide To a solution of 3-[4-(4-methylpyridin-3-yl)-1,3-thiazol-2-yl]-N,N-dimethylbenzamide (400 mg) in DMF (2 ml) was added trichloroisocyanuric acid (120 mg) and the mixture was stirred at room temperature for 30 min. The reaction mixture was diluted with aqueous sodium hydrogen carbonate-ethyl acetate. The organic layer was separated and washed with water, aqueous sodium hydrogen carbonate and saturated brine. The organic layer was dried and concentrated, and the residue was subjected to silica gel column chromatography (eluent, hexane:ethyl acetate=2:1–0:1) for purification to give the title compound (140 mg) as a colorless amorphous compound.

$^1$H-NMR (CDCl$_3$)δ: 2.38 (3H, s), 3.01 (3H, s), 3.14 (3H, s), 7.20–7.30 (1H, m), 7.46–7.55 (2H, m), 7.88–8.00 (2H, m), 8.48 5–8.60 (1H, m), 8.65 (1H, brs).
IR (KBr): 1638, 1595, 1397 cm$^{-1}$.

EXAMPLE 56

Production of 3-[5-methyl-4-(4-methylpyridin-3-yl)-1,3-thiazol-2-yl]benzenesulfonamide By the reaction in the same manner as in Example 25-iii) using 2-bromo-1-(4-methylpyridin-3-yl)propan-1-one hydrobromate (520 mg) and 3-(aminosulfonyl)benzenecarbothioamide (361 mg), the title compound (376 mg) was obtained as colorless powder crystals.
$^1$H-NMR (DMSO-d$_6$)δ: 2.28 (3H, s), 2.41 (3H, s), 7.41 (1H, d, J=4.8 Hz), 7.53 (2H, brs), 7.71 (1H, t, J=8.2 Hz), 7.90 (1H, dt, J=8.4, 1.5 Hz), 8.10 (1H, dt, J=8.4, 1.5 Hz), 8.38 (1H, t, J=1.5 Hz), 8.46–8.56 (2H, m).
IR (KBr): 3177, 1599, 1341, 1159 cm$^{-1}$.

EXAMPLE 57

Production of 4-[5-methyl-4-(4-methylpyridin-3-yl)-1,3-thiazol-2-yl]benzenesulfonamide By the reaction in the same manner as in Example 25-iii) using 2-bromo-1-(4-methylpyridin-3-yl)propan-1-one hydrobromate (510 mg) and 4-(aminosulfonyl)benzenecarbothioamide (355 mg), the title compound (322 mg) was obtained as colorless powder crystals.
$^1$H-NMR (DMSO-d$_6$)δ: 2.28 (3H, s), 2.42 (3H, s), 7.41 (1H, d, J=4.8 Hz), 7.50 (2H, brs), 7.94 (2H, d, J=8.8 Hz), 8.11 (2H, d, J=8.8 Hz), 8.46–8.55 (2H, m).
IR (KBr): 3297, 1341, 1157 cm$^{-1}$.

EXAMPLE 58

Production of 3-{2-[4-methylpyridin-3-yl]-1,3-thiazol-4-yl}benzamide

3-{2-[4-Methylpyridin-3-yl]-1,3-thiazol-4-yl}benzonitrile (100 mg) was dissolved in conc. hydrochloric acid (4 ml) and the mixture was stirred at 40° C. for 16 hrs. The reaction mixture was added to aqueous sodium hydrogen carbonate and extracted with ethyl acetate. The organic layer was dried and concentrated. The residue was recrystallized from ethyl acetate-methanol to give the title compound (72 mg) as pale-yellow powder crystals.
$^1$H-NMR (DMSO-d$_6$)δ: 2.68 (3H, s), 7.40–7.68 (3H, m), 7.88 (1H, d, J=8.4 Hz), 8.12 (1H, brs), 8.20 (1H, d, J=7.6 Hz), 8.40 (1H, s), 8.48–8.63 (2H, m), 9.01 (1H, s).
IR (KBr): 3380, 3191, 1655, 1406 cm$^{-1}$.

EXAMPLE 59

Production of 3-{2-[4-(trifluoromethyl)pyridin-3-yl]-1,3-thiazol-4-yl}benzamide

By the reaction in the same manner as in Example 58 using 3-{2-[4-(trifluoromethyl)pyridin-3-yl]-1,3-thiazol-4-yl}benzonitrile (730 mg), the title compound (404 mg) was obtained as colorless powder crystals.
$^1$H-NMR (DMSO-d$_6$)δ: 7.47 (1H, brs), 7.57 (1H, t, J=7.8 Hz), 7.87 (1H, d, J=7.8 Hz), 8.00 (1H, d, J=5.3 Hz), 8.08 (1H, brs), 8.16 (1H, d, J=7.8 Hz), 8.48–8.54 (2H, m), 9.03 (1H, d, J=5.3 Hz), 9.14 (1H, s).
IR (KBr): 3173, 1694, 1146 cm$^{-1}$.

EXAMPLE 60

Production of 2-fluoro-5-{2-[4-(trifluoromethyl)pyridin-3-yl]-1,3-thiazol-4-yl}benzamide 2-Fluoro-5-{2-[4-(trifluoromethyl)pyridin-3-yl]-1,3-thiazol-4-yl}benzoic acid (205 mg) was dissolved in THF (5 ml) and thionyl chloride (0.06 ml) and DMF (0.01 ml) were added. The mixture was heated under reflux for 2 hrs. The reaction mixture was concentrated under reduced pressure and re-dissolved in THF (5 ml). 28% Aqueous ammonia (3 ml) cooled to 5° C. was gradually added. The reaction mixture was stirred at room temperature for 30 min. and extracted with ethyl acetate. The organic layer was dried and concentrated. The residue was subjected to silica gel column chromatography (eluent, hexane:ethyl acetate=9:1→ethyl acetate) for purification and recrystallized from ethyl acetate-diisopropyl ether to give the title compound (130 mg) as colorless powder crystals.
$^1$H-NMR (CDCl$_3$)δ: 5.92 (1H, brs), 6.78 (1H, brs), 7.19–7.32 (1H, m), 7.73 (1H, d, J=5.4 Hz), 7.80 (1H, s), 8.20–8.31 (1H, m), 8.62 (1H, dd, J=2.2, 7.4 Hz), 8.91 (1H, d, J=5.4 Hz), 9.06 (1H, s).
IR (KBr): 3193, 1678, 1607, 1144 cm$^{-1}$.

EXAMPLE 61

Production of 2-fluoro-N-methyl-5-{2-[4-(trifluoromethyl)pyridin-3-yl]-1,3-thiazol-4-yl}benzamide By the reaction in the same manner as in Example 60 using 2-fluoro-5-{2-[4-(trifluoromethyl)pyridin-3-yl]-1,3-thiazol-4-yl}benzoic acid (200 mg), thionyl chloride (0.06 ml) and a solution (2 M, 5 ml) of methylamine in THF, the title compound (145 mg) was obtained as colorless powder crystals.
$^1$H-NMR (CDCl$_3$)δ: 3.08 (3H, d, J=4.6 Hz), 6.65–6.90 (1H, m), 7.16–7.30 (1H, m), 7.72 (1H, d, J=5.1 Hz), 7.79 (1H, s), 8.16–8.26 (1H, m), 8.60 (1H, dd, J=2.6, 7.4 Hz), 8.90 (1H, d, J=5.1 Hz), 9.06 (1H, s).
IR (KBr): 3399, 3090, 1657, 1647, 1316 cm$^{-1}$.

EXAMPLE 62

Production of 2-fluoro-N,N-dimethyl-5-{2-[4-(trifluoromethyl)pyridin-3-yl]-1,3-thiazol-4-yl}benzamide By the reaction in the same manner as in Example 60 using 2-fluoro-5-{2-[4-(trifluoromethyl)pyridin-3-yl]-1,3-thiazol-4-yl}benzoic acid (201 mg), thionyl chloride (0.06 ml) and aqueous dimethylamine solution (50%, 5 ml), the title compound (90 mg) was obtained as a colorless amorphous compound.
$^1$H-NMR (CDCl$_3$)δ: 2.99 (3H, s), 3.16 (3H, s), 7.19 (1H, t, J=8.8 Hz), 7.68 (1H, s), 7.7.2 (1H, d, J=5.0 Hz), 7.92–8.10 (2H, m), 8.90 (1H, d, J=5.0 Hz), 9.04 (1H, s).
IR (KBr): 1644, 1483, 1319, 1159 cm$^{-1}$.

EXAMPLE 63

Production of N-ethyl-2-fluoro-5-{2-[4-(trifluoromethyl)pyridin-3-yl]-1,3-thiazol-4-yl}benzamide By the reaction in the same manner as in Example 60 using 2-fluoro-5-{2-[4-(trifluoromethyl)pyridin-3-yl]-1,3-thiazol-4-yl}benzoic acid (202 mg), thionyl chloride (0.06 ml) and aqueous ethylamine solution (70%, 5 ml), the title compound (139 mg) was obtained as colorless powder crystals.

$^1$H-NMR (CDCl$_3$)δ: 1.29 (3H, t, J=7.2 Hz), 3.48–3.66 (2H, m), 6.74 (1H, brs), 7.14–7.30 (1H, m), 7.72 (1H, d, J=5.1 Hz), 7.78 (1H, s), 8.14–8.26 (1H, m), 8.59 (1H, dd, J=2.4, 7.6 Hz), 8.90 (1H, d, J=5.1 Hz), 9–0.06 (1H, s).

IR (KBr): 3295, 1636, 1325 cm$^{-1}$.

EXAMPLE 64

Production of 3-[4-(4-ethylpyridin-3-yl)-1,3-thiazol-2-yl]benzamide i) Production of 4-ethylnicotinonitrile A solution of diisopropylamine (9.1 ml) in THF (50 ml) was cooled to −30° C. and an n-butyllithium hexane solution (1.61 M, 37 ml) was added. The mixture was stirred for 30 min. After cooling the reaction mixture to −78° C., a solution of 4-methylnicotinonitrile (7.01 g) in THF (50 ml) was added dropwise and the mixture was stirred for 15 min. Methyl iodide (9.1 ml) was added and the mixture was heated to −40° C., and saturated aqueous ammonium chloride solution was added. The reaction mixture was extracted with ethyl acetate and the organic layer was dried and concentrated. The residue was subjected to silica gel column chromatography (eluent, hexane:ethyl acetate=1:1) for purification to give the title compound (6.67 g) as a pale-yellow oil.

$^1$H-NMR (CDCl$_3$)δ: 1.34 (3H, t, J=7.7 Hz), 2.89 (2H, q, J=7.7 Hz), 7.31 (1H, d, J=5.2 Hz), 8.69 (1H, d, J=5.2 Hz), 8.80 (1H, s).

IR (KBr): 2976, 2230, 1591, 1406 cm$^{-1}$.

ii) Production of 1-(4-ethylpyridin-3-yl)ethanone

Magnesium (7.90 g) was suspended in t-butylmethyl ether (300 ml) and iodine (20 mg) was added. Methyl iodide (20 ml) was added dropwise while maintaining the mixture at not higher than 25° C. The mixture was stirred at room temperature for 3 hrs. to give a solution of methylmagnesium iodide in t-butylmethyl ether. To a solution of 4-ethylnicotinonitrile (2.00 g) in toluene (30 ml), which was cooled to −10° C., was gradually added a solution (45 ml) of methylmagnesium iodide in t-butylmethyl ether and the mixture was stirred at room temperature for 12 hrs. The reaction mixture was added to 1N hydrochloric acid (80 ml) and the mixture was stirred at room temperature for 30 min. Sodium bicarbonate was added to neutralize the reaction mixture and the mixture was extracted with ethyl acetate. The organic layer was dried and concentrated. The residue was subjected to silica gel column chromatography (eluent, hexane:ethyl acetate=20:1–1:3) for purification to give the title compound (1.84 g) as a yellow oil.

$^1$H-NMR (CDCl$_3$)δ: 1.23 (3H, t, J=7.4 Hz), 2.64 (3H, s), 2.92 (2H, q, J=7.4 Hz), 7.24 (1H, d, J=5.2 Hz), 8.58 (1H, d, J=5.2 Hz), 8.91 (1H, s).

IR (KBr): 2975, 1688, 1590, 1269 cm$^{-1}$.

iii) Production of 2-bromo-1-(4-ethylpyridin-3-yl)ethanone hydrobromate

By the reaction in the same manner as in Example 53-ii) using 1-(4-ethylpyridin-3-yl)ethanone (1.68 g) and bromine (1.60 g), the title compound (1.95 g) was obtained as a pale-brown powder.

$^1$H-NMR (DMSO-d$_6$)δ: 1.21 (3H, t, J=7.5 Hz), 2.90 (2H, q, J=7.5 Hz), 5.03 (2H, s), 7.89 (1H, d, J=5.8 Hz), 8.88 (1H, d, J=5.8 Hz), 9.24 (1H, s).

IR (KBr): 2978, 1713, 1638, 1584 cm$^{-1}$.

iv) Production of 3-[4-(4-ethylpyridin-3-yl)-1,3-thiazol-2-yl]benzamide

By the reaction in the same manner as in Example 25-iii) using 2-bromo-1-(4-ethylpyridin-3-yl)ethanone hydrobromate (161 mg) and 3-(aminocarbonothionyl)benzamide (97 mg), the title compound (81 mg) was obtained as pale-yellow powder crystals.

$^1$H-NMR (DMSO-d$_6$)δ: 1.19 (3H, t, J=7.6 Hz), 2.87 (2H, q, J=7.6 Hz), 7.41 (1H, d, J=5.2 Hz), 7.55 (1H, brs), 7.63 (1H, t, J=8.0 Hz), 8.00 (1H, d, J=8.0 Hz), 8.05 (1H, s), 8.16 (1H, d, J=8.0 Hz), 8.22 (1H, brs), 8.46 (1H, s), 8.52 (1H, d, J=5.2 Hz), 8.74 (1H, s).

IR (KBr): 3152, 1684, 1383 cm$^{-1}$.

EXAMPLE 65

Production of 3-[4-(4-ethylpyridin-3-yl)-1,3-thiazol-2-yl]-N-methylbenzamide

By the reaction in the same manner as in Example 25-iii) using 2-bromo-1-(4-ethylpyridin-3-yl)ethanone hydrobromate (162 mg) and 3-(aminocarbonothionyl)-N-methylbenzamide (110 mg), the title compound (91 mg) was obtained as colorless powder crystals.

$^1$H-NMR (DMSO-d$_6$)δ: 1.18 (3H, t, J=7.5 Hz), 2.82 (3H, d, J=4.8 Hz), 2.88 (2H, q, J=7.5 Hz), 7.40 (1H, d, J=4.8 Hz), 7.63 (1H, t, J=7.8 Hz), 7.96 (1H, d, J=7.8 Hz), 8.04 (1H, s), 8.15 (1H, d, J=7.8 Hz), 8.42 (1H, s), 8.52 (1H, d, J=4.8 Hz), 8.63–8.73 (1H, m), 8.73 (1H, s).

IR (KBr): 3266, 3189, 1669 cm$^{-1}$.

EXAMPLE 66

Production of 3-[4-(4-ethylpyridin-3-yl)-1,3-thiazol-2-yl]-N,N-dimethylbenzamide By the reaction in the same manner as in Example 25-iii) using 2-bromo-1-(4-ethylpyridin-3-yl)ethanone hydrobromate (163 mg) and 3-(aminocarbonothionyl)-N,N-dimethylbenzamide (110 mg), the title compound (110 mg) was obtained as a pale-brown oil.

$^1$H-NMR (DMSO-d$_6$)δ: 1.18 (3H, t, J=7.2 Hz), 2.87 (2H, q, J=7.2 Hz), 2.95 (3H, s), 3.02 (3H, s), 7.40 (1H, d, J=5.1 Hz), 7.54 (1H, dd, J=1.1, 7.5 Hz), 7.61 (1H, t, J=7.5 Hz), 7.99 (1H, d, J=1.1 Hz), 8.03–8.14 (2H, m), 8.52 (1H, d, J=5.1 Hz), 8.73 (1H, s).

IR (KBr): 2969, 1634, 1395 cm$^{-1}$.

EXAMPLE 67

Production of 3-[4-(4-isopropylpyridin-3-yl)-1,3-thiazol-2-yl]benzamide i) Production of 4-isopropylnicotinonitrile By the reaction in the same manner as in Example 64-i) using 4-ethylnicotinonitrile (2.95 g) and methyl iodide (7 ml), the title compound (1.90 g) was obtained as a yellow oil.

$^1$H-NMR (CDCl$_3$)δ: 1.35 (6H, d, J=6.6 Hz), 3.22–3.46 (1H, m), 7.36 (1H, d, J=5.2 Hz), 8.72 (1H, d, J=5.2 Hz), 8.80 (1H, s).

IR (KBr): 2971, 2228, 1588, 1406 cm$^{-1}$.

ii) Production of 1-(4-isopropylpyridin-3-yl)ethanone

By the reaction in the same manner as in Example 64-i) using 4-isopropylnicotinonitrile (1.40 g) and solution (ca.

1.0 M, 30 ml) of methylmagnesium iodide in t-butyl methyl ether, the title compound (0.94 g) was obtained as a yellow oil.

$^1$H-NMR (CDCl$_3$)δ: 1.24 (6H, d, J=6.6 Hz), 2.64 (3H, s), 3.46–3.70 (1H, m), 7.34 (1H, d, J=5.0 Hz), 8.60 (1H, d, J=5.0 Hz), 8.79 (1H, s).

IR (KBr): 2969, 1690, 1588, 1267 cm$^{-1}$.

iii) Production of 3-[4-(4-isopropylpyridin-3-yl)-1,3-thiazol-2-yl]benzamide

By the reaction in the same manner as in Example 53-ii) using 1-(4-isopropylpyridin-3-yl)ethanone (0.90 g) and bromine (0.63 g), crude 2-bromo-1-(4-isopropylpyridin-3-yl)ethanone hydrobromate (1.70 g) was obtained as a pale-brown amorphous compound. Then, by the reaction in the same manner as in Example 25-iii) using 2-bromo-1-(4-isopropylpyridin-3-yl)ethanone hydrobromate (340 mg) and 3-(aminocarbonothionyl)benzamide (240 mg), the title compound (59 mg) was obtained as colorless powder crystals.

$^1$H-NMR (DMSO-d$_6$)δ: 1.23 (6H, d, J=6.2 Hz), 3.20–3.60 (1H, m), 7.42–7.70 (3H, m), 8.00 (2H, s), 8.07–8.28 (2H, m), 8.38–8.68 (3H, m).

IR (KBr): 3104, 1703, 1420, 1387 cm$^{-1}$.

EXAMPLE 68

Production of 3-[4-(4-isopropylpyridin-3-yl)-1,3-thiazol-2-yl]-N,4-dimethylbenzamide By the reaction in the same manner as in Example 25-iii) using 2-bromo-1-(4-isopropylpyridin-3-yl)ethanone hydrobromate (343 mg) and 3-(aminocarbonothionyl)-N,4-dimethylbenzamide (250 mg), the title compound (25 mg) was obtained as a pale-yellow amorphous compound.

$^1$H-NMR (CDCl$_3$)δ: 1.25 (6H, d, J=7.0 Hz), 2.67 (3H, s), 3.01 (3H, d, J=4.8 Hz), 3.40–3.68 (1H, m), 6.58–6.76 (1H, brs), 7.20–7.48 (3H, m), 7.75 (1H, dd, J=1.8, 8.0 Hz), 8.21 (1H, d, J=1.8 Hz), 8.55 (1H, d, J=5.2 Hz), 8.65 (1H, s).

IR (KBr): 3285, 2967, 1645, 1557 cm$^{-1}$.

EXAMPLE 69

Production of 3-[4-(4-isopropylpyridin-3-yl)-1,3-thiazol-2-yl]-N,N-dimethylbenzamide hemifumarate After the reaction in the same manner as in Example 25-iii) using 2-bromo-1-(4-isopropylpyridin-3-yl)ethanone hydrobromate (342 mg) and 3-(aminocarbonothionyl)-N,N-dimethylbenzamide (320 mg), a fumaric acid treatment was applied to give the title compound (100 mg) as colorless powder crystals.

$^1$H-NMR (DMSO-d$_6$)δ: 1.22 (6H, d, J=6.6 Hz), 2.95 (3H, s), 3.02 (3H, s), 3.20–3.60 (1H, m), 6.63 (1H, s), 7.46–7.65 (3H, m), 7.92–8.09 (3H, m), 8.57 (1H, d, J=5.4 Hz), 8.63 (1H, s).

IR (KBr): 3083, 1705, 1657 cm$^{-1}$.

EXAMPLE 70

Production of 3-[4-(4-ethylpyridin-3-yl)-1,3-thiazol-2-yl]benzenesulfonamide

By the reaction in the same manner as in Example 25-iii) using 2-bromo-1-(4-ethylpyridin-3-yl)ethanone hydrobromate (161 mg) and 3-(aminosulfonyl)benzenecarbothioamide (110 mg), the title compound (67 mg) was obtained as colorless powder crystals.

$^1$H-NMR (DMSO-d$_6$)δ: 1.18 (3H, t, J=7.5 Hz), 2.87 (2H, q, J=7.5 Hz), 7.41 (1H, d, J=5.0 Hz), 7.55 (2H, brs), 7.75 (1H, t, J=7.9 Hz), 7.94 (1H, dt, J=7.9, 1.6 Hz), 8.09 (1H, s), 8.21 (1H, dt, J=7.9, 1.6 Hz), 8.45 (1H, t, J=1.6 Hz), 8.53 (1H, d, J=5.0 Hz), 8.74 (1H, s).

IR (KBr): 3270, 1599, 1460, 1341, 1154 cm$^{-1}$.

EXAMPLE 71

Production of 4-[4-(4-ethylpyridin-3-yl)-1,3-thiazol-2-yl]benzenesulfonamide

By the reaction in the same manner as in Example 25-iii) using 2-bromo-1-(4-ethylpyridin-3-yl)ethanone hydrobromate (161 mg) and 4-(aminosulfonyl)benzenecarbothioamide (109 mg), the title compound (90 mg) was obtained as colorless powder crystals.

$^1$H-NMR (DMSO-d$_6$)δ: 1.19 (3H, t, J=7.5 Hz), 2.88 (2H, q, J=7.5 Hz), 7.41 (1H, d, J=4.8 Hz), 7.52 (2H, brs), 7.96 (2H, d, J=8.4 Hz), 8.11 (1H, s), 8.20 (2H, d, J=8.4 Hz), 8.53 (1H, d, J=4.8 Hz), 8.74 (1H, s).

IR (KBr): 3291, 1597, 1399, 1333, 1159 cm$^{-1}$.

EXAMPLE 72

Production of 4-methyl-3-[2-(2-methyl-5-nitrophenyl)-1,3-thiazol-4-yl]pyridine i) Production of 2-methyl-5-nitrobenzonitrile By the reaction in the same manner as in Example 30-ii) using 2-bromo-4-nitrotoluene (12.03 g), tetrakistriphenylphosphinepalladium (300 mg) and zinc cyanide (4.22 g), the title compound (1.36 g) was obtained as pale-yellow powder crystals.

$^1$H-NMR (CDCl$_3$)δ: 2.69 (3H, s), 7.54 (1H, d, J=8.4 Hz), 8.34 (1H, dd, J=2.6, 8.4 Hz), 8.48 (1H, d, J=2.6 Hz).

IR (KBr): 3077, 2236, 1615, 1524 cm$^{-1}$.

ii) Production of 4-methyl-3-[2-(2-methyl-5-nitrophenyl)-1,3-thiazol-4-yl]pyridine By the reaction in the same manner as in Example 25-ii) using 2-methyl-5-nitrobenzonitrile (1.25 g), 2-methyl-5-nitrobenzenecarbothioamide was obtained as a yellow powder. Then, by the reaction in the same manner as in Example 25-iii) using 2-bromo-1-(4-methylpyridin-3-yl)ethanone hydrobromate (1.35 g) and 2-methyl-5-nitrobenzenecarbothioamide, the title compound (460 mg) was obtained as colorless needle crystals.

$^1$H-NMR (CDCl$_3$)δ: 2.56 (3H, s), 2.78 (3H, s), 7.24 (1H, d, J=5.0 Hz), 7.46–7.57 (2H, m), 8.20 (1H, dd, J=2.3, 8.4 Hz), 8.49 (1H, d, J=5.0 Hz), 8.67 (1H, d, J=2.3 Hz), 8.84 (1H, s).

IR (KBr): 3038, 1530, 1343 cm$^{-1}$.

EXAMPLE 73

Production of 3-{2-[4-methylpyridin-3-yl]-1,3-thiazol-4-yl}benzonitrile i) Production of 3-(bromoacetyl)benzonitrile 3-Acetylbenzonitrile (5.33 g) and copper(II) bromide (16.40 g) were suspended in ethyl acetate (100 ml) and the mixture was heated under reflux for 2 hrs. After cooling the reaction mixture, the insoluble material was filtered off and the filtrate was washed with aqueous sodium hydrogen carbonate and saturated brine. The organic layer was dried and concentrated and the residue was recrystallized from ethyl acetate-diisopropyl ether to give the title compound (4.29 g) as colorless powder crystals.

$^1$H-NMR (CDCl$_3$)δ: 2.82 (2H, s), 6.06 (1H, t, J=7.8 Hz), 6.29 (1H, d, J=7.8 Hz), 6.57–6.72 (2H, m).

IR (KBr): 3104, 2942, 2230, 1709, 1599 cm$^{-1}$.

ii) Production of 3-{2-[4-methylpyridin-3-yl]-1,3-thiazol-4-yl}benzonitrile

By the reaction in the same manner as in Example 25-iii) using 3-(bromoacetyl)benzonitrile (599 mg) and 4-methylpyridine-3-thiocarboxamide (403 mg), the title compound (302 mg) was obtained as pale-yellow powder crystals.

$^1$H-NMR (DMSO-d$_6$)δ: 2.67 (3H, s), 7.46 (1H, d, J=5.2 Hz), 7.71 (1H, t, J=8.0 Hz), 7.85 (1H, d, J=8.0 Hz), 8.39 (1H, d, J=8.0 Hz), 8.50 (1H, s), 8.55 (1H, d, J=5.2 Hz), 8.56 (1H, s), 9.00 (1H, s).

IR (KBr): 3104, 2230, 1593, 1485 cm$^{-1}$.

EXAMPLE 74

Production of 3-{2-[4-(trifluoromethyl)pyridin-3-yl]-1,3-thiazol-4-yl}benzonitrile By the reaction in the same manner as in Example 25-iii) using 3-(bromoacetyl)benzonitrile (913 mg) and 4-trifluoromethylpyridine-3-thiocarboxamide (840 mg), the title compound (1.03 g) was obtained as colorless powder crystals.

$^1$H-NMR (CDCl$_3$)δ: 7.52–7.70 (2H, m), 7.74 (1H, d, J=5.2 Hz), 7.80 (1H, s), 8.16–8.30 (2H, m), 8.93 (1H, d, J=5.2 Hz), 9.05 (1H, s).

IR (KBr): 3088, 2230, 1316, 1130 cm$^{-1}$.

EXAMPLE 75

Production of 3-[4-(3-bromo-4-fluorophenyl)-1,3-thiazol-2-yl]-4-(trifluoromethyl)pyridine i) Production of 2-bromo-1-(3-bromo-4-fluorophenyl)ethanone By the reaction in the same manner as in Example 73-i) using 3'-bromo-4'-fluoroacetophenone (8.00 g) and copper (II) bromide (16.50 g), the title compound (10.60 g) was obtained as a pale-yellow oil.

$^1$H-NMR (CDCl$_3$)δ: 4.39 (2H, s), 7.20–7.28 (1H, m), 7.90–7.99 (1H, m), 8.23 (1H, dd, J=2.1, 6.6 Hz).

IR (KBr): 1684, 1591, 1281, 1264 cm$^{-1}$.

ii) Production of 3-[4-(3-bromo-4-fluorophenyl)-1,3-thiazol-2-yl]-4-(trifluoromethyl)pyridine By the reaction in the same manner as in Example 25-iii) using 2-bromo-1-(3-bromo-4-fluorophenyl)ethanone (3.10 g) and 4-trifluoromethylpyridine-3-thiocarboxamide (1.87 g), the title compound (1.50 g) was obtained as brown needle crystals.

$^1$H-NMR (CDCl$_3$)δ: 7.20 (1H, t, J=8.5 Hz), 7.66 (1H, s), 7.73 (1H, d, J=5.2 Hz), 7.84–7.94 (1H, m), 8.18 (1H, dd, J=2.2, 6.6 Hz), 8.91 (1H, d, J=5.2 Hz), 9.04 (1H, s).

IR (KBr): 3063, 1472, 1319, 1127 cm$^{-1}$.

EXAMPLE 76

Production of ethyl 2-fluoro-5-{2-[4-(trifluoromethyl)pyridin-3-yl]-1,3-thiazol-4-yl}benzoate 3-[4-(3-Bromo-4-fluorophenyl)-1,3-thiazol-2-yl]-4-(trifluoromethyl)pyridine (1.48 g), 1,1'-bis(diphenylphosphino) ferrocene (680 mg), palladium acetate (270 mg) and triethylamine (0.77 ml) were suspended in a mixture of ethanol (15 ml)/THF (15 ml), and the mixture was vigorously stirred at 70° C. for 3 hrs at 5 atm under a carbon monoxide atmosphere. The reaction mixture was added to water and extracted with ethyl acetate. The organic layer was dried and concentrated. The residue was subjected to silica gel column chromatography (eluent, hexane:ethyl acetate=19:1–1:1) for purification and recrystallized from ethyl acetate-diisopropyl ether to give the title compound (1.17 g) as colorless powder crystals.

$^1$H-NMR (CDCl$_3$)δ: 1.43 (3H, t, J=7.1 Hz), 4.44 (2H, q, J=7.1 Hz), 7.18–7.30 (1H, m), 7.73 (1H, d, J=5.0 Hz), 7.73 (1H, s), 8.12–8.22 (1H, m), 8.49 (1H, dd, J=2.2, 7.0 Hz), 8.91 (1H, d, J=5.0 Hz), 9.06 (1H, s).

IR (KBr): 1728, 1318, 1291, 1146 cm$^{-1}$.

EXAMPLE 77

Production of 2-fluoro-5-{2-[4-(trifluoromethyl)pyridin-3-yl]-1,3-thiazol-4-yl}benzoic acid Ethyl 2-fluoro-5-{2-[4-(trifluoromethyl)pyridin-3-yl]-1,3-thiazol-4-yl}benzoate (1.00 g) was suspended in a mixture of ethanol (20 ml)/1N NaOH (5 ml) and the mixture was stirred at room temperature for one hr. 1N Hydrochloric acid (5 ml) was added to the reaction mixture, and the precipitated crystals were collected by filtration and washed with water to give the title compound (0.86 g) as a pale-brown powder.

$^1$H-NMR (DMSO-d$_6$)δ: 7.40–7.60 (1H, m), 8.00 (1H, d, J=5.2 Hz), 8.20–8.38 (1H, m), 8.46–8.70 (2H, m), 9.03 (1H, d, J=5.2 Hz), 9.13 (0.1H, s).

IR (KBr): 1717, 1318, 1159 cm$^{-1}$.

EXAMPLE 78

Production of 4-methyl-3-[2-(4-methyl-pyridin-3-yl)-1,3-thiazol-4-yl]pyridine

By the reaction in the same manner as in Example 25-iii) using 2-bromo-1-(4-methylpyridin-3-yl)ethanone hydrobromate (392 mg) and 4-methylpyridine-3-thiocarboxamide (152 mg), the title compound (112 mg) was obtained as colorless powder crystals.

$^1$H-NMR (CDCl$_3$)δ: 2.56 (3H, s), 2.70 (3H, s), 7.20–7.30 (2H, m), 7.50 (1H, s), 8.49 (1H, d, J=5.1 Hz), 8.53 (1H, d, J=5.1 Hz), 8.84 (1H, s), 8.98 (1H, s).

IR (KBr): 3071, 1593, 1491, 1399 cm$^{-1}$.

EXAMPLE 79

Production of 4-methyl-3-[4-(pyridin-4-yl)-1,3-thiazol-2-yl]pyridine

By the reaction in the same manner as in Example 25-iii) using 2-bromo-1-(pyridin-4-yl)ethanone hydrobromate (460 mg) and 4-methylpyridine-3-thiocarboxamide (248 mg), the title compound (99 mg) was obtained as colorless powder crystals.

$^1$H-NMR (CDCl$_3$)δ: 2.72 (3H, s), 7.28 (1H, d, J=5.0 Hz), 7.80–7.90 (3H, m), 8.54 (1H, d, J=5.0 Hz), 8.64–8.74 (2H, m), 8.98 (1H, s).

IR (KBr): 1599, 1483, 1209 cm$^{-1}$ cm$^{-1}$.

EXAMPLE 80

Production of N-methyl-3-[2-(4-methylpyridin-3-yl)-1,3-thiazol-4-yl]benzamide i) Production of ethyl 3-acetylbenzoate By the reaction in the same manner as in Example 76 using 3-bromoacetophenone (48.50 g), 1,1'-bis (diphenylphosphino)ferrocene (3.60 mg), palladium acetate (1.30 g) and triethylamine (68 ml), the title compound (45.3 g) was obtained as colorless needle crystals.

$^1$H-NMR (CDCl$_3$)δ: 1.43 (3H, t, J=7.2 Hz), 2.67 (3H, s), 4.42 (2H, q, J=7.2 Hz), 7.56 (1H, t, J=7.8 Hz), 8.15 (1H, dt, J=7.8, 1.6 Hz), 8.25 (1H, dt, J=7.8, 1.6 Hz), 8.60 (1H, t, J=1.6 Hz).

IR (KBr): 1723, 1692, 1302, 1236 cm$^{-1}$.

ii) Production of ethyl 3-(bromoacetyl)benzoate

By the reaction in the same manner as in Example 73-i) using ethyl 3-acetylbenzoate (30.0 g) and copper(II) bromide (67.5 g), a crude title compound (42.0 g) was obtained as a brown oil.

$^1$H-NMR (CDCl$_3$)δ: 1.43 (3H, t, J=7.2 Hz), 4.43 (2H, q, J=7.2 Hz), 4.50 (2H, s), 7.60 (1H, t, J=8.0 Hz), 8.18 (1H, dt, J=8.0, 1.6 Hz), 8.29 (1H, dt, J=8.0, 1.6 Hz), 8.62 (1H, t, J=1.6 Hz).

IR (KBr): 1721, 1688, 1304, 1246 cm$^{-1}$.

iii) Production of ethyl 3-[2-(4-methylpyridin-3-yl)-1,3-thiazol-4-yl]benzoate

By the reaction in the same manner as in Example 25-iii) using ethyl 3-(bromoacetyl)benzoate (18.10 g) and 4-methylpyridine-3-thiocarboxamide (8.11 g), the title compound (6.50 g) was obtained as pale-yellow powder crystals.

$^1$H-NMR (CDCl$_3$)δ: 1.43 (3H, t, J=7.1 Hz), 2.73 (3H, s), 4.43 (2H, q, J=7.1 Hz), 7.25–7.30 (1H, m), 7.54 (1H, t, J=7.8 Hz), 7.71 (1H, s), 8.05 (1H, dt, J=7.8, 1.2 Hz), 8.19–8.26 (1H, m), 8.53 (1H, d, J=4.8 Hz), 8.58–8.64 (1H, m), 9.00 (1H, s).

IR (KBr): 3059, 1713, 1285 cm$^{-1}$.

iv) Production of 3-[2-(4-methylpyridin-3-yl)-1,3-thiazol-4-yl]benzoic acid

By the reaction in the same manner as in Example 77 using ethyl 3-[2-(4-methylpyridin-3-yl)-1,3-thiazol-4-yl]benzoate (6.50 g) and 1N NaOH (80 ml), the title compound (5.27 g) was obtained as a colorless powder.

$^1$H-NMR (DMSO-d$_6$)δ: 2.68 (3H, s), 7.47 (1H, d, J=5.0 Hz), 7.63 (1H, t, J=7.8 Hz), 7.96 (1H, d, J=7.8 Hz), 8.30 (1H, d, J=7.8 Hz), 8.49 (1H, s), 8.55 (1H, d, J=5.0 Hz), 8.58–8.64 (1H, m), 8.99 (1H, s).

IR (KBr): 3088, 1703, 1601, 1292 cm$^{-1}$.

v) Production of N-methyl-3-[2-(4-methylpyridin-3-yl)-1,3-thiazol-4-yl]benzamide By the reaction in the same manner as in Example 60 using 3-[2-(4-methyl-pyridin-3-yl)-1,3-thiazol-4-yl]benzoic acid (256 mg), thionyl chloride (0.09 ml) and aqueous methylamine solution (40%, 5 ml), the title compound (191 mg) was obtained as colorless powder crystals.

$^1$H-NMR (DMSO-d$_6$)δ: 2.68 (3H, s), 2.83 (3H, d, J=4.6 Hz), 7.47 (1H, d, J=4.6 Hz), 7.58 (1H, t, J=7.8 Hz), 7.83 (1H, d, J=7.8 Hz), 8.19 (1H, d, J=7.8 Hz), 8.40 (1H, s), 8.49 (1H, s), 8.51–8.63 (2H, m), 9.01 (1H, s).

IR (KBr): 3347, 3086, 1663, 1559 cm$^{-1}$.

EXAMPLE 81

Production of N,N-dimethyl-3-[2-(4-methylpyridin-3-yl)-1,3-thiazol-4-yl]benzamide By the reaction in the same manner as in Example 60 using 3-[2-(4-methylpyridin-3-yl)-1,3-thiazol-4-yl]benzoic acid (248 mg), thionyl chloride (0.09 ml) and aqueous dimethylamine solution (50%, 5 ml), the title compound (200 mg) was obtained as colorless powder crystals.

$^1$H-NMR (CDCl$_3$)δ: 2.71 (3H, s), 3.04 (3H, s), 3.16 (3H, s), 7.24–7.30 (1H, m), 7.38–7.45 (1H, m), 7.50 (1H, t, J=8.1 Hz), 8.02–8.08 (2H, m), 8.52 (1H, d, J=5.4 Hz), 8.98 (1H, s).

IR (KBr): 3079, 1634, 1395 cm$^{-1}$.

EXAMPLE 82

Production of N-ethyl-3-[2-(4-methylpyridin-3-yl)-1,3-thiazol-4-yl]benzamide

By the reaction in the same manner as in Example 60 using 3-[2-(4-methylpyridin-3-yl)-1,3-thiazol-4-yl]benzoic acid (259 mg), thionyl chloride (0.09 ml) and aqueous ethylamine solution (70%, 5 ml), the title compound (215 mg) was obtained as pale-brown powder crystals.

$^1$H-NMR (DMSO-d$_6$)δ: 1.16 (3H, t, J=7.2 Hz), 2.68 (3H, s), 3.24–3.60 (2H, m), 7.47 (1H, d, J=5.0 Hz), 7.58 (1H, t, J=7.9 Hz), 7.84 (1H, dt, J=7.9, 1.6 Hz), 8.19 (1H, dt, J=7.9, 1.6 Hz), 8.40 (1H, s), 8.49 (1H, t, J=1.6 Hz), 8.55 (1H, d, J=5.0 Hz), 8.54–8.66 (1H, m), 9.01 (1H, s).

IR (KBr): 3308, 2978, 1634, 1545 cm$^{-1}$.

EXAMPLE 83

Production of 3-{4-[3-(1-azetidinylcarbonyl)phenyl]-1,3-thiazol-2-yl}-4-methylpyridine 3-[2-(4-Methylpyridin-3-yl)-1,3-thiazol-4-yl]benzoic acid (238 mg) was suspended in THF (10 ml) and thionyl chloride (0.09 ml) and DMF (0.05 ml) were added. The mixture was heated under reflux for 1 hr. The reaction mixture was concentrated under reduced pressure and re-dissolved in THF (10 ml). To this solution was added a solution of azetidine hydrochloride (0.54 g) dissolved in 1N NaOH (10 ml), and the mixture was stirred at room temperature for 30 min. The reaction mixture extracted with ethyl acetate and the organic layer was dried and concentrated. The obtained residue was subjected to silica gel column chromatography (eluent, ethyl acetate) for purification and recrystallized from ethyl acetate-diisopropyl ether to give the title compound (148 mg) as colorless powder crystals.

$^1$H-NMR (DMSO-d$_6$)δ: 2.28 (2H, quintet, J=7.5 Hz), 2.68 (3H, s), 4.09 (2H, t, J=7.5 Hz), 4.35 (2H, t, J=7.5 Hz), 7.47 (1H, d, J=5.0 Hz), 7.51–7.67 (2H, m), 8.18 (1H, d, J=7.0 Hz), 8.27 (1H, s), 8.47 (1H, s), 8.55 (1H, d, J=5.0 Hz), 8.99 (1H, s).

IR (KBr): 3056, 1634, 1437, 1404 cm$^{-1}$.

FORMULATION EXAMPLE 1

| | |
|---|---|
| (1) compound No. 74 | 50 mg |
| (2) lactose | 34 mg |
| (3) corn starch | 10.6 mg |
| (4) corn starch (paste) | 5 mg |

-continued

| | |
|---|---|
| (5) magnesium stearate | 0.4 mg |
| (6) calcium carboxymethylcellulose | 20 mg |
| total | 120 mg |

According to a conventional method, the above-mentioned (1)-(6) were mixed and tableted using a tableting machine to give tablets.

FORMULATION EXAMPLE 2

| | |
|---|---|
| (1) compound No. 78 | 10 mg |
| (2) lactose | 60 mg |
| (3) corn starch | 35 mg |
| (4) gelatin | 3 mg |
| (5) magnesium stearate | 2 mg |

A mixture of Example compound (10 mg), lactose (60 mg) and corn starch (35 mg) is passed through a 1 mm mesh sieve using a 10% aqueous gelatin solution (0.03 ml) (3 mg as gelatin) to give granules. They are dried at 40° C. and again passed through a sieve. The thus-obtained granules are mixed with magnesium stearate (2.0 mg) and compressed. The resulting core tablets are sugar-coated with an aqueous suspension of sucrose, titanium dioxide, talc and acacia. The tablets subjected to the coating are glazed with bee wax to give coated tablets.

FORMULATION EXAMPLE 3

| | |
|---|---|
| (1) compound No. 154 | 10 mg |
| (2) lactose | 70 mg |
| (3) corn starch | 50 mg |
| (4) soluble starch | 7 mg |
| (5) magnesium stearate | 3 mg |

Example compound (10 mg) and magnesium stearate (3 mg) are granulated with an aqueous solution (0.07 ml) of soluble starch (7 mg as soluble starch), dried, and mixed with lactose (70 mg) and corn starch (50 mg). The mixture is compressed to give tablets.

FORMULATION EXAMPLE 4

| | |
|---|---|
| (1) compound No. 137 | 5 mg |
| (2) salt | 20 mg |
| (3) distilled water | amount to make the total amount 2 ml |

Example compound (5 mg) and salt (20 mg) are dissolved in distilled water, and water is added to the total amount (2 ml). The solution is filtrated and filled in an ampoule (2 ml) under aseptic conditions. The ampoule is sterilized and sealed to give a solution for injection.

FORMULATION EXAMPLE 5

| | |
|---|---|
| (1) compound No. 135 | 10 mg |
| (2) lactose | 90 mg |
| (3) microcrystalline cellulose | 70 mg |
| (4) magnesium stearate | 10 mg |
| per capsule | 180 mg |

The total amount of the above-mentioned (1), (2) and (3) and (5 mg) of (4) were admixed and granulated. Thereto was added the remaining (4) (5 mg) and the whole mixture was sealed in a gelatin capsule.

EXPERIMENTAL EXAMPLE 1

Assay of Steroid $C_{17,20}$-lyase-inhibitory Activity in Rat

The assay was performed according to *The Prostate*, Vol. 26, 140–150 (1995). The orchis was removed from 13-week-old male SD rat. The orchis was homogenized and centrifuged to prepare a microsome. The $[1.2-^3H]$-17α-hydroxyprogesterone having a final concentration of 10 nM, NADPH solution and the test compound were was dissolved in a 100 mM phosphate buffer solution (10 μl, pH 7.4). Microsome protein (7 μg/10 μl) was added and the mixture was incubated at 37° C. for 7 min. Ethyl acetate (40 μl) was added and the mixture was centrifuged, and the substrate and the product (androstenedione and testosterone) in the supernatant were separated by silica gel thin layer chromatography (TLC). The spot was detected and quantitatively assayed by a BAS 2000 bioimage analyzer. Taking the production amount when the test compound was not added (control) as 100%, the concentration ($IC_{50}$) of the compound necessary for 50% inhibition of the product amount relative to the control was calculated. The results are shown in Table 16.

TABLE 16

In vitro enzyme inhibitory activity ($IC_{50}$)

| Comp. No. | Rat $C_{17,20}$-lyase (nM) |
|---|---|
| 49 | 33 |
| 53 | <10 |
| 64 | <10 |
| 78 | <10 |
| 85 | 30 |
| 103 | <10 |
| 136 | 14 |

INDUSTRIAL APPLICABILITY

The compound of the present invention, a salt thereof and a prodrug thereof have a steroid $C_{17,20}$-lyase-inhibitory activity and are useful for the therapy and prophylaxis of various diseases such as primary cancer, metastasis or recrudescence of malignant tumor, various symptoms associated with these cancers, prostatic hypertrophy, masculinism, hypertrichosis, male type baldness, male infant-type prematurity, endometriosis, hysteromyoma, mastopathy, polycystic ovary syndrome and the like in mammals.

This application is based on patent application No. 373868/2000 filed in Japan, the contents of which are hereby incorporated by reference.

What is claimed is:

1. A compound represented by the formula:

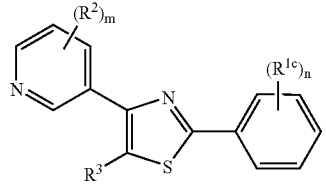

(Ib)

wherein
n is an integer of 1 to 5,
$R^{1c}$ is a carbamoyl group optionally having substituents selected from the group consisting of a $C_{1-6}$ alkyl and a $C_{6-14}$ aryl, or an alkylsulfonyl group optionally having halogen atom as a substituent, or two $R^{1c}$ substituting adjacent carbon atoms are bonded to designate a $C_{1-2}$ alkylenedioxy group, and when n is not less than 2, $R^{1c}$ in the number of n are the same or different,
m is an integer of 1 to 5,
$R^2$ is 1) a hydrogen atom, 2) a $C_{1-4}$ aliphatic hydrocarbon group optionally having substitutents selected from the group consisting of halogen atom, a hydroxy and carboxy, 3) a carboxyl group optionally esterified by $C_{1-6}$ alkyl group, 4) a carbamoyl group optionally having substitutents selected from a $C_{1-6}$ alkyl and a $C_{6-14}$ aryl, 5) an amino group optionally having substitutents selected from the group consisting of a $C_{1-6}$ alkyl, a $C_{6-14}$ aryl, a formyl, a $C_{1-6}$ alkyl-carbonyl, a $C_{1-4}$ aryl-carbonyl, a $C_{1-6}$ alkoxy-carbonyl, a $C_{1-6}$ alkylsulfonyl and a $C_{6-14}$ arylsulfonyl, 6) an unsubstituted $C_{1-6}$ alkylthio, optionally halogenated $C_{1-6}$ alkylthio or a $C_{7-16}$ aralkylthio, or 7) an optionally halogenated $C_{1-6}$ alkoxy group or a $C_{1-6}$ alkoxy-carbonyl-$C_{1-6}$ alkoxy group, or two $R^2$ substituting adjacent carbon atoms may be bonded to form 8) a saturated or unsaturated divalent $C_{3-5}$ carbon chain, and when m is not less than 2, $R^2$ in the number of m may be the same or different, and
$R^3$ is 1) a hydrogen atom, 2) a halogen atom, 3) a $C_{1-4}$ aliphatic hydrocarbon group optionally having substituents selected from the group consisting of halogen atom, a hydroxy and carboxy or 4) a carboxyl group optionally esterified by $C_{1-6}$ alkyl group,
or a salt thereof.

2. The compound of claim 1, wherein $R^{1c}$ is 1) a carbamoyl group optionally having $C_{1-4}$ alkyl or $C_{7-9}$ aralkyl as a substituent or 2) a $C_{1-4}$ alkylsulfonyl group, or two $R^{1b}$ substituting adjacent carbon atoms are bonded to designate a $C_{1-2}$ alkylenedioxy group, $R^2$ is 1) a hydrogen atom, 2) a $C_{1-4}$ alkyl optionally having halogen or hydroxy as a substituent, 3) a carboxyl group, 4) a $C_{1-4}$ alkoxycarbonyl group, 5) a carbamoyl group optionally having $C_{1-4}$ alkyl or $C_{7-9}$ aralkyl as a substituent, 6) an amino group optionally having $C_{1-4}$ alkyl, carbamoyl-$C_{1-4}$ alkyl or $C_{7-10}$ aralkyl as a substituent, 7) a $C_{1-4}$ alkylthio group or 8) a $C_{1-4}$ alkoxy group, or two $R^2$ substituting adjacent carbon atoms are bonded to form 9) a butadienylene group, and $R^3$ is 1) a hydrogen atom, 2) a halogen atom, 3) a $C_{1-4}$ alkyl group, 4) a carboxyl group or 5) a $C_{1-4}$ alkoxycarbonyl group.

3. A compound represented by the formula:

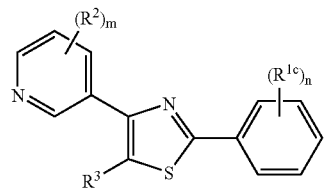

(Ib)

wherein
n is an integer of 1 to 5,
m is an integer of 1 to 5,
$R^{1c}$ is a carbamoyl group, a methylcarbamoyl group, or a dimethylcarbamoyl group,
$R^2$ is a hydrogen atom, a methyl group, an ethyl group or an isopropyl group, and
$R^3$ is a hydrogen atom, a chlorine atom, a methyl group or an isopropyl group,
or a salt thereof.

4. A compound represented by the formula:

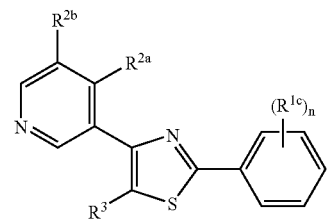

(Ib1)

wherein
n is an integer of 1 to 5,
$R^{1c}$ is a carbamoyl group optionally having substituents selected from the group consisting of a $C_{1-6}$ alkyl and a $C_{6-14}$ aryl, or an alkylsulfonyl group optionally having a halogen atom as a substituent, or two $R^{1c}$ substituting adjacent carbon atoms are bonded to designate a $C_{1-2}$ alkylenedioxy group, and when n is not less than 2, $R^{1c}$ in the number of n are the same or different,
$R^{2a}$ and $R^{2b}$ are the same or different and each is 1) a hydrogen atom, 2) a $C_{1-4}$ aliphatic hydrocarbon group optionally having substituents selected from the group consisting of halogen atom, a hydroxy and carboxy, 3) a carboxyl group optionally esterified by $C_{1-6}$ alkyl group, 4) a carbamoyl group optionally having substitutents selected from the group consisting a $C_{1-6}$ alkyl and a $C_{6-14}$ aryl, 5) an amino group optionally having substituents selected from the group consisting of a $C_{1-6}$ alkyl, a $C_{6-14}$ aryl, a formyl, a $C_{1-6}$ alkyl-carbonyl, a $C_{6-14}$ aryl-carbonyl, a $C_{1-6}$ alkoxy-carbonyl, a $C_{1-6}$ alkylsulfonyl and a $C_{6-14}$ arylsulfonyl, 6) an unsubstituted $C_{1-6}$ alkylthio, optionally halogenated $C_{1-6}$ alkylthio or a $C_{7-16}$ aralkylthio or 7) an optionally halogenated $C_{1-6}$ alkoxy group or a $C_{1-6}$ alkoxy-carbonyl-$C_{1-6}$ alkoxy group, or $R^{2a}$ and $R^{2b}$ may be bonded to form 8) a saturated or unsaturated divalent $C_{3-5}$ carbon chain, and
$R^3$ is 1) a hydrogen atom, 2) a halogen atom, 3) a $C_{1-4}$ aliphatic hydrocarbon group optionally having substituents selected from the group consisting of halogen atom, a hydroxy and carboxy or 4) a carboxyl group optionally esterified by $C_{1-6}$ alkyl group, or a salt thereof.

5. The compound of claim 4, wherein $R^{1c}$ is 1) a carbamoyl group optionally having $C_{1-4}$ alkyl or $C_{7-9}$ aralkyl as a substituent or 2) a $C_{1-4}$ alkylsulfonyl group, or two $R^{1b}$ substituting adjacent carbon atoms are bonded to designate a $C_{1-2}$ alkylenedioxy group, $R^{2a}$ and $R^{2b}$ are the same or different and each is 1) a hydrogen atom, 2) a $C_{1-4}$ alkyl optionally having halogen or hydroxy as a substituent, 3) a carboxyl group or $C_{1-4}$ alkoxycarbonyl group, 4) a carbamoyl group optionally having $C_{1-4}$ alkyl or $C_{7-9}$ aralkyl as a substituent, 5) an amino group optionally having $C_{1-4}$ alkyl, carbamoyl-$C_{1-4}$ alkyl or $C_{7-10}$ aralkyl as a substituent, 6) a $C_{1-4}$ alkylthio group or 7) a $C_{1-4}$ alkoxy group, or $R^{2a}$ and $R^{2b}$ are bonded to form a butadienylene group, and $R^3$ is 1) a hydrogen atom, 2) a halogen atom, 3) a $C_{1-4}$ alkyl group, 4) a carboxyl group or 5) a $C_{1-4}$ alkoxycarbonyl group.

6. A compound represented by the formula:

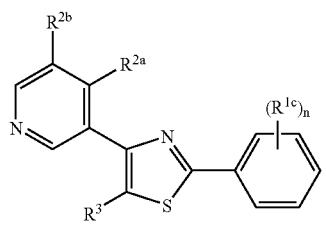

(Ib1)

wherein n is an integer of 1 to 5, $R^{1c}$ is a carbamoyl group, a methylcarbamoyl group, or a dimethylcarbamoyl group, $R^{2a}$ is a methyl group, an ethyl group or an isopropyl group, $R^{2b}$ is a hydrogen atom, and $R^3$ is a hydrogen atom, a chlorine atom, a methyl group or an isopropyl group, or a salt thereof.

7. A compound represented by the formula:

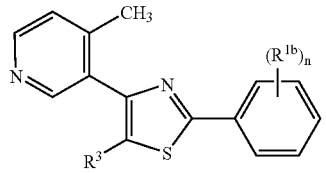

(Ib2)

wherein n is an integer of 1 to 5, $R^{1b}$ is 1) a sulfamoyl group optionally having a $C_{1-6}$ alkyl or a $C_{7-15}$ aralkyl as a substituent, 2) a carbamoyl group optionally having substituents selected from the group consisting of a $C_{1-6}$ alkyl and a $C_{6-14}$ aryl, 3) an alkyl group optionally having a halogen atom or a hydroxy as a substituent, 4) a carboxyl group optionally esterified by $C_{1-6}$ alkyl group, 5) a halogen atom, 6) an ammo group optionally having substituents selected from the group consisting of a $C_{1-6}$ alkyl, a $C_{6-14}$ aryl, a formyl, a $C_{1-6}$ alkyl-carbonyl, a $C_{6-14}$ aryl-carbonyl, a $C_{1-6}$ alkoxy-carbonyl, a $C_{1-6}$ alkylsulfonyl and a $C_{6-14}$ arylsulfonyl, 7) a nitro group, 8) an unsubstituted hydroxy, optionally halogenated $C_{1-8}$ alkoxy, a $C_{1-6}$ alkoxy-carbonyl-$C_{1-6}$ alkoxy, a $C_{6-14}$ aryloxy, a $C_{7-16}$ aralkyloxy, a $C_{1-6}$ alkyl-carbonyloxy, a $C_{6-14}$ aryl-carbonyloxy, a $C_{1-6}$ alkoxy-carbonyloxy, a mono-$C_{1-6}$ alkyl-carbamoyloxy, a di-$C_{1-6}$ alkyl-carbamoyloxy, or a $C_{6-14}$ aryl-carbamoyloxy, or 9) an alkylsulfonyl group optionally having halogen atom as a substituent, or two $R^{1b}$ substituting adjacent carbon atoms are bonded to designate a $C_{1-2}$ alkylenedioxy group, and when n is not less than 2, $R^{1b}$ in the number of n may be the same or different, and $R^3$ is 1) a hydrogen atom, 2) a halogen atom, 3) a $C_{1-4}$ aliphatic hydrocarbon group optionally having substituents selected from the group consisting of halogen atom, a hydroxy and carboxy or 4) a carboxyl group optionally esterified by $C_{1-6}$ alkyl group, or a salt thereof.

8. The compound of claim 7, wherein $R^{1b}$ is 1) a sulfamoyl group optionally having $C_{1-4}$ alkyl or $C_{7-9}$ aralkyl as a substituent, 2) a carbamoyl group optionally having $C_{1-4}$ alkyl or $C_{7-9}$ aralkyl as a substituent, 3) a $C_{1-4}$ alkyl group optionally having halogen as a substituent, 4) a carboxyl group, 5) a $C_{1-4}$ alkoxycarbonyl group, 6) a halogen atom, 7) an amino group optionally having $C_{1-6}$ alkanoyl, $C_{1-4}$ alkyl or $C_{1-4}$ alkylsulfonyl as a substituent, 8) a nitro group, 9) a hydroxy group optionally having $C_{1-4}$ alkyl or $C_{1-6}$ alkanoyl as a substituent or 10) a $C_{1-4}$ alkylsulfonyl group, or two $R^{1b}$ substituting adjacent carbon atoms are bonded to designate a $C_{1-2}$ alkylenedioxy group, and $R^3$ is 1) a hydrogen atom, 2) a halogen atom, 3) a $C_{1-4}$ alkyl group, 4) a carboxyl group or 5) a $C_{1-4}$ alkoxycarbonyl group.

9. The compound of claim 7, wherein $R^{1b}$ is a sulfamoyl group, a carbamoyl group, a methylcarbamoyl group, a dimethylcarbamoyl group, a methyl group, a chlorine atom, a fluorine atom, an acetylamino group, a formylamino group or nitro group, and $R^3$ is a hydrogen atom, a chlorine atom, a methyl group or an isopropyl group.

10. A compound represented by the formula:

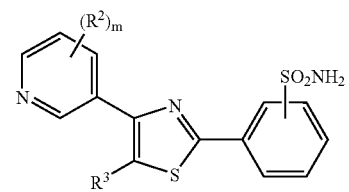

(Ib3)

wherein m is an integer of 1 to 5, $R^2$ is 1) a hydrogen atom, 2) a $C_{1-4}$ aliphatic hydrocarbon group optionally having substituents selected from the group consisting of halogen atom, a hydroxy and carboxy, 3) a carboxyl group optionally esterified by $C_{1-6}$ alkyl group, 4) a carbamoyl group optionally having substituents selected from the group consisting of a $C_{1-6}$ alkyl and a $C_{6-14}$ aryl, 5) an amino group optionally having substituents selected from the group consisting of a $C_{1-6}$ alkyl, a $C_{6-14}$ aryl, a formyl, a $C_{1-6}$ alkyl-carbonyl, a $C_{6-14}$ aryl-carbonyl, a $C_{1-6}$ alkoxy-carbonyl, a $C_{1-6}$ alkylsulfonyl, and a $C_{6-14}$ arylsulfonyl, 6) an unsubstituted $C_{1-6}$ alkylthio, optionally halogenated $C_{1-6}$ alkylthio or a $C_{7-16}$ aralkylthio, or 7) an optionally halogenated $C_{1-6}$ alkoxy group or a $C_{1-6}$ alkoxy-carbonyl-$C_{1-6}$ alkoxy group, or two $R^2$ substituting adjacent carbon atoms are bonded to form 8) a saturated or unsaturated divalent $C_{3-5}$ carbon chain, and when m is not less than 2, $R^2$ in the number of m may be the same or different, and $R^3$ is 1) a hydrogen atom, 2) a halogen atom, 3) a $C_{1-4}$ aliphatic hydrocarbon group optionally having substituents selected from the group consisting of halogen atom, a hydroxy and carboxy or 4) a carboxyl group optionally esterified by $C_{1-6}$ alkyl group, or a salt thereof.

11. A compound represented by the formula:

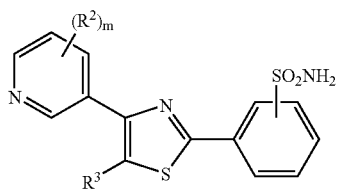

(Ib3)

wherein m is an integer of 1 to 5, $R^2$ is 1) a hydrogen atom, 2) a $C_{1-4}$ alkyl optionally having halogen or hydroxy as a substituent, 3) a carboxyl group, 4) a $C_{1-4}$ alkoxycarbonyl group, 5) a carbamoyl group optionally having $C_{1-4}$ alkyl or $C_{7-9}$ aralkyl as a substituent, 6) an amino group optionally having $C_{1-4}$ alkyl, carbamoyl-$C_{1-4}$ alkyl or $C_{7-10}$ aralkyl as a substituent, 7) a $C_{1-4}$ alkylthio group or 8) a $C_{1-4}$ alkoxy group, or two adjacent $R^2$ are bonded to form 9) a butadienylene group, and $R^3$ is 1) a hydrogen atom, 2) a halogen atom, 3) a $C_{1-4}$ alkyl group, 4) a carboxyl group or 5) a $C_{1-4}$ alkoxycarbonyl group, or a salt thereof.

12. A compound represented by the formula:

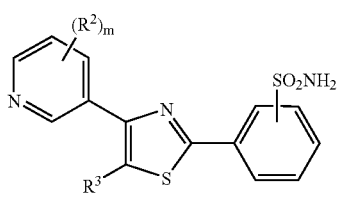

(Ib3)

wherein m is an integer of 1 to 5, $R^2$ is a hydrogen atom, a methyl group or an ethyl group and $R^3$ is a hydrogen atom or a methyl group, or a salt thereof.

13. A compound represented by the formula:

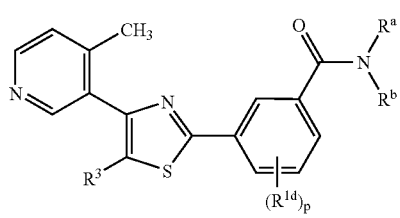

(Ib4)

wherein p is 0 or an integer of 1 to 5, $R^a$ and $R^b$ are the same or different and each is a hydrogen atom or a $C_{1-6}$ lower alkyl group, $R^{1d}$ is 1) a hydrogen atom, 2) a $C_{1-4}$ aliphatic hydrocarbon group optionally having substituents selected from the group consisting of halogen atom, a hydroxy and carboxy, 3) a sulfamoyl group optionally having substituents selected from the group consisting of a $C_{1-6}$ alkyl and a $C_{7-15}$ aralkyl, 4) a carbamoyl group optionally having substituents selected from the group consisting of a $C_{1-6}$ alkyl and a $C_{6-14}$ aryl, 5) a carboxyl group optionally esterified by $C_{1-6}$ alkyl group, 6) a halogen atom, 7) an amino group optionally having substituents selected from the group consisting of a $C_{1-6}$ alkyl, a $C_{6-14}$ aryl, a formyl, a $C_{1-6}$ alkyl-carbonyl, a $C_{6-14}$ aryl-carbonyl, a $C_{1-6}$ alkoxy-carbonyl, a $C_{1-6}$ alkylsulfonyl and a $C_{6-14}$ arylsulfonyl, 8) an unsubstituted hydroxyl, optionally halogenated $C_{1-8}$ atkoxy, a $C_{1-6}$ alkoxy-carbonyl-$C_{1-6}$ alkoxy, a $C_{6-14}$ aryloxy, a $C_{7-16}$ aralkyloxy, a $C_{1-6}$ alkyl-carbonyloxy, a $C_{6-14}$ aryl-carbonyloxy, a $C_{1-6}$ alkoxy-carbonyloxy, a mono-$C_{1-6}$ alkyl-carbamoyloxy, a di-$C_{1-6}$ alkyl-carbamoyloxy and a $C_{6-14}$ aryl-carbamoyloxy, 9) an unsubstituted $C_{1-6}$ alkylthio, optionally halogenated $C_{1-6}$ alkylthio or a $C_{7-16}$ aralkylthio, 10) a nitro group, 11) an alkylsulfonyl group optionally having halogen atom as a substituent, or 12) two $R^{1d}$ substituting adjacent carbon atoms maybe bonded to form 12a) a $C_{1-2}$ alkylenedioxy group or 12b) a saturated or unsaturated divalent $C_{3-5}$ carbon chain, and when p is not less than 2, $R^{1d}$ in the number of p may be the same or different, and $R^3$ is 1) a hydrogen atom, 2) a halogen atom, 3) a $C_{1-4}$ aliphatic hydrocarbon group optionally having substituents selected from the group consisting of halogen atom, a hydroxy and carboxy or 4) a carboxyl group optionally esterified by $C_{1-6}$ alkyl group, or a salt thereof.

14. A compound represented by the formula:

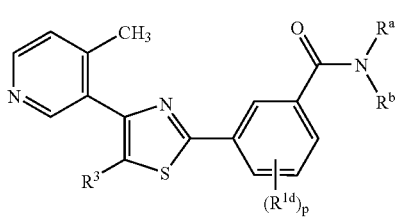

(Ib4)

wherein p is 0 or an integer of 1 to 5, $R^a$ and $R^b$ are the same or different and each is a hydrogen atom or a methyl group, $R^{1d}$ is a hydrogen atom, a methyl group, a chlorine atom or a fluorine atom, and $R^3$ is a hydrogen atom, a chlorine atom, a methyl group or an isopropyl group, or a salt thereof.

15. 3-[2-(4-fluorophenyl)-1,3-thiazol-4-yl]-4-methylpyridine, 4-[4-(4-methyl-pyridin-3-yl)-1,3-thiazol-2-yl]benzenesulfonamide or a salt thereof.

16. A pharmaceutical composition which comprises a compound of claim 1 and a pharmaceutically acceptable carrier.

17. A pharmaceutical composition which comprises a compound of claim 4 and a pharmaceutically acceptable carrier.

18. A pharmaceutical composition which comprises a compound of claim 7 and a pharmaceutically acceptable carrier.

19. A pharmaceutical composition which comprises a compound of claim 10 and a pharmaceutically acceptable carrier.

20. A pharmaceutical composition which comprises a compound of claim 13 and a pharmaceutically acceptable carrier.

21. A pharmaceutical composition which comprises a compound of claim 15 and a pharmaceutically acceptable carrier.

* * * * *